(12) United States Patent
Minatti et al.

(10) Patent No.: US 8,921,363 B2
(45) Date of Patent: Dec. 30, 2014

(54) DERIVATIVES OF 1 H-ISOINDOL-3-AMINE, 1 H-ISO-AZA-INDOL-3AMINE, 3,4-DIHYDROISOQUINOLIN-1-AMINE, AND 1,4-DIHYDROISOQUINOLIN-3-AMINE AS BETA-SECRETASE INHIBITORS

(75) Inventors: Ana Elena Minatti, Santa Monica, CA (US); Yuan Cheng, Newbury Park, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/814,232

(22) PCT Filed: Aug. 4, 2011

(86) PCT No.: PCT/US2011/046667
§ 371 (c)(1),
(2), (4) Date: Mar. 7, 2013

(87) PCT Pub. No.: WO2012/019056
PCT Pub. Date: Feb. 9, 2012

(65) Prior Publication Data
US 2013/0172343 A1 Jul. 4, 2013

Related U.S. Application Data

(60) Provisional application No. 61/371,096, filed on Aug. 5, 2010.

(51) Int. Cl.
| | | |
|---|---|---|
| C07D 491/20 | (2006.01) | |
| A61K 31/436 | (2006.01) | |
| A61K 31/437 | (2006.01) | |
| A61K 31/537 | (2006.01) | |
| C07D 491/22 | (2006.01) | |
| C07D 498/20 | (2006.01) | |
| C07D 498/22 | (2006.01) | |

(52) U.S. Cl.
CPC ............ *C07D 491/20* (2013.01); *A61K 31/436* (2013.01); *A61K 31/437* (2013.01); *A61K 31/537* (2013.01); *C07D 491/22* (2013.01); *C07D 498/20* (2013.01); *C07D 498/22* (2013.01)
USPC ...................... 514/234.5; 514/232.8; 514/256; 514/278; 544/230; 544/70; 544/71; 546/18

(58) Field of Classification Search
CPC . A61K 31/436; A61K 31/537; A61K 31/437; C07D 498/22; C07D 491/22; C07D 498/20; C07D 491/20
USPC ............ 514/234.5, 278, 232.8, 256; 544/230, 544/70, 71; 546/15, 18
See application file for complete search history.

(56) References Cited

U.S. PATENT DOCUMENTS

| | | | |
|---|---|---|---|
| 8,426,447 B2 * | 4/2013 | White et al. ................. | 514/336 |
| 2007/0203116 A1 | 8/2007 | Quagiato et al. | |
| 2008/0287462 A1 | 11/2008 | Chessari et al. | |

FOREIGN PATENT DOCUMENTS

| | | |
|---|---|---|
| WO | 2006138265 A1 | 12/2006 |
| WO | 2007149033 A1 | 12/2007 |
| WO | 2009005470 A1 | 1/2009 |
| WO | 2009005471 A1 | 1/2009 |
| WO | 2009022961 A1 | 2/2009 |
| WO | 2010030954 A1 | 3/2010 |
| WO | 2010056194 A1 | 5/2010 |
| WO | 2010056195 A1 | 5/2010 |
| WO | 2010056196 A1 | 5/2010 |
| WO | 2011002409 A1 | 1/2011 |

OTHER PUBLICATIONS

Joachim et al., Alz. Dis. Assoc. Dis., 6:7-34 (1992).
Selkoe, Neuron, 6:487 (1991).
Seubert et al., Nature, 359:325-327 (1992).
Citron, Trends in Pharmacological Sciences, 25(2):92-97 (2004).
Nature Medicine (Jun. 22, 2008).
Nature, 402:537-554 (1999) (p. 510).
Sabbagh, M. et al., Alz. Dis. Rev. 3:1-19 (1997).
Cole, S.L., Vasser, R., Molecular Degeneration 2:22, 2007.
Luo et al., Nature Neuroscience, 4:231-232 (2001).
Bioorganic & Medicinal Chemistry Letters 20 (2010) 2068-2073.
J. Med. Chem. 2009.
Alzheimer's Research & Therapy 2009.
Expert Opin. Emerging Drugs (2008) 13(2):255-271.
J. Med. Chem. 2008, 51, 6259-6262.
Chem. Soc. Rev., 2009, 38, 2698-2715.
Sabbagh_ClinicalDev_2009.
J. Neurosci., Oct. 14, 2009 • 29(41):12787-12794.
Zhou_et_al_ARKIVOC_2010_vi_84-88.
Nowak_Bioorganic_Medicinal_Chemistry_Letters_2009.
Malamas_Bioorganic_Medicinal_Chemistry_Letters_2009.
Zhou_Bioorganic_Medicinal_Chemistry_Letters_2010.
Malamas_JMedChem_2009.

* cited by examiner

*Primary Examiner* — Savitha Rao
*Assistant Examiner* — Angela Brown-Pettigrew
(74) *Attorney, Agent, or Firm* — G. Prabhakar Reddy

(57) ABSTRACT

The present invention relates to a compound represented by general formula I:

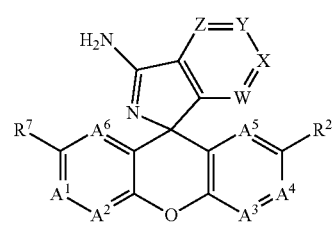

or a stereoisomer, tautomer, hydrate, solvate or pharmaceutically acceptable salt thereof, wherein $A^1$, $A^2$, $A^3$, $A^4$, $A^5$, $A^6$, $R^2$, $R^7$, W, X, Y and Z are defined within. These compounds are useful for the modulation of β-secretase enzyme activity and for the treatment of β-secretase mediated diseases, including Alzheimer's disease (AD) and related conditions.

7 Claims, No Drawings

DERIVATIVES OF 1 H-ISOINDOL-3-AMINE, 1 H-ISO-AZA-INDOL-3AMINE, 3,4-DIHYDROISOQUINOLIN-1-AMINE, AND 1,4-DIHYDROISOQUINOLIN-3-AMINE AS BETA-SECRETASE INHIBITORS

RELATED APPLICATIONS

This application is a US national stage application via 35 USC §371(c) of PCT/US2011/046667, filed on Aug. 4, 2011, which PCT application claims the benefit of U.S. Provisional Application No. 61/371,096, filed Aug. 5, 2010, both specifications of which are hereby incorporated herein by reference in their entireties.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and related central nervous system (CNS) disorders.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

In addition, the approach of regulating or reducing the formation of A-beta peptide formation and deposition has received tremendous attention and belief. A small molecule gamma-secretase inhibitor, LY450139 ("Semagacestat"), an A-beta lowering agent, is in phase II and Phase III clinical trials for the treatment of Alzheimer's Disease. The pharmacokinetics of semagacestat in plasma, as well as the plasma and cerebral spinal fliud (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology*, 2006, 66 (pgs 602-624)).

Several approaches have been taken to potentially treat AD and plaque-related disorders. One approach has been to attempt to reduce the formation of plaque on the brain, by inhibiting or reducing the activity of BACE. For example, each of the following PCT publications: WO 10/002,409, WO 10/56194, WO 10/56195, WO 10/56196, WO 09/005,470, WO 09/005,471, WO 09/022,961, WO 09/091,016, WO 08/108,378, WO 09/134,617, WO 05/097767, WO 08/092, 785, WO 06/138265, WO 08/103,351, WO 06/138265, WO 06/138230, WO 08/200,445, WO 06/111370, WO 07/149, 033, WO 07/287,692, WO 05/058311, EP 01942105, WO 08/133,273, WO 08/133,274, WO 07/049,532, US20070027199, WO 07/038,271, US20070287462, US20070072925, US20070203116, WO 08/118,379, WO 06/076284, US20070004786, WO 06/083760, WO 07/011, 810, WO 07/011,833 and WO 08/054,698, describe inhibitors of BACE, useful for treating AD and other beta-secretase mediated disorders.

Despite the many efforts and resources directed to researching A-beta lowering agents, there remains a need to identify safe and efficacious treatment agents for AD.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

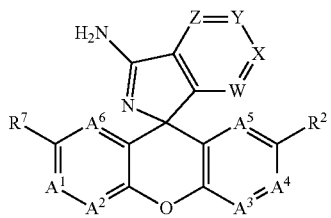

I wherein each of $A^1$, $A^2$, $A^3$, $A^4$, $A^5$, $A^6$, $R^2$, $R^7$, W, X, Y and Z of Formula I are defined below. The invention also provides procedures for making compounds of sub-Formulas thereof, as well as intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts thereof, are generally defined by the compound of Formula I:

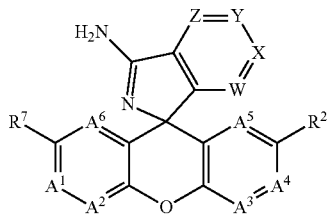

I wherein
$A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1$, $A^2$, $A^3$, $A^4$, $A^5$ and $A^6$ is N;
each of $R^1$, $R^4$, $R^5$ and $R^8$, independently, is H, F, Cl, Br, $CF_3$, $OCF_3$, $C_{1-6}$-alkyl, CN, OH, $-OC_{1-6}$-alkyl, $-S(O)_o C_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;

R$^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$ alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo [3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$ alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1] oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

each of R$^3$ and R$^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

R$^7$ is C$_{1-6}$-alkyl, C$_{2-4}$alkenyl, C$_{2-4}$alkynyl, CN, —OC$_{1-6}$ alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1] oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1] hept-5-yl, 2-oxo-7-aza-[3,5]-spironon-7-yl, cyclopentyl and cyclohexyl are optionally substituted, independently, with 1-3 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl;

each of W, X, Y and Z, independently, is CR$^{10}$ or N, wherein each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, provided that no more than two of W, X, Y and Z are N.

In another embodiment of the present invention, the compounds, and solvates, tautomers, stereoisomers and pharmaceutically acceptable salts thereof, are defined by Formula I-A

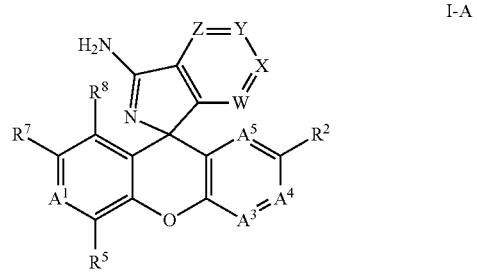

I-A wherein
A$^1$ is CR$^6$ or N;
A$^3$ is CR$^4$ or N;
A$^4$ is CR$^3$ or N; provided no more than one of A$^1$, A$^3$ and A$^4$ is N;
A$^5$ is CR$^1$;
each of R$^1$, R$^4$, R$^5$ and R$^8$, independently, is H, F, Cl, Br, CF$_3$, OCF$_3$, CH$_3$, C$_2$H$_5$, CN, OH, OCH$_3$;

R$^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$ alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo [3.2.1]oct-3-yl, aza-bicyclo[2.2.1]hept-5-yl, 2-oxo-7-aza-[3, 5]-spironon-7-yl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$ alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of R$^9$;

each of R$^3$ and R$^6$, independently, is H, F, Cl, haloalkyl, haloalkoxyl, C$_{1-6}$-alkyl, CN, OH or OC$_{1-6}$-alkyl.

R$^7$ is C$_{1-6}$-alkyl, C$_{2-4}$alkenyl, C$_{2-4}$alkynyl, CN, —OC$_{1-6}$ alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1] oct-3-yl, aza-bicyclo[2.2.1]hept-5-yl, 2-oxo-7-aza-[3,5]-spironon-7-yl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1] hept-5-yl, 2-oxo-7-aza-[3,5]-spironon-7-yl and cyclohexyl are optionally substituted, independently, with 1-3 substituents of R$^9$;

each R⁹, independently, is halo, haloalkyl, CN, OH, NO$_2$, NH$_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl.

In another embodiment of the present invention, the compounds, and solvates, tautomers, stereoisomers and pharmaceutically acceptable salts thereof, are defined by Formula I-B

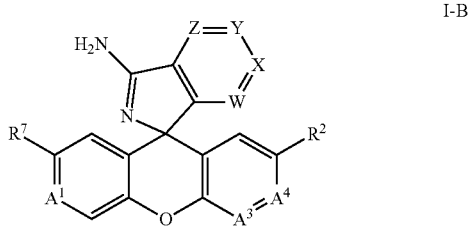

wherein each of $A^1$, $A^3$, $A^4$, $R^2$, $R^7$, W, X, Y and Z is as defined above with respect to Formula I.

In another embodiment of the present invention, the compounds, and solvates, tautomers, stereoisomers and pharmaceutically acceptable salts thereof, are defined by Formula I, wherein $A^1$ is CH or CF;
$A^2$ is CH;
$A^3$ is CH, CF or N;
$A^4$ is CH, CF or N;
$A^5$ is CH;
$A^6$ is CH;
$R^2$ is $C_{3-6}$-alkyl, $C_{2-4}$alkynyl, —O$C_{1-6}$allyl, —S$C_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —O$C_{1-6}$alkyl, —S$C_{1-6}$allyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;
$R^7$ is $C_{2-4}$alkynyl, —O$C_{1-6}$alkyl, phenyl, pyridyl, pyrimidyl, pyrazinyl or pyridazinyl, wherein the $C_{2-4}$alkynyl, —O$C_{1-6}$allyl, pyridyl, pyrimidyl, pyrazinyl and pyridazinyl are optionally substituted, independently, with 1-3 substituents of $R^9$;
each $R^9$, independently, is F, CF$_3$, CN, CH$_3$, —OCH$_3$, —SCH$_3$, —NHCH$_3$, oxetanyl or $C_{2-3}$allynyl;
X is N; and
each of W, Y and Z, independently, is CR$^{10}$, wherein each R$^{10}$, independently, is H, F, Cl, Br, CF$_3$, OCF$_3$, $C_{1-6}$-alkyl, CN, OH, —O$C_{1-6}$-alkyl, —S(O)$_o$$C_{1-6}$-alkyl, —NH$C_{1-6}$-alkyl or —C(O)$C_{1-6}$-alkyl, wherein the $C_{1-6}$-alkyl and $C_{1-6}$-alkyl portion of —O$C_{1-6}$-alkyl, —S(O)$_o$$C_{1-6}$-alkyl, —NH$C_{1-6}$-alkyl and —C(O)$C_{1-6}$-alkyl are optionally substituted with 1-3 substituents of F, oxo or OH.

In another embodiment of the present invention, the compounds, and solvates, tautomers, stereoisomers and pharmaceutically acceptable salts thereof, are defined by Formula I, wherein $A^1$ is CH or CF;
$A^2$ is CH;
$A^3$ is CH, CF or N;
$A^4$ is CH, CF or N;
$A^5$ is CH;
$A^6$ is CH;
$R^2$ is $C_{3-6}$-alkyl, $C_{2-4}$alkynyl, —O$C_{1-6}$alkyl, —S$C_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —O$C_{1-6}$alkyl, —S$C_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;
$R^7$ is $C_{2-4}$alkynyl, —O$C_{1-6}$alkyl, phenyl, pyridyl, pyrimidyl, pyrazinyl or pyridazinyl, wherein the $C_{2-4}$alkynyl, —O$C_{1-6}$alkyl, pyridyl, pyrimidyl, pyrazinyl and pyridazinyl are optionally substituted, independently, with 1-3 substituents of $R^9$;
each $R^9$, independently, is F, CF$_3$, CN, CH$_3$, —OCH$_3$, —SCH$_3$, —NHCH$_3$, oxetanyl or $C_{2-3}$alkynyl;
Y is N; and
each of W, X and Z, independently, is CR$^{10}$, wherein each R$^{10}$, independently, is H, F, Cl, Br, CF$_3$, OCF$_3$, $C_{1-6}$-alkyl, CN, OH, —O$C_{1-6}$-alkyl, —S(O)$_o$$C_{1-6}$-alkyl, —NH$C_{1-6}$-alkyl or —C(O)$C_{1-6}$-alkyl, wherein the $C_{1-6}$-alkyl and $C_{1-6}$-alkyl portion of —O$C_{1-6}$-alkyl, —S(O)$_o$$C_{1-6}$-alkyl, —NH$C_{1-6}$-alkyl and —C(O)$C_{1-6}$-alkyl are optionally substituted with 1-3 substituents of F, oxo or OH.

In another embodiment of the present invention, the compounds, and solvates, tautomers, stereoisomers and pharmaceutically acceptable salts thereof, are defined by Formula I, wherein $A^1$ is CH, CF or N;
$A^2$ is CH, CF or N;
$A^3$ is CH, CF or N;
$A^4$ is CH, CF or N;
$A^5$ is CH, CF, CBr or N;
$A^6$ is CH, CF or N; and
each of W, X, Y and Z, independently, is CR$^{19}$ or N, wherein each R$^{10}$, independently, is H, F, Cl, Br, CF$_3$, OCF$_3$, $C_{1-6}$-alkyl, CN, OH, —O$C_{1-6}$-alkyl, —S(O)$_o$$C_{1-6}$-alkyl, —NH$C_{1-6}$-alkyl or —C(O)$C_{1-6}$-alkyl, wherein the $C_{1-6}$-alkyl and $C_{1-6}$-alkyl portion of —O$C_{1-6}$-alkyl, —S(O)$_o$$C_{1-6}$-alkyl, —NH$C_{1-6}$-alkyl and —C(O)$C_{1-6}$-alkyl are optionally substituted with 1-3 substituents of F, oxo or OH, provided that no more than one of W, X, Y and Z are N.

In another embodiment of the present invention, the compounds, and solvates, tautomers, stereoisomers and pharmaceutically acceptable salts thereof, are defined by Formula I, wherein $A^1$ is CR$^6$ or N;
$A^2$ is CR$^5$ or N;
$A^3$ is CR$^4$ or N;
$A^4$ is CR$^3$ or N;
$A^5$ is CR$^1$ or N;
$A^6$ is CR$^8$ or N, provided that no more than one of $A^1$, $A^2$, $A^3$, $A^4$, $A^5$ and $A^6$ is N;

each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl and —NH-benzyl are optionally substituted, independently, with 1-3 substituents of $R^9$;

each of $R^3$ and $R^6$, independently, is H, halo, haloalkyl, haloalkoxy, $C_{1-6}$-alkyl, CN, OH, $OC_{1-6}$-alkyl, $SC_{1-6}$-alkyl, $NHC_{1-6}$-alkyl or $C(O)C_{1-6}$-alkyl; and one of each of W, X, Y and Z, independently, is N and the other three of W, X and Z, independently, is $CR^{10}$, wherein each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH.

In another embodiment of the present invention, the compounds, and solvates, tautomers, stereoisomers and pharmaceutically acceptable salts thereof, are defined by Formula I, wherein $A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1$, $A^2$, $A^3$, $A^4$, $A^5$ and $A^6$ is N;

each of $R^1$, $R^4$, $R^5$ and $R^8$, independently, is H, F, methyl, CN or OH;

$R^2$ is halo, haloalkyl, haloalkoxy, $C_{1-6}$-alkyl, $C_{2-4}$alkenyl, $C_{2-4}$alkynyl, $C_{3-8}$-cycloalkyl, $OR^{10}$, $SR^{10}$ or a ring of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, wherein the $C_{1-6}$-alkyl, $C_{2-4}$alkenyl, $C_{2-4}$alkynyl, $C_{3-8}$-cycloalkyl and ring are optionally substituted, independently, with 1-3 substituents of $R^9$;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and each of W, X, Y and Z, independently, is $CR^{19}$ wherein each $R^{10}$, independently, is H, F, Cl, Br, $CH_3$, $CF_3$, OH, $NO_2$, —$NHCH_3$, —$OCH_3$, —$OCF_3$, —$SCH_3$ or CN.

In another embodiment of the present invention, the compounds, and solvates, tautomers, stereoisomers and pharmaceutically acceptable salts thereof, are defined by Formula I-B-1

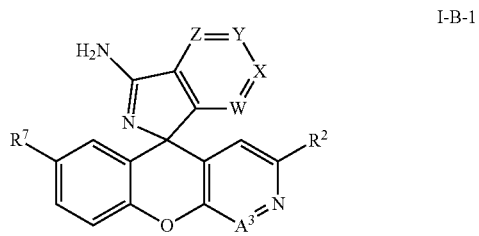

I-B-1 wherein $A^3$ is $CR^4$;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$allyl, —$N(C_{1-3}$allyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$allyl, —$SC_{1-6}$alkyl, —$NHC_{1-6}$allyl, —$N(C_{1-3}$allyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

$R^4$ is H, F, OH or $OC_{1-6}$allyl;

$R^7$ is $C_{1-6}$-alkyl, $C_{2-4}$alkenyl, $C_{2-4}$allynyl, CN, —$OC_{1-6}$allyl, —$SC_{1-6}$alkyl, —$NHC_{1-6}$alkyl, —$N(C_{1-3}$allyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$; and each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$allynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, wherein each of the $C_{1-6}$allyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and each of W, X, Y and Z, independently, is $CR^{10}$ or N, wherein each $R^{10}$, independently, is H, F, Cl, Br, $CF_3$, $OCF_3$, $C_{1-6}$-alkyl, CN, OH, $-OC_{1-6}$-alkyl, $-S(O)_oC_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, $-S(O)_oC_{1-6}$-alkyl, $-NHC_{1-6}$-alkyl and $-C(O)C_{1-6}$-alkyl are optionally substituted with 1-3 substituents of F, oxo or OH, provided that no more than one of W, X, Y and Z are N.

In another embodiment of the present invention, the compounds, and solvates, tautomers, stereoisomers and pharmaceutically acceptable salts thereof, are defined by Formula II

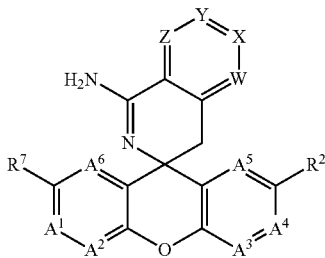

II $A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1$, $A^2$, $A^3$, $A^4$, $A^5$ and $A^6$ is N;

each of $R^1$, $R^4$, $R^5$ and $R^8$, independently, is H, F, Cl, Br, $CF_3$, $OCF_3$, $C_{1-6}$-alkyl, CN, OH, $-OC_{1-6}$-alkyl, $-S(O)_o C_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, $-S(O)_oC_{1-6}$-alkyl, $-NHC_{1-6}$-alkyl and $-C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or $-Si(CH_3)_3$, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each $R^9$, independently, is halo, haloalkyl, CN, OH, $NO_2$, $NH_2$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and each of W, X, Y and Z, independently, is $CR^{10}$ or N, wherein each $R^{10}$, independently, is H, F, Cl, Br, $CF_3$, $OCF_3$, $C_{1-6}$-alkyl, CN, OH, $-OC_{1-6}$-alkyl, $-S(O)_oC_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, $-S(O)_oC_{1-6}$-alkyl, $-NHC_{1-6}$-alkyl and $-C(O)C_{1-6}$-alkyl are optionally substituted with 1-3 substituents of F, oxo or OH, provided that no more than two of W, X, Y and Z is N.

In another embodiment of the invention, the compounds, including stereoisomers, tautomers, solvates, pharmaceutically acceptable salts, also generally defined by Formula II, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or $-Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_2$alkenyl, $C_{2-4}$alkynyl, CN, $-OC_{1-6}$alkyl, $-SC_{1-6}$alkyl, —NHC$_{1-6}$alkyl, —N(C$_{1-3}$alkyl)$_2$, —NH-phenyl or —NH-benzyl, wherein the C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl and —NH-benzyl are optionally substituted, independently, with 1-3 substituents of R$^9$; and each of R$^3$ and R$^6$, independently, is H, halo, haloalkyl, haloalkoxyl, C$_{1-6}$-alkyl, CN, OH, OC$_{1-6}$-alkyl, SC$_{1-6}$-alkyl, NHC$_{1-6}$-alkyl or C(O)C$_{1-6}$-alkyl;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino-, C$_{1-3}$thioalkoxyl, or oxetanyl; and each of W, X, Y and Z, independently, is CR$^{19}$ or N, wherein each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, provided that no more than one of W, X, Y and Z is N.

In another embodiment of the invention, the compounds, including stereoisomers, tautomers, solvates, pharmaceutically acceptable salts, also generally defined by Formula II, wherein A$^1$ is CH, CF or N;
A$^2$ is CH, CF or N;
A$^3$ is CH, CF or N;
A$^4$ is CH, CF or N;
A$^5$ is CH, CR$^1$ or N;
A$^6$ is CH, CF or N, provided that no more than one of A$^1$, A$^2$, A$^3$, A$^4$, A$^5$ and A$^6$ is N;
R$^1$ is F, Br or

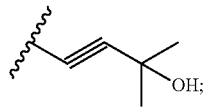 [SMILES: *C#CC(C)(C)O]

R$^2$ is Cl, Br, C$_{1-6}$-alkyl, C$_{2-4}$alkenyl, C$_{2-4}$alkynyl, CN, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

R$^7$ is C$_{1-6}$-alkyl, C$_{2-4}$alkenyl, C$_{2-4}$alkynyl, CN, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

each R$^9$, independently, is halo, haloalkyl, CN, OH, NO$_2$, NH$_2$, acetyl, —C(O)NHCH$_3$, oxo, C$_{2-6}$alkenyl, C$_{2-6}$alkynyl, C$_{3-6}$cycloalkyl, C$_{1-6}$thioalkoxyl, morpholinyl, pyrazolyl, isoxazolyl, dihydropyranyl, pyrrolidinyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino-, C$_{1-3}$thioalkoxyl, or oxetanyl; and each of W, X, Y and Z, independently, is CR$^{10}$ or N, wherein each R$^{10}$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, provided that no more than one of W, X, Y and Z is N.

In another embodiment of the invention, the compounds, including stereoisomers, tautomers, solvates, pharmaceutically acceptable salts, also generally defined by Formula II, wherein each of R$^1$, R$^4$, R$^5$ and R$^8$, independently, is H, F, Cl, CF$_3$, OCF$_3$, methyl, ethyl, CN, OH, OCH$_3$, SCH$_3$, NHCH$_3$ or C(O)CH$_3$;

one of R$^2$ and R$^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl and —NH-benzyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$alkyl, $SC_{1-6}$alkyl, $NHC_{1-6}$-alkyl or $C(O)C_{1-6}$-alkyl; and each of W, X, Y and Z, independently, is $CR^{10}$ or N, wherein each $R^{10}$, independently, is H, F, Cl, Br, $CF_3$, $OCF_3$, $C_{1-6}$-alkyl, CN, OH, —$OC_{1-6}$alkyl, —$S(O)_oC_{1-6}$alkyl, —$NHC_{1-6}$alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, provided that no more than one of W, X, Y and Z is N.

In another embodiment of the invention, the compounds, including stereoisomers, tautomers, solvates, pharmaceutically acceptable salts, also generally defined by Formula II, wherein each of $R^1$, $R^4$, $R^5$ and $R^8$, independently, is H, F, methyl, CN or OH;

$R^2$ is halo, haloalkyl, haloalkoxyl, $C_{1-6}$-alkyl, $C_{2-4}$alkenyl, $C_{2-4}$alkynyl, $C_{3-8}$-cycloalkyl, $OR^{10}$, $SR^{10}$ or a ring of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, wherein the $C_{1-6}$-alkyl, $C_{2-4}$alkenyl, $C_{2-4}$alkynyl, $C_{3-8}$-cycloalkyl and ring are optionally substituted, independently, with 1-3 substituents of $R^9$;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and each of W, X, Y and Z, independently, is $CR^{10}$ wherein each $R^{10}$, independently, is H, F, Cl, Br, $CH_3$, $CF_3$, OH, $NO_2$, —$NHCH_3$, —$OCH_3$, —$OCF_3$, —$SCH_3$ or CN.

In another embodiment of the invention, the compounds, including stereoisomers, tautomers, solvates, pharmaceutically acceptable salts, are generally defined by Formula III, wherein

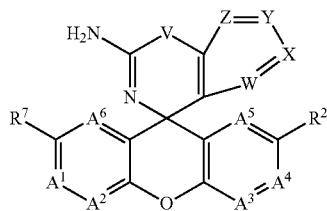

III wherein
$A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1$, $A^2$, $A^3$, $A^4$, $A^5$ and $A^6$ is N;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

V is $CR^{10}R^{10}$; $NR^{10}$, O or S;

each of W, X, Y and Z, independently, is $CR^{10}$ or N; and each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

provided that no more than two of W, X, Y and Z is N.

In another embodiment of the invention, the compounds, including stereoisomers, tautomers, solvates, pharmaceutically acceptable salts, also generally defined by Formula III, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl and —NH-benzyl are optionally substituted, independently, with 1-3 substituents of $R^9$; and each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl, or oxetanyl;

V is $CR^{10}R^{10}$, $NR^{10}$, O or S; and each of W, X, Y and Z, independently, is $CR^{19}$ or N, wherein each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, provided that no more than one of W, X, Y and Z is N.

In another embodiment of the invention, the compounds, including stereoisomers, tautomers, solvates, pharmaceutically acceptable salts, also generally defined by Formula III, wherein $A^1$ is CH, CF or N;
$A^2$ is CH, CF or N;
$A^3$ is CH, CF or N;
$A^4$ is CH, CF or N;
$A^5$ is CH, $CR^1$ or N;
$A^6$ is CH, CF or N, provided that no more than one of $A^1$, $A^2$, $A^3$, $A^4$, $A^5$ and $A^6$ is N;
$R^1$ is F, Br or

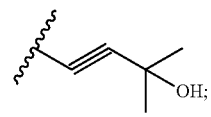

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$allyl, —$N(C_{1-3}$allyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$allyl, —$N(C_{1-3}$allyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

$R^7$ is $C_{1-6}$-alkyl, $C_{2-4}$alkenyl, $C_{2-4}$allynyl, CN, —$OC_{1-6}$alkyl, —$SC_{1-6}$alkyl, —$NHC_{1-6}$alkyl, —$N(C_{1-3}$allyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{2-6}$alkenyl, $C_{2-6}$alkynyl, $C_{3-6}$cycloalkyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino-, $C_{1-3}$thioalkoxyl, or oxetanyl;

V is $CR^{10}R^{10}$, $NR^{10}$, O or S; and each of W, X, Y and Z, independently, is $CR^{19}$ or N, wherein each $R^{10}$, independently, is H, F, Cl, Br, $CF_3$, $OCF_3$, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$NHC_{1-6}$-alkyl and —$C(O)C_{1-6}$-alkyl are optionally substituted with 1-3 substituents of F, oxo or OH, provided that no more than one of W, X, Y and Z is N.

In another embodiment of the invention, the compounds, including stereoisomers, tautomers, solvates, pharmaceutically acceptable salts, also generally defined by Formula III, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl or —NH-benzyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl and —NH-benzyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

V is $CR^{10}R^{10}$, $NR^{10}$, O or S; and each of W, X, Y and Z, independently, is $CR^{10}$ or N, wherein each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, provided that no more than one of W, X, Y and Z is N.

In another embodiment of the invention, the compounds, including stereoisomers, tautomers, solvates, pharmaceutically acceptable salts, also generally defined by Formula III, wherein each of $R^1$, $R^4$, $R^5$ and $R^8$, independently, is H, F, methyl, CN or OH;

$R^2$ is halo, haloalkyl, haloalkoxyl, $C_{1-6}$-alkyl, $C_{2-4}$alkenyl, $C_{2-4}$alkynyl, $C_{3-8}$-cycloalkyl, $OR^{10}$, $SR^{10}$ or a ring of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, wherein the $C_{1-6}$-alkyl, $C_{2-4}$alkenyl, $C_{2-4}$alkynyl, $C_{3-8}$-cycloalkyl and ring are optionally substituted, independently, with 1-3 substituents of $R^9$;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$;

V is O or S; and each of W, X, Y and Z, independently, is $CR^{10}$ wherein each $R^{10}$, independently, is H, F, Cl, Br, $CH_3$, $CF_3$, OH, $NO_2$, —$NHCH_3$, —$OCH_3$, —$OCF_3$, —$SCH_3$ or CN.

In another embodiment of the invention, the compounds, including stereoisomers, tautomers, solvates, pharmaceutically acceptable salts, are generally defined by Formula III-B, wherein

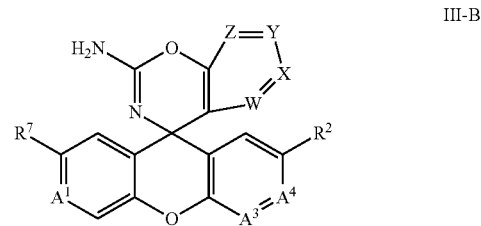

III-B wherein $A^1$ is $CR^6$ or N;

$A^3$ is $CR^4$ or N;

$A^4$ is $CR^3$ or N, provided that no more than one of $A^1$, $A^3$ and $A^4$ is N;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^4$ is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

each of W, X, Y and Z, independently, is $CR^{10}$ or N; and
each $R^{10}$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

provided that no more than two of W, X, Y and Z is N.

The present invention contemplates that the various different embodiments below of each individual variable $A^1$, $A^2$, $A^3$, $A^4$, $A^5$, $A^6$, $R^2$, $R^7$, W, X, Y and Z, as described below, may be applied "in conjunction with any of the other {above and below} embodiments" to create various embodiments of general Formulas I, I-A, I-B, II and III and each sub-formula thereof described hereinabove, which are not literally described herein.

In another embodiment, the invention includes compounds wherein $A^1$ is CH, CF or N, in conjunction with any of the above or below embodiments.

In another embodiment, the invention includes compounds wherein $A^1$ is CH or CF, in conjunction with any of the above or below embodiments.

In another embodiment, the invention includes compounds wherein $A^1$ is CF, in conjunction with any of the above or below embodiments.

In another embodiment, the invention includes compounds wherein $A^1$ is N, in conjunction with any of the above or below embodiments.

In another embodiment, the invention includes compounds wherein $A^2$ is CH, CF or N, in conjunction with any of the above or below embodiments.

In another embodiment, the invention includes compounds wherein $A^2$ is CH or CF, in conjunction with any of the above or below embodiments.

In another embodiment, the invention includes compounds wherein $A^2$ is N, in conjunction with any of the above or below embodiments.

In another embodiment, the invention includes compounds wherein $A^3$ is CH, CF or N, in conjunction with any of the above or below embodiments.

In another embodiment, the invention includes compounds wherein $A^3$ is CH or CF, in conjunction with any of the above or below embodiments.

In another embodiment, the invention includes compounds wherein $A^3$ is CF, in conjunction with any of the above or below embodiments.

In another embodiment, the invention includes compounds wherein $A^3$ is N, in conjunction with any of the above or below embodiments.

In another embodiment, the invention includes compounds wherein $A^4$ is CH, CF or N, in conjunction with any of the above or below embodiments.

In another embodiment, the invention includes compounds wherein $A^4$ is CH or CF, in conjunction with any of the above or below embodiments.

In another embodiment, the invention includes compounds wherein $A^4$ is CF, in conjunction with any of the above or below embodiments.

In another embodiment, the invention includes compounds wherein $A^4$ is N, in conjunction with any of the above or below embodiments.

In another embodiment, the invention includes compounds wherein $A^5$ is CH or $CR^1$ wherein $R^1$ is F, Br or

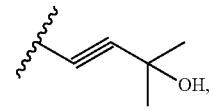 [SMILES: *C#CC(C)(C)O]

or $A^5$ is N, in conjunction with any of the above or below embodiments.

In another embodiment, the invention includes compounds wherein $A^5$ is CH, in conjunction with any of the above or below embodiments.

In another embodiment, the invention includes compounds wherein $A^5$ is $CR^1$ wherein $R^1$ is F, Br or

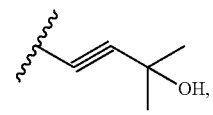

in conjunction with any of the above or below embodiments.

In another embodiment, the invention includes compounds wherein $A^5$ is N, in conjunction with any of the above or below embodiments.

In another embodiment, the invention includes compounds wherein $A^6$ is CH, CF or N, in conjunction with any of the above or below embodiments.

In another embodiment, the invention includes compounds wherein $A^6$ is CH or CF, in conjunction with any of the above or below embodiments.

In another embodiment, the invention includes compounds wherein $A^6$ is N, in conjunction with any of the above or below embodiments.

In another embodiment, the invention includes compounds wherein $R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$, in conjunction with any of the above or below embodiments.

In another embodiment, the invention includes compounds wherein R$^2$ is C$_{1-6}$-alkyl, C$_{2-4}$alkenyl, C$_{2-4}$alkynyl, —OC$_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$, in conjunction with any of the above or below embodiments.

In another embodiment, the invention includes compounds wherein R$^2$ is C$_{3-6}$-alkyl, C$_{3-8}$-cycloalkyl, C$_{2-4}$alkynyl, —OC$_{1-6}$alkyl, —SC$_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the C$_{3-6}$-alkyl, C$_{3-8}$-cycloalkyl, C$_{2-4}$alkynyl, —OC$_{1-6}$alkyl, —SC$_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl are optionally substituted, independently, with 1-3 substituents of R$^9$, in conjunction with any of the above or below embodiments.

In another embodiment, the invention includes compounds wherein R$^2$ is C$_{2-4}$alkynyl, —OC$_{1-6}$alkyl, pyridyl, pyrimidyl, dihydropyranyl, tetrahydropyranyl, pyrrolidinyl or piperidinyl, wherein the C$_{2-4}$alkynyl, —OC$_{1-6}$alkyl, pyridyl, pyrimidyl, dihydropyranyl, tetrahydropyranyl, pyrrolidinyl and piperidinyl are optionally substituted, independently, with 1-3 substituents of R$^9$, in conjunction with any of the above or below embodiments.

In another embodiment, the invention includes compounds wherein R$^2$ is C$_{2-4}$alkynyl, —OC$_{1-6}$alkyl, pyridyl, dihydropyranyl, pyrrolidinyl or piperidinyl, wherein the C$_{2-4}$alkynyl, —OC$_{1-6}$alkyl, pyridyl, dihydropyranyl, pyrrolidinyl and piperidinyl are optionally substituted, independently, with 1-3 substituents of R$^9$, in conjunction with any of the above or below embodiments.

In another embodiment, the invention includes compounds wherein R$^7$ is C$_{1-6}$-alkyl, C$_{2-4}$alkenyl, C$_{2-4}$alkynyl, CN, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$, in conjunction with any of the above or below embodiments.

In another embodiment, the invention includes compounds wherein R$^7$ is C$_{2-4}$alkynyl, —OC$_{1-6}$alkyl, phenyl, pyridyl, pyrimidyl, pyrazinyl or pyridazinyl, wherein the C$_{2-4}$alkynyl, OC$_{1-6}$alkyl, pyridyl, pyrimidyl, pyrazinyl and pyridazinyl are optionally substituted, independently, with 1-3 substituents of R$^9$, in conjunction with any of the above or below embodiments.

In another embodiment, the invention includes compounds wherein R$^7$ is C$_{2-4}$alkynyl, —OC$_{1-6}$alkyl, phenyl, 3-pyridyl, 5-pyrimidyl, pyrazinyl or 2-pyridazinyl, wherein the C$_{2-4}$alkynyl, 3-pyridyl, 5-pyrimidyl, pyrazinyl and 2-pyridazinyl are optionally substituted, independently, with 1-3 substituents of R$^9$, in conjunction with any of the above or below embodiments.

In another embodiment, the invention includes compounds wherein R$^7$ is a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, said ring optionally substituted, independently, with 1-3 substituents of R$^9$, in conjunction with any of the above or below embodiments.

In another embodiment, the invention includes compounds wherein R$^7$ is a ring selected from phenyl, 3-pyridyl, 5-pyrimidyl or 2-pyridazinyl, said ring optionally substituted, independently, with 1-5 substituents of R$^9$, in conjunction with any of the above or below embodiments.

In another embodiment, the invention includes compounds wherein R$^7$ is phenyl, 3-pyridyl, 5-pyrimidyl or 2-pyridazinyl, each of which is optionally substituted with 1-5 substituents of F, Cl, Br, I, CN, CF$_3$, C$_2$F$_5$, haloalkoxyl, C$_{1-6}$-alkyl, CN, OH, OC$_{1-6}$-alkyl, SC$_{1-6}$-alkyl, oxetanyl or C$_{2-3}$alkynyl, in conjunction with any of the above or below embodiments.

In another embodiment, the invention includes compounds wherein each R$^8$, independently, is F, Cl, CF$_3$, OCF$_3$, methyl, CN, OH, OCH$_3$, SCH$_3$, NHCH$_3$, oxetanyl or C$_{2-3}$alkynyl, in conjunction with any of the above or below embodiments.

In another embodiment, the invention includes compounds wherein each R$^9$, independently, is F, methyl, CN, OH, oxetanyl or C$_{2-3}$alkynyl, in conjunction with any of the above or below embodiments.

In another embodiment, the invention includes compounds wherein each R$^9$, independently, is F, CF$_3$, CN, CH$_3$, —OCH$_3$, —SCH$_3$, —NHCH$_3$, oxetanyl or C$_{2-3}$alkynyl, in conjunction with any of the above or below embodiments.

In another embodiment, the invention includes compounds wherein V is CR$^{10}$R$^{10}$, NR$^{10}$, O or S, in conjunction with any of the above or below embodiments.

In another embodiment, the invention includes compounds wherein V is NR$^{10}$, O or S, in conjunction with any of the above or below embodiments.

In another embodiment, the invention includes compounds wherein V is O or S, in conjunction with any of the above or below embodiments.

In another embodiment, the invention includes compounds wherein V is O, in conjunction with any of the above or below embodiments.

In another embodiment, the invention provides one or more of the compounds, or a pharmaceutically acceptable salt thereof, of Formulas I, II and III, as taught and described herein.

In another embodiment, the invention provides the compound of Formula I, or a pharmaceutically acceptable salt thereof, selected from 3-chloro-1-fluoro-7-(2-fluoropyridin-3-yl)spiro[chromeno[2,3-c]pyridine-5,1'-isoindol]-3'-amine;

1-fluoro-7-(2-fluoropyridin-3-yl)-3-(2-fluoropyridin-4-yl)spiro[chromeno[2,3-c]pyridine-5,1'-isoindol]-3'-amine;

(S)-1-fluoro-7-(2-fluoropyridin-3-yl)-3-(2-fluoropyridin-4-yl)spiro[chromeno[2,3-c]pyridine-5,1'-isoindol]-3'-amine;

(R)-1-fluoro-7-(2-fluoropyridin-3-yl)-3-(2-fluoropyridin-4-yl)spiro[chromeno[2,3-c]pyridine-5,1'-isoindol]-3'-amine;

3-(3,6-dihydro-2H-pyran-4-yl)-1-fluoro-7-(2-fluoropyridin-3-yl)spiro[chromeno[2,3-c]pyridine-5,1'-isoindol]-3'-amin;

3-(5,6-dihydro-2H-pyran-3-yl)-1-fluoro-7-(2-fluoropyridin-3-yl)spiro[chromeno[2,3-c]pyridine-5,1'-isoindol]-3'-amine;

(R)-3-(5,6-dihydro-2H-pyran-3-yl)-1-fluoro-7-(2-fluoropyridin-3-yl)spiro[chromeno[2,3-c]pyridine-5,1'-isoindol]-3'-amin;

(S)-3-(5,6-dihydro-2H-pyran-3-yl)-1-fluoro-7-(2-fluoropyridin-3-yl)spiro[chromeno[2,3-c]pyridine-5,1'-isoindol]-3'-amine;

1-fluoro-7-(2-fluoropyridin-3-yl)-3-morpholinospiro[chromeno[2,3-c]pyridine-5,1'-isoindol]-3'-amine;

3-(3,3-difluoropyrrolidin-1-yl)-1-fluoro-7-(2-fluoropyridin-3-yl)spiro[chromeno[2,3-c]pyridine-5,1'-isoindol]-3'-amine;

3-chloro-7-(2-fluoropyridin-3-yl)spiro[chromeno[2,3-c]pyridine-5,1'-isoindol]-3'-amine;

7-(2-fluoropyridin-3-yl)-3-(2-fluoropyridin-4-yl)spiro[chromeno[2,3-c]pyridine-5,1'-isoindol]-3'-amine;

3-(3,6-dihydro-2H-pyran-4-yl)-7-(2-fluoropyridin-3-yl)spiro[chromeno[2,3-c]pyridine-5,1'-isoindol]-3'-amine;

7-(2-fluoropyridin-3-yl)-3-(tetrahydro-2H-pyran-4-yl)spiro[chromeno[2,3-c]pyridine-5,1'-isoindol]-3'-amine;

3-(3,3-dimethylbut-1-ynyl)-7-(2-fluoropyridin-3-yl)spiro[chromeno[2,3-c]pyridine-5,1'-isoindol]-3'-amine;

(S)-3,7-bis(2-fluoropyridin-3-yl)spiro[chromeno[2,3-c]pyridine-5,1'-isoindol]-3'-amine;

3-chloro-1-fluoro-7-(2-fluoropyridin-3-yl)spiro[chromeno[2,3-c]pyridine-5,3'-pyrrolo[3,4-c]pyridin]-1'-amine;

(R)-3-chloro-1-fluoro-7-(2-fluoropyridin-3-yl)spiro[chromeno[2,3-c]pyridine-5,3'-pyrrolo[3,4-c]pyridin]-1'-amine;

(S)-1-fluoro-7-(2-fluoropyridin-3-yl)-3-(2-fluoropyridin-4-yl)spiro[chromeno[2,3-c]pyridine-5,3'-pyrrolo[3,4-c]pyridin]-1'-amine;

(R)-1-fluoro-7-(2-fluoropyridin-3-yl)-3-(2-fluoropyridin-4-yl)spiro[chromeno[2,3-c]pyridine-5,3'-pyrrolo[3,4-c]pyridin]-1'-amine;

1-fluoro-7-(2-fluoropyridin-3-yl)-3-(2-fluoropyridin-4-yl)spiro[chromeno[2,3-c]pyridine-5,7'-pyrrolo[3,4-b]pyridin]-5'-amine;

(S)-3-(5,6-dihydro-2H-pyran-3-yl)-1-fluoro-7-(2-fluoropyridin-3-yl)spiro[chromeno[2,3-c]pyridine-5,5'-pyrrolo[3,4-b]pyridin]-7'-amine;

(S)-3-(5,6-dihydro-2H-pyran-3-yl)-1-fluoro-7-(2-fluoropyridin-3-yl)spiro[chromeno[2,3-c]pyridine-5,3'-pyrrolo[3,4-c]pyridin]-1'-amine; and (S)-1-fluoro-7-(2-fluoropyridin-3-yl)-3-morpholinospiro[chromeno[2,3-c]pyridine-5,5'-pyrrolo[3,4-b]pyridin]-7'-amine In another embodiment, the invention provides the compound of Formula III, or a pharmaceutically acceptable salt thereof, selected from 3'-(5,6-dihydro-2H-pyran-3-yl)-7'-(2-fluoropyridin-3-yl)spiro[benzo[e][1,3]oxazine-4,5'-chromeno[2,3-c]pyridin]-2-amine; and 7'-(2-fluoropyridin-3-yl)-3'-(2-fluoropyridin-4-yl)spiro[benzo[e][1,3]oxazine-4,5'-chromeno[2,3-c]pyridin]-2-amine;

3'-(2-fluoropyridin-4-yl)-7'-(pyrimidin-5-yl)spiro[benzo[e][1,3]oxazine-4,5'-chromeno[2,3-c]pyridin]-2-amine;

3-chloro-7-(2-fluoropyridin-3-yl)spiro[chromeno[2,3-c]pyridine-5,4'-pyrido[2,3-e][1,3]oxazin]-2'-amine;

7-(2-fluoropyridin-3-yl)-3-(2-fluoropyridin-4-yl)spiro[chromeno[2,3-c]pyridine-5,4'-pyrido[2,3-e][1,3]oxazin]-2'-amine;

3'-(2-fluoropyridin-4-yl)-7'-(pyridin-3-yl)spiro[benzo[e][1,3]oxazine-4,5'-chromeno[2,3-c]pyridin]-2-amine; and 7-(2-fluoropyridin-3-yl)-3-(2-fluoropyridin-4-yl)spiro[chromeno[2,3-c]pyridine-5,4'-pyrido[3,2-e][1,3]oxazin]-2'-amine All of the possible embodiments described herein for various of the R groups of the compounds of Formula I may be applied, as appropriate, to compounds of Formulas II and III, and any sub-formulas thereof.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the invention described herein.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having α to β number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from α and β. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from $\alpha$ and $\beta$. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "cycloalkenyl", when used alone or in combination, means a cycloalkyl containing one, two or even three rings in a structure having at least one carbon-carbon double bond in the structure, typically in the ring at the point of attachment. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom memberd or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring sytems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas I-A and I-B. Similar with Formulas II and III, in that they include sub-formulas where described.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-III. A "pharmaceutically-acceptable prodrug" as used herein, denotes a prodrug which is pharmaceutically acceptable. Pharmaceutically acceptable modifications to the compounds of Formula I-III are readily appreciated by those of ordinary skill in the art.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-III. The compounds of Formulas I-III can be synthesized according to the procedures described in the following Schemes 1, 2, 3a, 3b, 4 and 5, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1)iodide
DCC—dicyclohexylcarbodiimide
DIC—1,3-diisopropylcarbodiimide
DIEA, DIPEA—diisopropylethylamine
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$-hydrogen (gas)
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen (gas)
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light

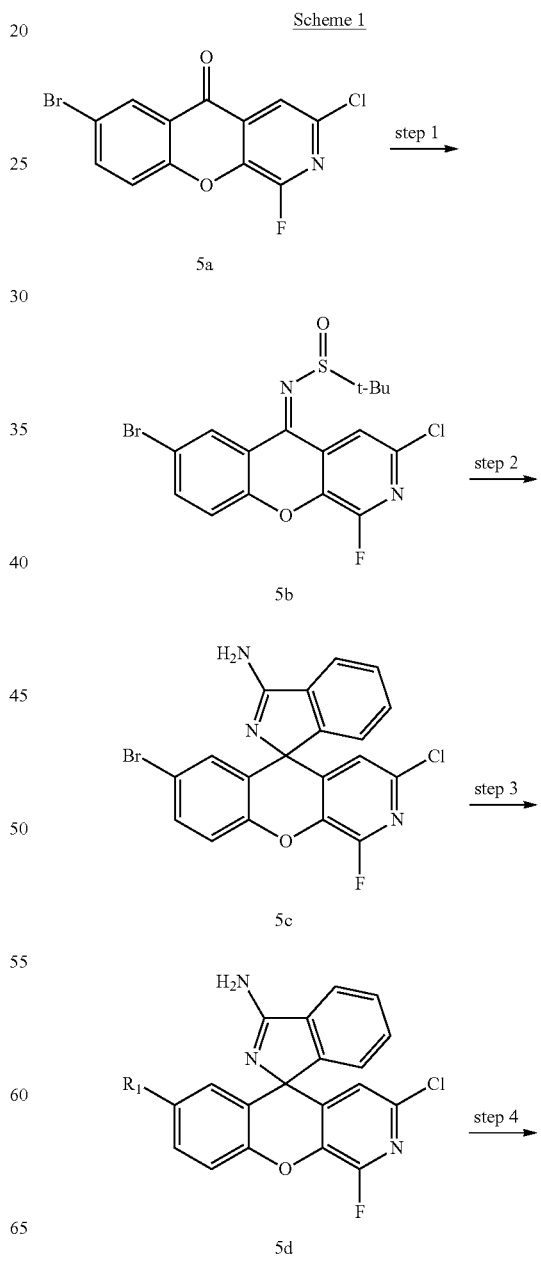

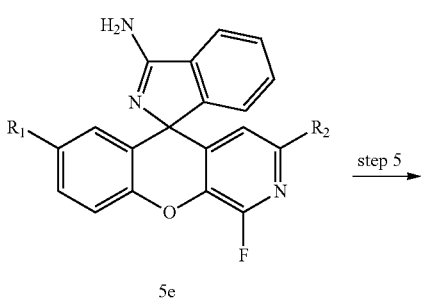

5e

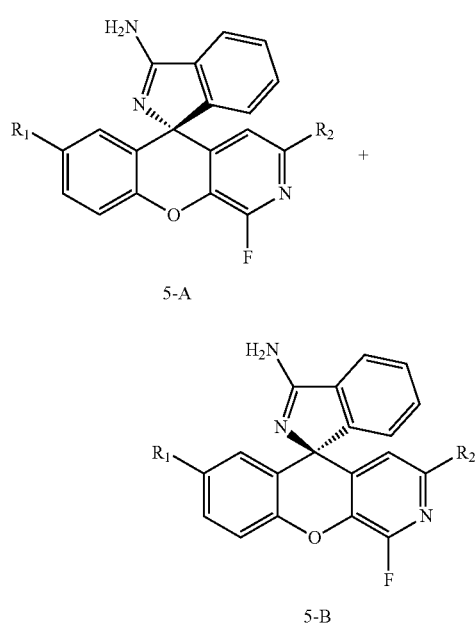

5-A

+

5-B

Scheme 1 describes an exemplary method for preparing compounds 5-A and 5-B of Formulas I-III, wherein W, X, Y and Z are each $CH_2$, each of $A^1$, $A^2$, $A^5$ and $A^6$ is $CR^6$, $CR^5$, $CR^1$ and $CR^8$, wherein $R^1$, $R^5$, $R^6$ and $R^8$ are each H, respectively, and $A^3$ is CF and $A^4$ is N. Compound 5a may be prepared by many methods, such as the one described herein in Example 4. The ketone of xanthene 5a can be converted to the corresponding spiro amino-isoindole 5c as shown under suitable conditions, such as those described in Example 5 hereinbelow. Bromo-intermediate 5c (where $R^7$ is a desired group) can be converted to desired $R^7$ adducts 5d via coupling at the site of the bromide, such as by a Suzuki or Suzuki-like aromatic-halogen exchange, which reaction generally employs a boronic acid moiety, a palladium catalyst reagent and a base.

Alternatively, the ketone intermediate 5a may be functionlized with the desired $R^7$ group via a Suzuki or Suzuki-like coupling reaction, as discussed further herein, to provide the corresponding $R^7$ intermediate (not shown). The ketone of intermediate this intermediate may then be converted to the corresponding amino iso-indole product 5d using the conditions discussed above.

The boronic ester intermediates utilized in steps 3 and/or 4 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be purchased commercially from vendor catalogs, or specially made by the vendor or by persons of ordinary skill in the art.

The Suzuki method is a reaction using a borane reagent, such as a boronic acid 7 or ester such as a dioxaborolane (see pages 81-82 herein), and a suitable leaving group containing reagent, such as the Br-xanthene 5c or chloro-xanthene 5d (bromides and chlorides are suitable halogen leaving groups "LG"). As appreciated to one of ordinary skill in the art, Suzuki reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or chloride. Chloro-pyridyl rings (where $A^1$=N) undergo Suzuki reactions in the presence of Pd catalysts. Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular bromide 5c and/or boronic acid or ester 7 (see pgs 81-82), as appreciated by those skilled in the art. In addition, where the bromide is an aromatic moiety, such as phenyl, the reaction may be complete in a short period of time with heat.

Other coupling methods are known. For example metal catalyzed coupling chemistry, such Stille, Kumada, Negishi coupling methods, and the like, may be employed to the xanthene cores 5c and/or 5d to prepare desired cyclic products 5e. In addition, compounds may possess groups which may need to be protected (and later deprotected), such as a free amino group, to carry out effective coupling reactions to install either $R^2$ or $R^7$ groups to afford the final desired compounds 5-A and 5-B, as appreciated by persons of ordinary skill in the art.

Scheme 2

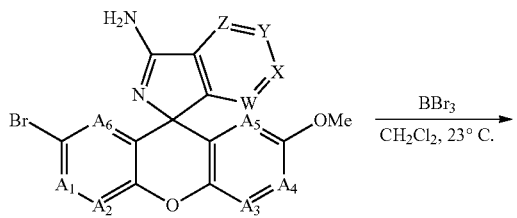

9

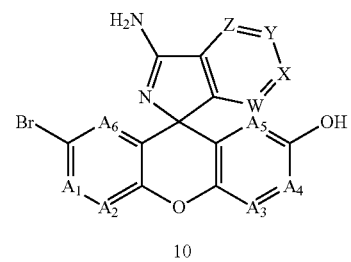

10

-continued

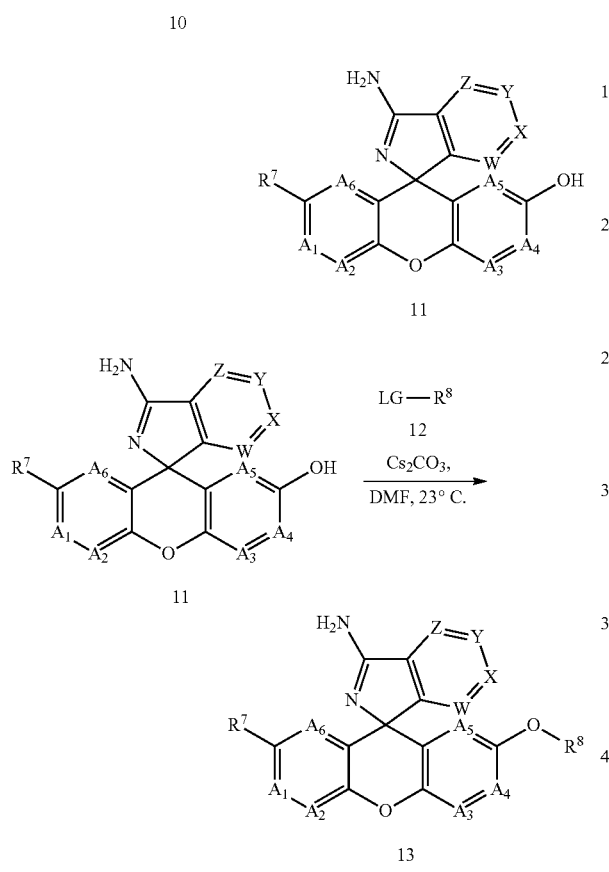

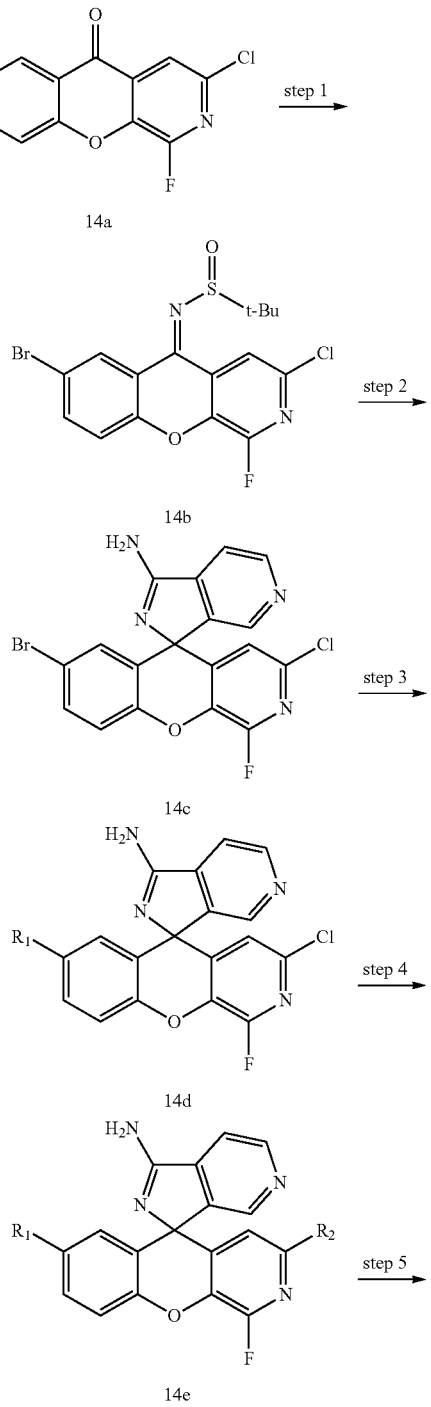

range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

Desired compounds 13 of Formula I, and sub-formulas thereof, II and III, wherein the $R^2$ group is —$OR^8$ may be made as generally described in Scheme 2. As shown, bromomethoxy intermediate 9 can be O-d-methylate using known reagents, such as borontribromide to afford the alcohol product 10. The bromide of alcohol 10 can be coupled using a suitable base to provide the desired $R^7$ group intermediate 11.

The alcohol of intermediate 11 can be functionalized as desired, such as by alkylation as shown, by reaction with an alkyl halide in the presence of a suitable base, such as cesium carbonate as shown, in suitable solvents to afford the finally desired product 13.

"LG" in this instance is a "leaving group" which may be a halide such as an iodide, bromide, chloride or fluoride. LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may

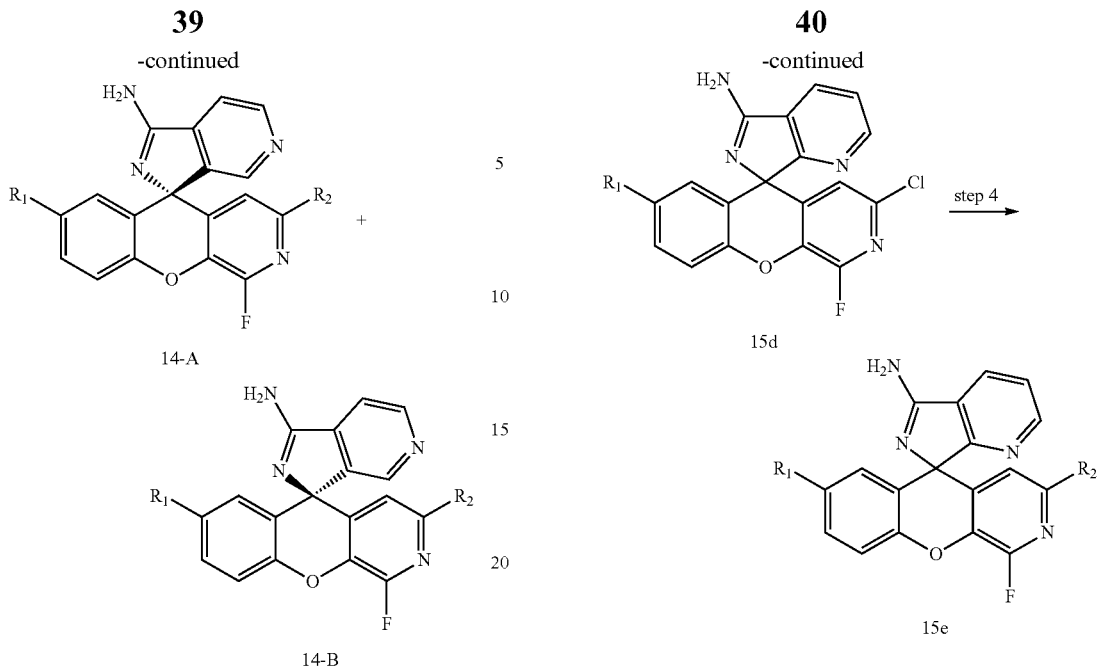

Desired compounds 14-A and 14-B may be prepared in a manner similar to the compounds described in Example 5 and Scheme 1 herein. Scheme 1 and 3 provide an efficient method of preparing analogs at the $R^2$ position of Formulas I, II and III.

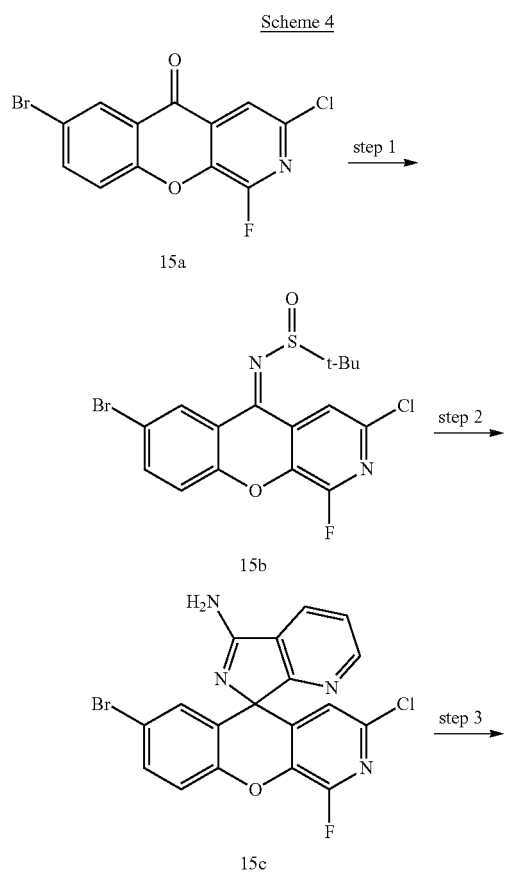

Similarly, desired compounds 15d and 15e may be prepared in a manner analogous to the compounds described in Example 5 and Schemes 1 and 3 herein.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I-III. Starting materials and intermediates used in the Examples herein may also be prepared using the procedures described in co-pending U.S. patent application Ser. No. 12/558,426, filed Sep. 11, 2009, which specification and disclosure is hereby incorporated herein by reference in its entirety. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material orconcentrate through a Biotage brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 8.0 software, available in Chem Office, or (2) by the ISIS database software (Advanced Chemistry Design Labs or ACD software).

Example 1-A

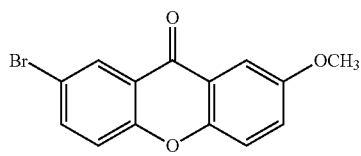 [SMILES: COc1ccc2oc3ccc(Br)cc3c(=O)c2c1]

Synthesis of 2-Bromo-7-methoxy-9H-xanthen-9-one

Step 1: 2-(4-Bromophenoxy)-5-methoxybenzoic acid

4-Bromophenol (8.7 g, 50 mmol), Cs$_2$CO$_3$ (16 g, 50 mmol), CuOTf toluene complex (2:1) (0.625 mmol, 5 mol % Cu, 150 mg), ethyl acetate (0.25 ml, 2.5 mmol) were added to a solution of 2-bromo-5-methoxybenzoic acid (11.6 g, 50 mmol) in toluene (40 mL) in a sealed tube. The reaction mixture was purged with N$_2$, and was heated to 110° C. until the aryl halide was consumed as determined by LC-MS (48 h). After cooling to rt, the mixture was filtered through a Celite plug. The Celite plug was washed with EtOAc. The mixture was acidified by 1N HCl, and extracted w/EtOAc. The combined organic phases were washed with brine, dried over anhydrous sodium sulfate, filtered, and concentrated. This residue was purified via column chromatography on silica gel (gradient elution with 0-10% MeOH/DCM) to afford 2-(4-bromophenoxy)-5-methoxybenzoic acid. MS m/z=324.9 [M+H]$^+$. Calc'd for C$_{14}$H$_{11}$BrO$_4$: 323.1.

Step 2: 2-Bromo-7-methoxy-9H-xanthen-9-one

Sulfuric acid (41 ml, 765 mmol) was added to 2-(4-bromophenoxy)-5-methoxybenzoic acid (3750 mg, 12 mmol) at RT. The reaction mixture was stirred at 60° C. for 60 min. LCMS showed complete reaction. The reaction mixture was cooled to rt and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=307.2 [M+H]$^+$. Calc'd for C$_{14}$H$_9$BrO$_3$: 305.1.

Example 1-B

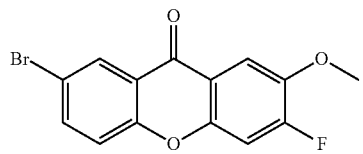 [SMILES: COc1cc2c(=O)c3cc(Br)ccc3oc2cc1F]

Synthesis of 7-Bromo-3-fluoro-2-methoxy-9H-xanthen-9-one

The titled compound was prepared using 2-bromo-4-fluoro-5-methoxybenzoic acid as the starting material, which starting material was prepared as follows:

Step 1: 4-Bromo-2-fluoro-5-methylphenol 2-fluoro-5-methylphenol (23.8 g, 0.19 mol) and bromine (9.7 ml, 0.19 mol) are combined in 50 ml of glacial acetic acid and stirred at RT for one hour. Acetic acid was removed under vacuum. The liquid was diluted with ethyl acetate and washed with water. The organic layer was washed with brine, dried over anhydrous sodium sulfate, filtered and concentrated to afford 4-bromo-2-fluoro-5-methylphenol (38 g, 98% yield) as a colorless liquid. No [M+H] peak by LCMS. 1H NMR (400 MHz, CHLOROFORM-d) ppm 1.98 (s, 1H) 2.22 (s, 3H) 6.81 (dd, J=9.15, 0.54 Hz, 1H) 7.17 (d, J=9.88 Hz, 1H)

Step 2: 1-Bromo-5-fluoro-4-methoxy-2-methylbenzene

4-Bromo-2-fluoro-5-methylphenol (40 g, 0.19 mol), cesium carbonate (75 g, 0.23 mol), and iodomethane (15 ml, 0.23 mol) were combined in 100 ml of DMF and stirred at RT for one hour (exothermic). The solution was diluted with ethyl acetate and filtered. The solution was washed with water twice, dried with anhydrous sodium sulfate, filtered, and concentrated. The product was purified via silica gel column chromatography (RediSep 330 g column) using 0-50% ethyl acetate in hexane to afford 1-bromo-5-fluoro-4-methoxy-2-methylbenzene (38 g, 89% yield) as a colorless liquid. No [M+H] peak by LCMS. $^1$H NMR (400 MHz, CHLOROFORM-d) δ ppm 2.24 (s, 3H) 3.76 (s, 3H) 6.73 (d, J=8.80 Hz, 1H) 7.13 (d, J=10.56 Hz, 1H)

Step 3: 2-Bromo-4-fluoro-5-methoxybenzoic acid

Potassium permanganate (53 g, 3.4 mol) was added to a solution of 1-bromo-5-fluoro-4-methoxy-2-methylbenzene (37 g, 1.7 mol) in 75 ml of pyridine and 150 ml of water at 60° C. The solution was stirred at 60° C. degrees for 24 hours. The solution was filtered and the solids were washed with a solution of water/methanol (50:50). The filtrate was concentrated to approximately 100 ml, then acidified (pH 1) with concentrated HCl. The solid was collected by filtration and dried under vacuum to afford 2-bromo-4-fluoro-5-methoxybenzoic acid as an off white solid. MS m/z=248.9 [M+H].

Step 4: 7-Bromo-2-fluoro-3-methoxy-9H-xanthen-9-one

Sulfuric acid (41 ml, 765 mmol) was added to 2-bromo-4-fluoro-5-methoxybenzoic acid (3.75 g, 12 mmol) at RT. The reaction mixture was stirred at 60° C. for 60 min. LCMS showed complete reaction. The reaction mixture was cooled to rt and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=326.2 [M+H]+. Calc'd for $C_{14}H_9BrO_3$: 325.1.

Example 2

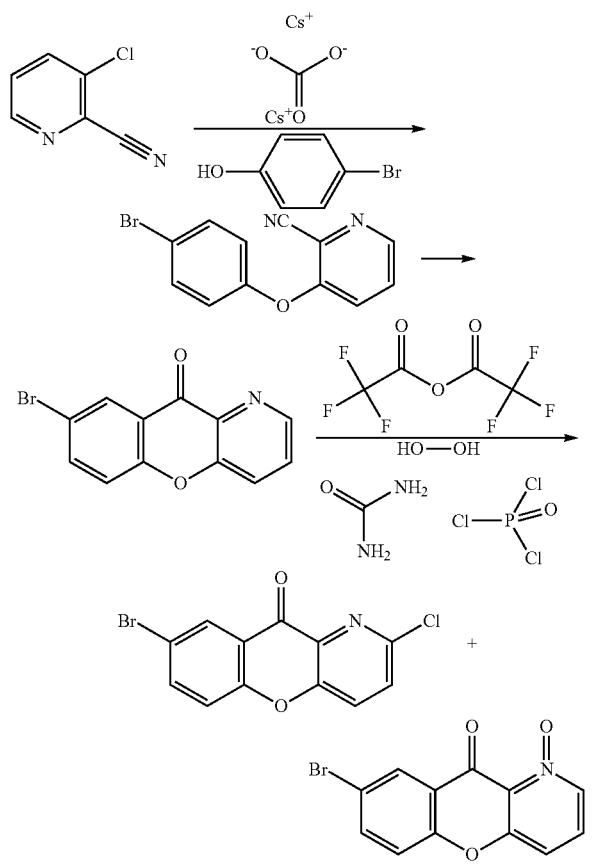

Synthesis of 8-Bromo-2-chloro-10H-chromeno[3,2-b]pyridin-10-one

Step 1

A RBF was charged with 3-chloro-2-cyanopyridine (40 g, 289 mmol), 4-bromophenol (49.9 g, 289 mmol) and cesium carbonate (113 g, 346 mmol). The reactants were suspended in 50 mL of DMSO and allowed to stir at 85 C overnight. The reaction was cooled to RT and 600 mL of water was added to it. The reaction was filtered and the solid washed with water, then air dried to provide 3-(4-bromophenoxy)-picolinonitrile as a tan solid.

Step 2

A mixture of 3-(4-bromophenoxy)-picolinonitrile (57 g, 207 mmol) and 300 g of PPA was stirred at 190° C. for 2 h, followed by 180° C. overnight. After cooling to RT, the reaction mixture was poured into 500 g of ice water. After the PH was adjusted to 7 with KOH, the suspension was filtered. The solid was washed with large excess of water, followed by washing with methanol and acetone. The resulting solid was air dried to give 8-bromo-10H-chromeno[3,2-b]pyridin-10-one as a tan solid with >90% purity. The material was carried on to the next step.

Step 3

To a solution of 8-bromo-10H-chromeno[3,2-b]pyridin-10-one (60 g, 217 mmol) and urea peroxide (42.9 g, 456 mmol) in 120 mL of DCM at 0° C. was added dropwise trifluoroacetic anhydride (63.9 mL, 456 mmol). The resulting reaction was stirred for 2 h. The reaction was quenched with 10% $Na_2S_2O_3$, extracted with DCM, dried over $Na_2SO_4$ and evaporated to dryness to give crude 8-bromo-10-oxo-10H-chromeno[3,2-b]pyridine 1-oxide as a pale yellow solid.

Step 4

To a suspension of 8-bromo-10-oxo-10H-chromeno[3,2-b]pyridine 1-oxide in 100 mL of toluene at 0° C. was added dropwise phosphorus oxychloride (35.8 mL, 391 mmol) followed by 2 mL of DMF and the mixture was stirred at RT overnight. The solvent was evaporated under vacuum and the residue which crashed out of water, was filtered and washed with water, methanol and acetone in sequence. The solid was air dried to give 8-bromo-2-chloro-10H-chromeno[3,2-b]pyridin-10-one as a tan solid.

Example 3

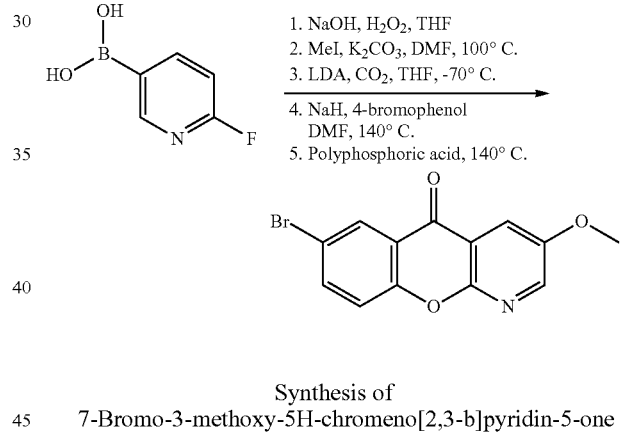

Synthesis of 7-Bromo-3-methoxy-5H-chromeno[2,3-b]pyridin-5-one

Step 1:

A three neck 3-L flask equipped with an overhead stirred was charged with 6-fluoropyridin-3-ylboronic acid (105 g, 745 mmol) and 1 L of THF. The mixture was cooled to 0° C. and NaOH 6N (373 mL, 2235 mmol) was added. To the resulting mixture was added hydrogen peroxide 30% (126 mL, 4098 mmol), dropwise via an addition funnel over the course of 30 minutes. After stirring at 0° C. for 2 hours the mixture was removed from the ice bath and maintained at RT for 30 minutes. The reaction was acidified to pH 7 with 6 N HCl (ca. 300 mL) and diluted with 500 mL of ether. The aqueous layer was extracted with ether (2×1 L) and the combined organic layers were washed with water (1.5 L) then brine before being dried over sodium sulfate. Filtration and concentration provided a white solid that was dried on high vac overnight to provide 6-fluoropyridin-3-ol.

Step 2:

To a solution of 6-fluoropyridin-3-ol (75 g, 663 mmol) in DMF (265 mL, 663 mmol) were added potassium carbonate (59.7 g, 995 mmol) and iodomethane (108 g, 763 mmol). The resulting slurry was heated at 100° C. for 3 hours. The reaction was diluted with water (1000 mL) and poured into a separatory funnel containing diethyl ether (1000 mL). The layers were separated and the aqueous layer was extracted with diethyl ether (4×500 mL). The combined organic layers were washed with water and then brine, dried over sodium sulfate, filtered and concentrated in vacuo to provide a yellow oil. This oil was diluted with 500 mL of DCM and concentrated to provide a yellow oil with a large amount of an off white precipitate. The mixture was filtered and the derived solid was washed well with DCM. The filtrate was concentrate to provide a mixture consisting of a yellow oil and an off white solid. The solid eas filtered, washing with DCM. Repeat this procedure again and then concentrated the filtrate to provide a yellow oil. The oil was taken up in 100 mL of ether and flashed through a plug of silica gel with 10:1 hexanes:ether to provide 2-fluoro-5-methoxypyridine as a yellow oil.

Step 3:

To a solution of DIPA (54.0 mL, 385 mmol) in THF (1101 mL, 385 mmol) at −60° C. was added BuLi, 2.5 M in hexanes (154 mL, 385 mmol) over 5 minutes such that the internal temperature was maintained below −60° C. After stirring for 45 minutes at −65° C. a solution of 2-fluoro-5-methoxypyridine (49 g, 385 mmol) in 200 mL of THF was added over the course of 2 minutes maintaining an internal temperature <−65° C. The reaction was stirred at −70° C. for 1.5 hours then reaction was poured into a 3 L flask containing 1200 g of crushed dry ice. The reaction was allowed to warm to 0° C. and then poured into 1000 mL of water. The organics were removed under reduced pressure and the aqueous layer was acidified with 1100 mL of 2 N HCl. The resulting thick white slurry was stirred for 1 hour then filtered to provide 2-fluoro-5-methoxynicotinic acid as a white solid.

Step 4:

To a slurry of sodium hydride (60% dispersion) (21.74 g, 543 mmol) in DMF (351 mL, 175 mmol) at 0° C. was added 4-bromophenol (60.7 g, 351 mmol) over the course of 5 minutes. Stirred at 0° C. for two minutes then removed from the ice bath and stirred for an additional 5 minutes at room temperature. Added 2-fluoro-5-methoxynicotinic acid (30 g, 175 mmol) portionwise over 10 minutes and heated the resulting slurry at 140° C. After cooling to room temperature the mixture was then poured onto 1 kg of ice and was quenched with acetic acid (50.2 mL, 877 mmol) and then 75 mL of 6 N HCl. Stirred vigorously for 1 hour, leading to the formation of a red slurry containing a very fine white precipitate. Filtered the slurry to provide 2-(4-bromophenoxy)-5-methoxynicotinic acid.

Step 5:

A 2 L flask charged with polyphosphoric acid (115% $H_3PO_4$) (300 g, 89 mmol) was heated to 140° C. at which point 2-(4-bromophenoxy)-5-methoxynicotinic acid (29 g, 89 mmol) was introduced. The thick viscous mixture is slowly stirred while heating at 140° C. After heating for 2.5 hours the solution was cooled to 100° C. and then poured onto 1 kg of ice, leading to the formation of a yellow taffy mixture. The slurry was vigorously stirred for 1 hour leading to the formation of a fine white precipitate. Filtration of this mixture proceeded slowly to provide an off white solid. This solid was washed well with DCM. The filtrate, which contained the desired product, was washed with brine and concentrated to provide 7-bromo-3-methoxy-5H-chromeno[2,3-b]pyridin-5-one as an off-white solid.

Example 4

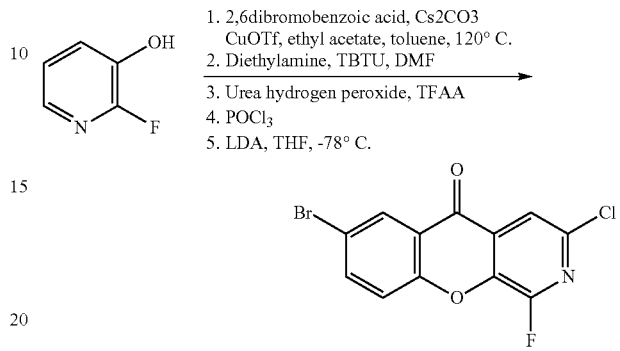

Synthesis of 7-Bromo-3-chloro-1-fluoro-5H-chromeno[2,3-c]pyridin-5-one

Step 1:

A 500 mL RBF was charged with 2-fluoro-3-hydroxypyridine (3487 mg, 30.8 mmol), 2,5-dibromobenzoic acid (8630 mg, 30.8 mmol), copper (I) trifluoromethanesulfonate toluene complex (2:1) (399 mg, 0.771 mmol) and cesium carbonate (2.01E+04 mg, 61.7 mmol). To this was added 100 mL of toluene and the mixture was azeotroped to remove about 20 mL of toluene under reduced pressure. Reaction mixture was then flushed with N2 and was heated to 120° C. for 2 hours. LC-MS analysis showed formation of the desired product along with significant impurities. The reaction mixture was cooled to RT and concentrated to give a gummy residue. The residue was taken up in ethyl acetate (100 mL) and water (75 mL). The aqueous layer was neutralized with 1N HCl to pH~2.0-3.0. The aqueous layer was extracted with ethyl acetate (2×150 mL), separated, dried over anhydrous sodium sulfate, and concentrated to yield the crude product as a brown solid which was used directly in the next step.

Step 2:

A mixture of crude 5-bromo-2-(2-fluoropyridin-3-yloxy)benzoic acid (8.00 g, 25.6 mmol), diethylamine (6.63 mL, 64.1 mmol) and TBTU (8.23 g, 25.6 mmol) in 8 mL of DMF was stirred overnight. The reaction was quenched with Sat. NaHCO3, extracted with EA/H=2:1, washed with brine, dried over Na2 SO4, filtered and evaporated to dryness. CC (DCM to DCM/EA 100:5 to 100:10 to 100:20 to 3:1) gave 5-bromo-N,N-diethyl-2-(2-fluoropyridin-3-yloxy)benzamide as a yellow solid.

Step 3:

To a solution of 5-bromo-N,N-diethyl-2-(2-fluoropyridin-3-yloxy)benzamide (1.4 g, 3.81 mmol) and urea peroxide (1.076 g, 11.44 mmol) in 10 mL of DCM at 0 C was added dropwise trifluoroacetic anhydride (1.601 mL, 11.44 mmol) and the resulting reaction was stirred overnight. LCMS showed only less than 50% of desired conversion. The mixture was evaporated to dryness, quenched with Sat. NaHCO3, extracted with EA, dried over $Na_2SO_4$, filtered and evaporated to dryness. CC (DCM to DCM/EA=3:1 to DCM/MeOH=100:2 to 100:5 to 100:10) gave 3-(4-bromo-2-(diethylcarbamoyl)phenoxy)-2-fluoropyridine 1-oxide as an off white solid.

Step 4:

To a solution of 3-(4-bromo-2-(diethylcarbamoyl)phenoxy)-2-fluoropyridine 1-oxide (420 mg, 1.096 mmol) in 15 mL of DCM was added dropwise phosphorus oxychloride (301 µL, 3.29 mmol) followed by 2 drops of DMF. After stirring at rt for 1 h, the reaction was quenched with sat. NaHCO$_3$, extracted with EA, dried over Na2SO4, filtered and evaporated to dryness. CC (DCM to DCM/EA=10:1 to 5:1 to 3:1) gave 5-bromo-2-(6-chloro-2-fluoropyridin-3-yloxy)-N,N-diethylbenzamide as a colorless gum.

Step 5:

To a solution of 5-bromo-2-(6-chloro-2-fluoropyridin-3-yloxy)-N,N-diethylbenzamide (120 mg, 0.299 mmol) in 5 mL of dry THF at −78 C was added dropwise lithium diisopropylamide, 2.0m heptane/tetrahydrofuran/ethylbenzene (158 µL, 1.195 mmol) (0.6 mL of 2M solution) and the reaction was stirred at −78 C for 3 h. The reaction was quenched at −78 C with sat. NH$_4$Cl and was allowed to warm up to RT. The reaction was extracted with EA, dried over Na$_2$SO$_4$, filtered and evaporated to dryness. CC (hexane to H/DCM=1:1 to DCM) gave 7-bromo-3-chloro-1-fluoro-5H-chromeno[2,3-c]pyridin-5-one as an off white solid. MS (M+1): 328.

Examples 5-A and 5-B

Method A

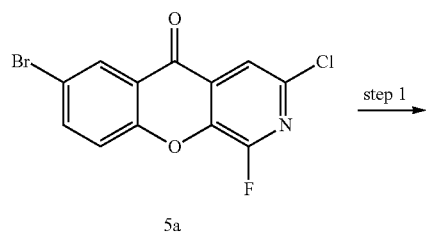

5a

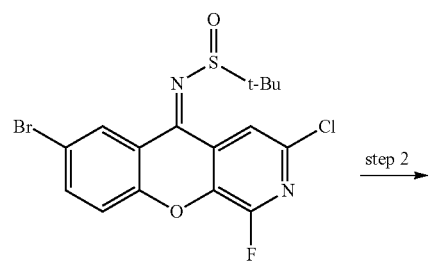

5b

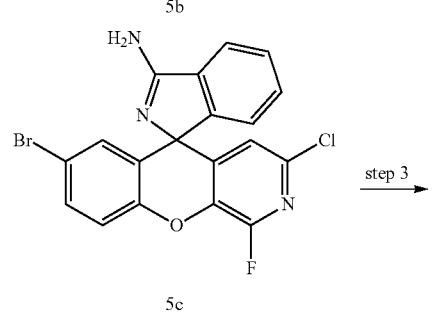

5c

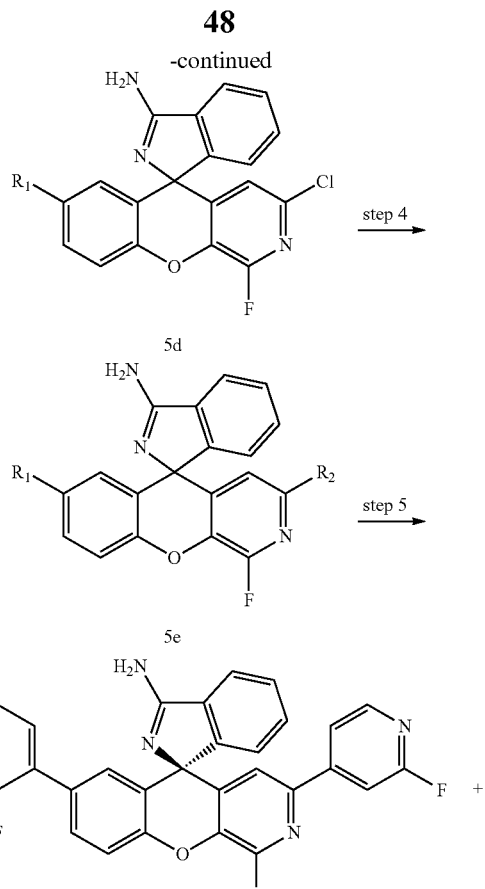

5-A

5-B

Synthesis of racemic 1-Fluoro-7-(2-fluoropyridin-3-yl)-3-(2-fluoropyridin-4-yl)spiro[chromeno[2,3-c]pyridine-5,1'-isoindol]-3'-amine 2,2,2-trifluoroacetate (5-A and 5-B)

Step 1: N-(7-bromo-3-chloro-1-fluoro-5H-chromeno[2,3-c]pyridin-5-ylidene)-2-methylpropane-2-sulfinamide (5b)

A mixture of 7-bromo-3-chloro-1-fluoro-5H-chromeno[2,3-c]pyridin-5-one (740 mg, 2.25 mmol, Example 4), 2-methyl-2-propane-sulfinamide (819 mg, 6.76 mmol, Aldrich), and tetraethoxytitanium (6.07 mL, 29.3 mmol, Aldrich) in dry THF (15 mL) was heated at 75° C. for 24 hours under nitrogen atmosphere. The mixture was cooled to RT and brine and aqueous, saturated bicarbonate solution were added while rapidly stirring. After 1 h, the resulting suspension was filtered through celite, and the filter cake was washed with EtOAc. The filtrate was washed with brine and dried over MgSO$_4$. The solvent was removed under reduced pressure and the remaining residue was purified by flash chromatography on silica gel (0-20% EtOAc/hexanes) to afford the title product as an orange solid. MS m/z=423.8 [M+H]$^+$. Calculated for C$_{16}$H$_{13}$BrClFN$_2$O$_2$S: 431.71.

Step 2: 7-Bromo-3-chloro-1-fluorospiro[chromeno [2,3-c]pyridine-5,1'-isoindol]-3'-amine (5c)

A solution of n-butyllithium (1.6 M in hexane, 0.75 mL, 1.2 mmol, Aldrich) was added dropwise to a solution of 2-bromobenzonitrile (219 mg, 1.2 mmol, Oakwood Products) in THF (30 mL) at −78° C. under nitrogen atmosphere. The reaction mixture was allowed to stir for 5 min at −78° C. Subsequently, a solution of N-(7-bromo-3-chloro-1-fluoro-5H-chromeno[2,3-c]pyridine-5-ylidene)-2-methylpropane-2-sulfinamide (400 mg, 0.93 mmol, step 1) in THF (30 mL) was added. After 5 min, the reaction mixture was quenched with aqueous, saturated solution of NH$_4$Cl and EtOAc was added. The organic phase was separated and dried over MgSO$_4$. The solvent was removed under reduced pressure and the residue was purified by flash chromatography on silica gel (55-100% EtOAc/hexanes) to afford the title compound as a yellow solid. MS m/z=431.9 [M+H]$^+$. Calculated for C$_{19}$H$_{10}$BrClFN$_3$O: 430.7.

Step 3: 3-Chloro-1-fluoro-7-(2-fluoropyridin-3-yl) spiro[chromeno[2,3-c]pyridine-5,1'-isoindol]-3'-amine 2,2,2-trifluoroacetate (5d)

A microwave vial was charged with 7-bromo-3-chloro-1-fluorospiro[chromeno[2,3-c]pyridine-5,1'-isoindol]-3'-amine HCl (200 mg, 0.428 mmol, step 2), 2-fluoropyridin-3-ylboronic acid (66 mg, 0.471 mmol, Aldrich), bis[di-tert-butyl(4-dimethylaminophenyl)phosphine]dichloropalladium(II) (30 mg, 0.043 mmol, Aldrich) and potassium phosphate (273 mg, 1.28 mmol, Aldrich). The vial was evacuated and backfilled with N$_2$ gas (2×). Dioxane (1.8 mL) and water (0.6 mL) were added and the reaction mixture was purged for 1 min with nitrogen. The vial was heated in the microwave for 30 min at 100° C. The organic phase was separated. The solvent was removed under reduced pressure and the residue was purified by reversed-phase preparative HPLC using a Phenomenex Gemini column, 10 micron, C18, 110 Å, 100×50 mm, 0.1% TFA in CH$_3$CN/H$_2$O, gradient 10% to 100% over 20 min to provide the title compound (116 mg, 48.3% yield) as a white solid. MS m/z=446.9 [M+H]$^+$. Calculated for C$_{24}$H$_{13}$ClF$_2$N$_4$O.C$_2$HF$_3$O$_2$: 560.86 (TFA salt). $^1$H-NMR (300 MHz, MeOH) ppm 6.99 (s, 1H) 7.13 (s, 1H) 7.35 (ddd, J=7.27, 5.15, 1.75 Hz, 1H) 7.41 (dd, J=6.36, 1.83 Hz, 1H) 7.57-7.67 (m, 1H) 7.70-7.97 (m, 4H) 8.15 (dd, J=3.87, 0.95 Hz, 1H) 8.27 (dd, J=6.07, 1.68 Hz, 1H).

Step 4: 1-Fluoro-7-(2-fluoropyridin-3-yl)-3-(2-fluoropyridin-4-yl)spiro[chromeno[2,3-c]pyridine-5,1'-isoindol]-3'-amine 2,2,2-trifluoroacetate (5e)

A microwave vial was charged with 3-chloro-1-fluoro-7-(2-fluoropyridin-3-yl)spiro[chromeno[2,3-c]pyridine-5,1'-isoindol]-3'-amine 2,2,2-trifluoroacetate (43 mg, 0.077 mmol, step 3), 2-fluoropyridine-4-boronic acid (27.0 mg, 0.192 mmol, Aldrich), bis[di-tert-butyl(4-dimethylaminophenyl)phosphine]dichloropalladium(II) (5.43 mg, 7.67 µmol, Aldrich) and potassium phosphate (48.8 mg, 0.230 mmol, Aldrich). The vial was evacuated and backfilled with N$_2$ gas (2×). Dioxane (0.6 mL) and water (0.2 mL) were added, and the vial was heated in the microwave for 30 min at 100° C. The reaction mixture was partitioned between EtOAc and water. The organic phase was separated and the solvent was removed under reduced pressure. The residue was purified by reversed-phase preparative HPLC using a Phenomenex Gemini column, 10 micron, C18, 110 Å, 100×50 mm, 0.1% TFA in CH$_3$CN/H$_2$O, gradient 10% to 100% over 20 min to obtain the title product (23 mg, 0.037 mmol, 48.3% yield) as a light-yellow solid. MS m/z=508.1 [M+H]$^+$. Calculated for C$_{29}$H$_{16}$F$_3$N$_5$OC$_2$HF$_3$O$_2$: 621.49 (TFA salt). $^1$H-NMR (300 MHz, MeOH) δ ppm 7.14 (t, J=1.61 Hz, 1H) 7.30-7.39 (m, 1H) 7.39-7.48 (m, 1H) 7.53-7.70 (m, 3H) 7.72-7.86 (m, 4H) 7.92 (ddd, J=9.94, 7.75, 1.90 Hz, 1H) 8.16 (d, J=4.97 Hz, 1H) 8.22 (d, J=5.41 Hz, 1H) 8.26-8.37 (m, 1H).

Step 5: Chiral separation of racemic 1-Fluoro-7-(2-fluoropyridin-3-yl)-3-(2-fluoropyridin-4-yl)spiro [chromeno[2,3-c]pyridine-5,1'-isoindol]-3'-amine 2,2,2-trifluoroacetate (5-A and 5-B)

1-Fluoro-7-(2-fluoropyridin-3-yl)-3-(2-fluoropyridin-4-yl)spiro[chromeno[2,3-c]pyridine-5,1'-isoindol]-3'-amine 2,2,2-trifluoroacetate (131 mg) was chromatographed using supercritical CO$_2$ (additives 33% methanol with 20 mM NH$_3$) on a Chiralcel ODH column (21×250 mm, 5 µm) eluting at a flow rate 65 ml/min (100 bar pressure, 40° C. column temperature). The first peak (retention time=4.5 min) provided (R)-1-Fluoro-7-(2-fluoropyridin-3-yl)-3-(2-fluoropyridin-4-yl)spiro[chromeno[2,3-c]pyridine-5,1'-isoindol]-3'-amine (Example 5-A; >99% ee), and the second peak (retention time=7.5 min) provided (S)-1-Fluoro-7-(2-fluoropyridin-3-yl)-3-(2-fluoropyridin-4-yl)spiro[chromeno[2,3-c]pyridine-5,1'-isoindol]-3'-amine (Example 5-B; >99% ee).

$^1$H-NMR (5-A, 300 MHz, MeOH) δ ppm 7.02 (t, J=1.68 Hz, 1H) 7.22 (d, J=7.45 Hz, 1H) 7.28 (s, 1H) 7.32 (ddd, J=7.23, 5.12, 1.68 Hz, 1H) 7.42-7.57 (m, 4H) 7.58-7.69 (m, 2H) 7.86 (ddd, J=9.87, 7.67, 1.75 Hz, 1H) 7.95 (d, J=7.45 Hz, 1H) 8.11 (d, J=4.68 Hz, 1H) 8.17 (d, J=5.41 Hz, 1H).

$^1$H-NMR (5-B, 300 MHz, MeOH) δ ppm 7.01 (t, J=1.83 Hz, 1H) 7.20 (d, J=7.45 Hz, 1H) 7.25 (s, 1H) 7.33 (ddd, J=7.27, 5.15, 1.75 Hz, 1H) 7.40-7.48 (m, 2H) 7.48-7.56 (m, 2H) 7.58-7.69 (m, 2H) 7.82-7.95 (m, 2H) 8.11 (dt, J=3.07, 1.53 Hz, 1H) 8.19 (d, J=5.41 Hz, 1H).

Mass for both peaks m/z=508.1 [M+H]$^+$. Calculated for C$_{29}$H$_{16}$F$_3$N$_5$O: 507.47.

Example 6

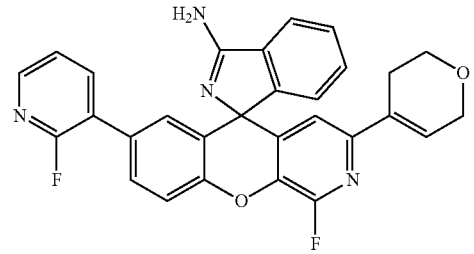 [SMILES: NC1=NC2(c3cc(-c4cccnc4F)ccc3Oc3c2cc(C2=CCOCC2)nc3F)c2ccccc21]

Synthesis of 3-(3,6-Dihydro-2H-pyran-4-yl)-1-fluoro-7-(2-fluoropyridin-3-yl)spiro[chromeno[2,3-c]pyridine-5,1'-isoindol]-3'-amine 2,2,2-trifluoroacetate The title compound (racemate) was synthesized by procedures and steps analogous to those described in Example 5 above, but using 3,6-dihydro-2H-pyran-4-ylboronic acid in step 4. MS m/z=495.2 [M+H]+. Calculated for $C_{29}H_{20}F_2N_4O_2.C_2HF_3O_2$: 608.51 (TFA salt)

$^1$H-NMR (300 MHz, MeOH) δ ppm 2.36 (br. s., 2H) 3.80 (t, J=5.41 Hz, 2H) 4.24 (d, J=2.78 Hz, 2H) 6.52-6.64 (m, 1H) 6.78 (s, 1H) 7.10 (t, J=1.68 Hz, 1H) 7.25-7.46 (m, 2H) 7.60 (d, J=8.77 Hz, 1H) 7.69-7.84 (m, 3H) 7.89 (ddd, J=9.72, 7.82, 1.90 Hz, 1H) 8.04-8.18 (m, 1H) 8.26 (dd, J=6.14, 1.90 Hz, 1H).

Example 7

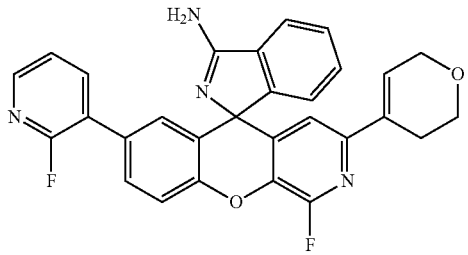 [SMILES: NC1=NC2(c3cc(-c4cccnc4F)ccc3Oc3c2cc(C2=CCOCC2)nc3F)c2ccccc21]

Synthesis of 3-(5,6-Dihydro-2H-pyran-3-yl)-1-fluoro-7-(2-fluoropyridin-3-yl)spiro[chromeno[2,3-c]pyridine-5,1'-isoindol]-3'-amine 2,2,2-trifluoroacetate The title compound (racemate) was synthesized by procedures and steps analogous to those described in Example 5 above, but using 2-(5,6-dihydro-2H-pyran-3-yl)-4,4,5,5-tetramethyl-1,3,2-dioxaborolane in step 4. MS m/z=495.0 [M+H]+.

Calculated for $C_{29}H_{20}F_2N_4O_2.C_2HF_3O_2$: 608.51 (TFA salt)

$^1$H NMR (300 MHz, MeOH) δ ppm 2.26 (br. s., 2H) 3.75 (t, J=5.48 Hz, 2H) 4.40 (d, J=1.90 Hz, 2H) 6.49-6.66 (m, 1H) 6.82 (s, 1H) 7.11 (t, J=1.90 Hz, 1H) 7.29-7.44 (m, 3H) 7.60 (d, J=8.62 Hz, 1H) 7.69-7.85 (m, 3H) 7.90 (ddd, J=9.90, 7.64, 1.90 Hz, 1H) 8.09-8.20 (m, 1H) 8.22-8.33 (m, 1H).

Examples 7-A & 7-B

Chiral separation of racemic 3-(5,6-dihydro-2H-pyran-3-yl)-1-fluoro-7-(2-fluoropyridin-3-yl)spiro[chromeno[2,3-c]pyridine-5,1'-isoindol]-3'-amine (7-A and 7-B)

3-(5,6-Dihydro-2H-pyran-3-yl)-1-fluoro-7-(2-fluoropyridin-3-yl)spiro[chromeno[2,3-c]pyridine-5,1'-isoindol]-3'-amine 2,2,2-trifluoroacetate (50 mg) was chromatographed using supercritical $CO_2$ (additives 33% methanol with 20 mM NH$_3$) on a Chrialcel ODH column (21×250 mm, 5 μm) eluting at a flow rate 65 ml/min (100 bar pressure, 40° C. column temperature). The first peak (retention time=5.25 min) provided (R)-3-(5,6-dihydro-2H-pyran-3-yl)-1-fluoro-7-(2-fluoropyridin-3-yl)spiro[chromeno[2,3-c]pyridine-5,1'-isoindol]-3'-amine (example 7-A; >99% ee), and the second peak (retention time=6.65 min) provided (S)-3-(5,6-dihydro-2H-pyran-3-yl)-1-fluoro-7-(2-fluoropyridin-3-yl)spiro[chromeno[2,3-c]pyridine-5,1'-isoindol]-3'-amine (example 7-B; >99% ee).

$^1$H-NMR (7-A, 300 MHz, MeOH) δ ppm 2.24 (br. s., 2H) 3.73 (t, J=5.48 Hz, 2H) 4.38 (d, J=1.90 Hz, 2H) 6.39-6.51 (m, 1H) 6.98 (t, J=1.75 Hz, 1H) 7.15 (d, J=7.45 Hz, 1H) 7.32 (ddd, J=7.31, 5.12, 1.75 Hz, 1H) 7.38-7.55 (m, 3H) 7.55-7.66 (m, 1H) 7.78-7.93 (m, 2H) 8.10 (ddd, J=3.11, 1.50, 1.39 Hz, 1H).

$^1$H-NMR (7-B, 300 MHz, MeOH) δ ppm 2.24 (br. s., 2H) 3.73 (t, J=5.48 Hz, 2H) 4.38 (d, J=1.90 Hz, 2H) 6.45 (t, J=4.17 Hz, 1H) 6.64 (s, 1H) 6.98 (t, J=1.75 Hz, 1H) 7.15 (d, J=7.45 Hz, 1H) 7.32 (ddd, J=7.27, 5.15, 1.75 Hz, 1H) 7.38-7.55 (m, 3H) 7.55-7.63 (m, 1H) 7.78-7.94 (m, 2H) 8.04-8.17 (m, 1H).

Mass for both peaks m/z=495.0 [M+H]+. Calculated for $C_{29}H_{20}F_2N_4O_2$: 494.49.

Example 8

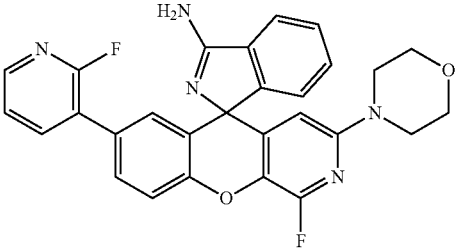 [SMILES: NC1=NC2(c3cc(-c4cccnc4F)ccc3Oc3c2cc(N2CCOCC2)nc3F)c2ccccc21]

Synthesis of 1-Fluoro-7-(2-fluoropyridin-3-yl)-3-morpholinospiro[chromeno[2,3-c]pyridine-5,1'-isoindol]-3'-amine 2,2,2-trifluoroacetate (racemic)

A microwave vial was charged with 3-chloro-1-fluoro-7-(2-fluoropyridin-3-yl)spiro[chromeno[2,3-c]pyridine-5,1'-isoindol]-3'-amine (50 mg, 0.112 mmol, step 3) and chloro (2-dicyclohexylphosphino-2',6'-di-1-propoxy-1,1'-biphenyl) [2-(2-aminoethylphenyl)]palladium(II), methyl-t-butylether adduct (8.15 mg, 0.011 mmol, Strem). The vial was evacuated and backfilled with nitrogen. Morpholine (0.012 mL, 0.134 mmol, Aldrich) and a solution of lithium bis(trimethylsilyl) amide (1.0 M in THF; 0.280 mL, 0.280 mmol) were added, followed by dioxane (1 mL). After 20 min reaction time at RT, aqueous, saturated NH$_4$Cl solution was added, followed by EtOAc. The organic phase was separated and the solvent was removed under reduced pressure. The residue was purified by reversed-phase preparative HPLC using a Phenomenex Gemini column, 10 micron, C18, 110 Å, 100×50 mm, 0.1% TFA in CH$_3$CN/H$_2$O, gradient 10% to 100% over 20 min. The reaction was run 2×, both were combined and purified to afford the titled compound (55 mg, 0.090 mmol) as a light-yellow solid.

MS m/z=497.9 [M+H]+. Calculated for $C_{28}H_{21}F_2N_5O_2.C_2HF_0O_2$: 611.52 (TFA salt)

$^1$H NMR (300 MHz, DMSO-d$_6$) δ ppm 3.25 (d, J=5.41 Hz, 4H) 3.61 (t, J=4.60 Hz, 4H) 6.18 (s, 1H) 7.11 (s, 1H) 7.33-7.46 (m, 2H) 7.57 (d, J=8.77 Hz, 1H) 7.65-7.78 (m, 3H) 7.94 (ddd, J=10.12, 7.78, 1.97 Hz, 1H) 8.19 (d, J=4.82 Hz, 1H) 8.27-8.37 (m, 1H) 9.98 (br. s., 1H) 10.28 (s, 1H) 11.46 (br. s., 1H).

Example 9

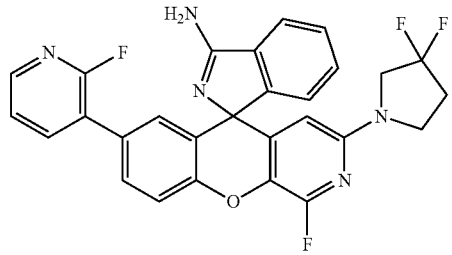 [SMILES: NC1=NC2(c3cc(-c4cccnc4F)ccc3Oc3c2cc(N2CCC(F)(F)C2)nc3F)c2ccccc21]

Synthesis of 3-(3,3-Difluoropyrrolidin-1-yl)-1-fluoro-7-(2-fluoropyridin-3-yl)spiro[chromeno[2,3-c]pyridine-5,1'-isoindol]-3'-amine 2,2,2-trifluoroacetate (racemic)

A microwave vial was charged with 3-chloro-1-fluoro-7-(2-fluoropyridin-3-yl)spiro[chromeno[2,3-c]pyridine-5,1'-isoindol]-3'-amine (50 mg, 0.112 mmol, step 3), 3,3-difluoropyrrolidine hydrochloride (24.10 mg, 0.168 mmol, Aldrich) and chloro(2-dicyclohexylphosphino-2',6'-di-1-propoxy-1,1'-biphenyl)[2-(2-aminoethylphenyl)]palladium (II), methyl-t-butylether adduct (8.15 mg, 0.011 mmol, Strem). The vial was evacuated and backfilled with nitrogen. A solution of lithium bis(trimethylsilyl)amide (1.0 M in THF; 0.280 mL, 0.280 mmol, Aldrich) was added, followed by dioxane (1 mL). After 20 min reaction time at RT, additional LiHMDS solution (0.15 mL, 0.15 mmol) was added. After additional 5 min reaction time, aqueous, saturated NH$_4$Cl solution was added, followed by EtOAc. The organic phase was separated and the solvent was removed under reduced pressure. The residue was purified by reversed-phase preparative HPLC using a Phenomenex Gemini column, 10 micron, C18, 110 Å, 100×50 mm, 0.1% TFA in CH$_3$CN/H$_2$O, gradient 10% to 100% over 20 minutes. The reaction was run 2×, both reactions were combined and purified together to afford the titled compound (53 mg, 0.084 mmol) as a yellow solid.

MS m/z=518.0 [M+H]$^+$. Calculated for C$_{28}$H$_9$F$_4$N$_5$OC$_2$HF$_0$O$_2$: 631.50 (TFA salt)

$^1$H NMR (300 MHz, DMSO-d$_6$) δ ppm 2.36-2.49 (m, 3H) 3.38-3.56 (m, 2H) 3.68 (t, J=13.08 Hz, 2H) 5.89 (s, 1H) 7.04-7.21 (m, 1H) 7.31-7.47 (m, 2H) 7.57 (d, J=8.77 Hz, 1H) 7.66-7.80 (m, 3H) 7.94 (ddd, J=10.08, 7.75, 1.90 Hz, 1H) 8.12-8.26 (m, 1H) 8.27-8.40 (m, 1H) 10.00 (br. s., 1H) 10.29 (s, 1H) 11.49 (br. s., 1H).

Examples 10, 10-C & 10-D

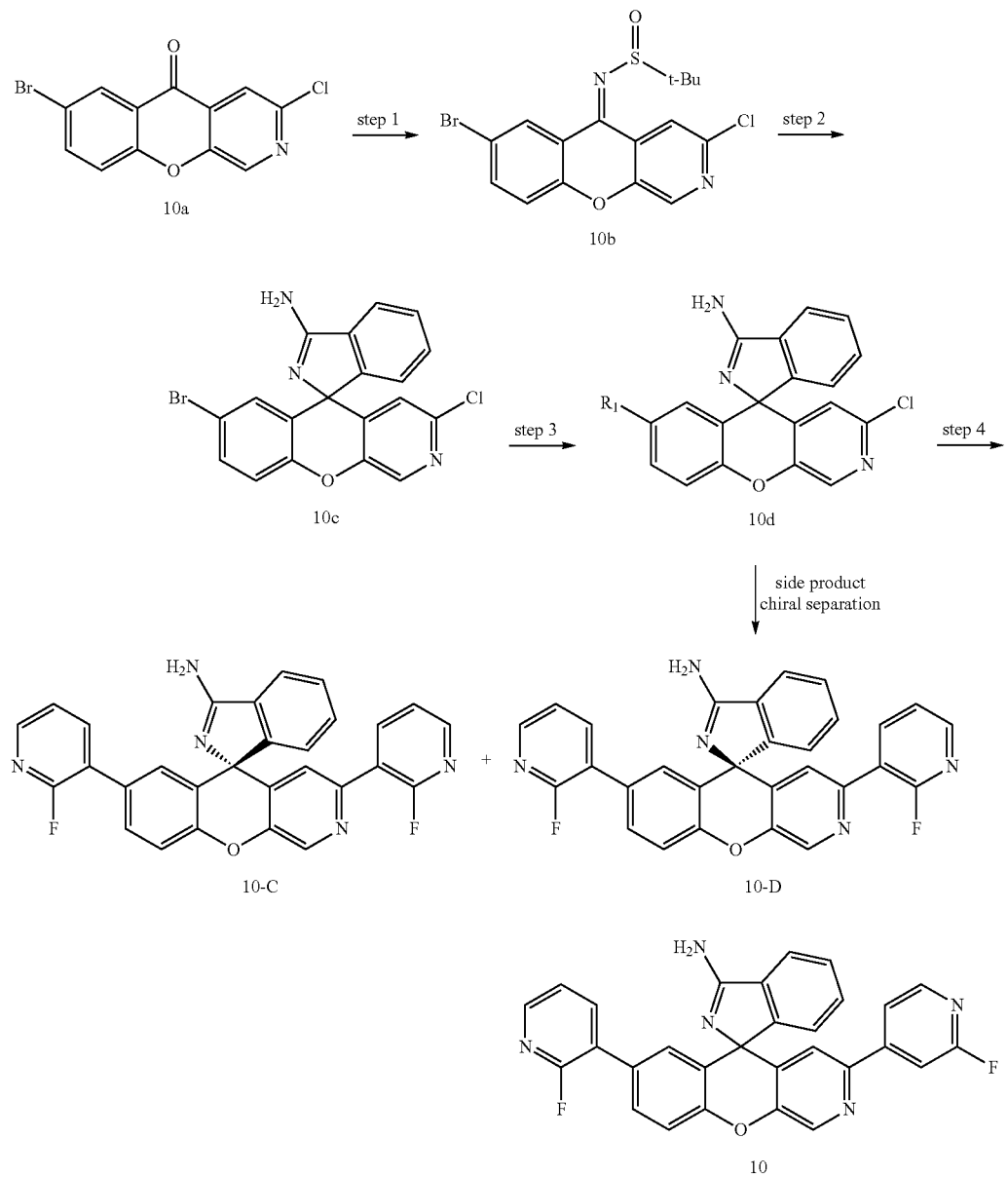

Synthesis of 7-(2-Fluoropyridin-3-yl)-3-(2-fluoropyridin-4-yl)spiro[chromeno[2,3-c]pyridine-5,1'-isoindol]-3'-amine 2,2,2-trifluoroacetate

Step 1: N-(7-bromo-3-chloro-5H-chromeno[2,3-c]pyridin-5-ylidene)-2-methylpropane-2-sulfinamide (10b)

The title compound was synthesized by procedures and steps analogous to those described in Example 5 above, but using 7-bromo-3-chloro-5H-chromeno[2,3-c]pyridin-5-one, prepared in a manner analogous to that described in Example 4.

MS m/z=415.0 [M+H]$^+$. Calculated for $C_{16}H_{14}BrClN_2O_2S$: 413.72.

Step 2: 7-Bromo-3-chlorospiro[chromeno[2,3-c]pyridine-5,1'-isoindol]-3'-amine 2,2,2-trifluoroacetate (10c; racemic)

The title compound was synthesized by procedures and steps analogous to those described in Example 5 above, but using N-(7-bromo-3-chloro-5H-chromeno[2,3-c]pyridin-5-ylidene)-2-methylpropane-2-sulfinamide in step 2.

MS m/z=411.8 [M+H]$^+$, 413.9 [M+2H]$^+$. Calculated for $C_{19}H_{11}BrClN_3O \cdot C_2HF_3O_2$: 526.69 (TFA salt)

$^1$H-NMR (400 MHz, CHLOROFORM-d) δ ppm 7.00-7.11 (m, 2H) 7.26-7.43 (m, 2H) 7.58-7.68 (m, 1H) 7.73-7.86 (m, 2H) 8.22-8.35 (m, 1H) 8.54 (s, 1H)

Step 3: 3-Chloro-7-(2-fluoropyridin-3-yl)spiro[chromeno[2,3-c]pyridine-5,1'-isoindol]-3'-amine 2,2,2-trifluoroacetate (10d; racemic)

The title compound was synthesized by procedures and steps analogous to those described in Example 5 above, but using 7-bromo-3-chlorospiro[chromeno[2,3-c]pyridine-5,1'-isoindol]-3'-amine in step 3. MS m/z=429.0 [M+H]$^+$. Calculated for $C_{24}H_{14}ClFN_4O \cdot C_2HF_3O_2$: 542.87 (TFA salt).

$^1$H-NMR (300 MHz, MeOH) δ ppm 7.04-7.20 (m, 2H) 7.29-7.42 (m, 2H) 7.58 (d, J=8.62 Hz, 1H) 7.69-7.85 (m, 3H) 7.90 (ddd, J=9.83, 7.64, 1.83 Hz, 1H) 8.08-8.20 (m, 1H) 8.21-8.33 (m, 1H) 8.59 (s, 1H).

Chiral separation of 3,7-bis(2-fluoropyridin-3-yl)spiro[chromeno[2,3-c]pyridine-5,1'-isoindol]-3'-amine (side products of Step 3)

Compound Examples 10-C and 10-D (Table 1) were obtained as a side product in the synthesis of step 3 of Example 10, isolated utilizing chiral separation conditions as described hereinabove and tested for modulatory activity against BACE.

Mass for both peaks m/z=490.9 [M+H]$^+$. Calculated for $C_{29}H_{17}F_2N_5O$: 489.47.

$^1$H-NMR (10-C; peak 1, 300 MHz, CHLOROFORM-d) δ ppm 6.68 (s, 1H) 6.75-6.89 (m, 2H) 6.97 (d, J=7.60 Hz, 1H) 7.13 (d, J=8.77 Hz, 1H) 7.34 (dd, J=8.77, 2.34 Hz, 1H) 7.43-7.65 (m, 3H) 7.96 (d, J=7.16 Hz, 2H) 8.38 (s, 1H).

$^1$H-NMR (10-D; peak 2, 300 MHz, CHLOROFORM-d) δ ppm 6.68 (s, 1H) 6.75-6.88 (m, 2H) 6.97 (d, J=7.45 Hz, 1H) 7.13 (d, J=8.77 Hz, 1H) 7.34 (dd, J=8.77, 2.34 Hz, 1H) 7.44-7.64 (m, 3H) 7.96 (d, J=7.02 Hz, 2H) 8.38 (s, 1H).

Steps 4: 7-(2-Fluoropyridin-3-yl)-3-(2-fluoropyridin-4-yl)spiro[chromeno[2,3-c]pyridine-5,1'-isoindol]-3'-amine 2,2,2-trifluoroacetate (Product 10 [racemic mixture])

The title compound was synthesized by procedures and steps analogous to those described in Example 5 above, but using 3-chloro-7-(2-fluoropyridin-3-yl)spiro[chromeno[2,3-c]pyridine-5,1'-isoindol]-3'-amine in step 4.

MS m/z=490.0 [M+H]$^+$. Calculated for $C_{29}H_{17}F_2N_5O \cdot C_2HF_3O_2$: 603.50 (TFA salt).

$^1$H-NMR (300 MHz, MeOH) δ ppm 7.09-7.20 (m, 1H) 7.28-7.45 (m, 2H) 7.52 (s, 1H) 7.59-7.68 (m, 2H) 7.69-7.87 (m, 4H) 7.92 (ddd, J=9.83, 7.64, 1.97 Hz, 1H) 8.16 (d, J=4.53 Hz, 1H) 8.22 (d, J=5.12 Hz, 1H) 8.26-8.34 (m, 1H) 8.37 (d, J=5.12 Hz, 1H) 8.92 (s, 1H).

Example 11

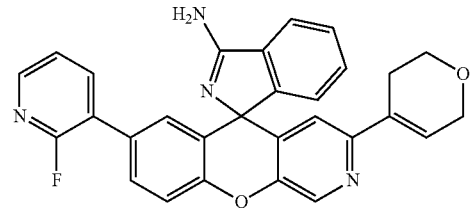 [SMILES: NC1=NC2(c3cc(-c4cccnc4F)ccc3Oc3cnc(C4=CCOCC4)cc32)c2ccccc21]

Synthesis of 3-(3,6-dihydro-2H-pyran-4-yl)-7-(2-fluoropyridin-3-yl)spiro[chromeno[2,3-c]pyridine-5,1'-isoindol]-3'-amine 2,2,2-trifluoroacetate (racemic)

The title compound was synthesized by procedures and steps analogous to those described in Example 5 above, but using 3-chloro-7-(2-fluoropyridin-3-yl)spiro[chromeno[2,3-c]pyridine-5,1'-isoindol]-3'-amine and 3,6-dihydro-2H-pyran-4-ylboronic acid in step 4.

MS m/z=477.0 [M+H]$^+$. Calculated for $C_{29}H_{21}FN_4O_2 \cdot C_2HF_3O_2$: 590.52 (TFA salt).

$^1$H-NMR (400 MHz, MeOH) δ ppm 2.45 (dd, J=5.38, 1.86 Hz, 2H) 3.84 (t, J=5.48 Hz, 2H) 4.25 (q, J=2.74 Hz, 2H) 6.44-6.55 (m, 1H) 6.97 (s, 1H) 7.12 (s, 1H) 7.28-7.41 (m, 2H) 7.57 (d, J=8.61 Hz, 1H) 7.69-7.84 (m, 3H) 7.91 (ddd, J=9.83, 7.68, 1.86 Hz, 1H) 8.14 (d, J=4.30 Hz, 1H) 8.20-8.32 (m, 1H) 8.70 (s, 1H).

Example 12

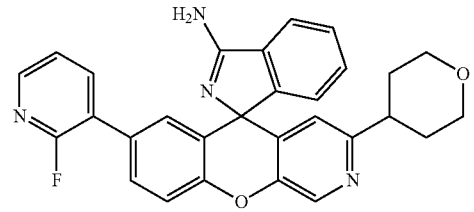 [SMILES: NC1=NC2(c3cc(-c4cccnc4F)ccc3Oc3cnc(C4CCOCC4)cc32)c2ccccc21]

Synthesis of 7-(2-Fluoropyridin-3-yl)-3-(tetrahydro-2H-pyran-4-yl)spiro[chromeno[2,3-c]pyridine-5,1'-isoindol]-3'-amine 2,2,2-trifluoroacetate (racemic)

A flask containing a solution of 3-(3,6-dihydro-2H-pyran-4-yl)-7-(2-fluoropyridin-3-yl)spiro[chromeno[2,3-c]pyridine-5,1'-isoindol]-3'-amine 2,2,2-trifluoroacetate (30 mg, 0.051 mmol) and MeOH (4 mL) was evacuated and backfilled with nitrogen. Pd/C (10 weight %, 100 mg, Aldrich) was added and the flask was evacuated and backfilled with $H_2$ gas. The flask was fitted with a balloon filled with $H_2$ gas (1 atm) and the reaction mixture was stirred at RT for 3 h. The reaction mixture was filtered through a pad of celite and the celite was washed with EtOAc. The solvent was removed under reduced pressure and the remaining residue was purified by reversed-phase preparative HPLC using a Phenomenex Gemini column, 10 micron, C18, 110 Å, 100×50 mm, 0.1% TFA in $CH_3CN/H_2O$, gradient 10% to 100% over 20 min to obtain the title compound (7.8 mg, 25.9%) as a white solid.

MS m/z=479.1 [M+H]$^+$. Calculated for $C_{29}H_{23}FN_4O_2C_2HF_3O_2$: 592.54 (TFA salt).

$^1$H-NMR (400 MHz, MeOH) δ ppm 1.57-1.86 (m, 4H) 2.82-2.96 (m, 1H) 3.48 (t, J=12.62 Hz, 2H) 3.90-4.04 (m, 2H) 6.83 (s, 1H) 7.11 (s, 1H) 7.28-7.41 (m, 2H) 7.57 (d, J=8.61 Hz, 1H) 7.69-7.83 (m, 3H) 7.84-7.96 (m, 1H) 8.14 (d, J=4.30 Hz, 1H) 8.21-8.32 (m, 1H) 8.68 (s, 1H).

Example 13

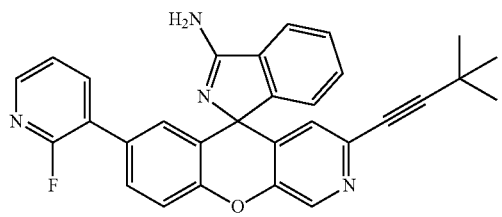 [SMILES: CC(C)(C)C#Cc1cc2c(cn1)Oc1ccc(-c3cccnc3F)cc1C21N=C(N)c2ccccc21]

Synthesis of 3-(3,3-Dimethylbut-1-ynyl)-7-(2-fluoropyridin-3-yl)spiro[chromeno[2,3-c]pyridine-5,1'-isoindol]-3'-amine 2,2,2-trifluoroacetate (racemic)

A microwave vial was charged with 3-chloro-7-(2-fluoropyridin-3-yl)spiro[chromeno[2,3-c]pyridine-5,1'-isoindol]-3'-amine (0.05 g, 0.117 mmol, example 4d), cesium carbonate (0.100 g, 0.30 mmol, Aldrich), dichlorobis(acetonitrile)palladium(II) (3.02 mg, 0.012 mmol, Aldrich), and dicyclohexyl (2',4',6'-triisopropylbiphenyl-2-yl)phosphine (0.017 g, 0.035 mmol, Aldrich). The vial was evacuated and backfilled with $N_2$ gas (2×). ACN (0.5 mL) was added and the yellow suspension was stirred at RT for 25 min. 3,3-Dimethylbut-1-yne (0.036 mL, 0.29 mmol, Aldrich) was added and the reaction mixture was placed in a preheated oilbath (90° C.). The reaction mixture was heated to 90° C. overnight. The solvent was removed under reduced pressure and the residue was purified by reversed-phase preparative HPLC using a Phenomenex Gemini column, 10 micron, C18, 110 Å, 100×50 mm, 0.1% TFA in $CH_3CN/H_2O$, gradient 10% to 100% over 20 min to obtain the title compound as light-yellow solid.

MS m/z=475.1 [M+H]$^+$. Calculated for $C_{30}H_{23}FN_4O.C_2HF_3O_2$: 588.55 (TFA salt)

$^1$H-NMR (300 MHz, MeOH) δ ppm 1.27 (s, 9H) 6.98 (s, 1H) 7.11 (t, J=1.83 Hz, 1H) 7.28-7.41 (m, 2H) 7.58 (d, J=8.62 Hz, 1H) 7.69-7.85 (m, 3H) 7.90 (ddd, J=9.87, 7.67, 1.90 Hz, 1H) 8.14 (d, J=4.68 Hz, 1H) 8.22-8.33 (m, 1H) 8.65 (br. s., 1H).

Examples 14c-1, 14c-2, 14-A & 14-B

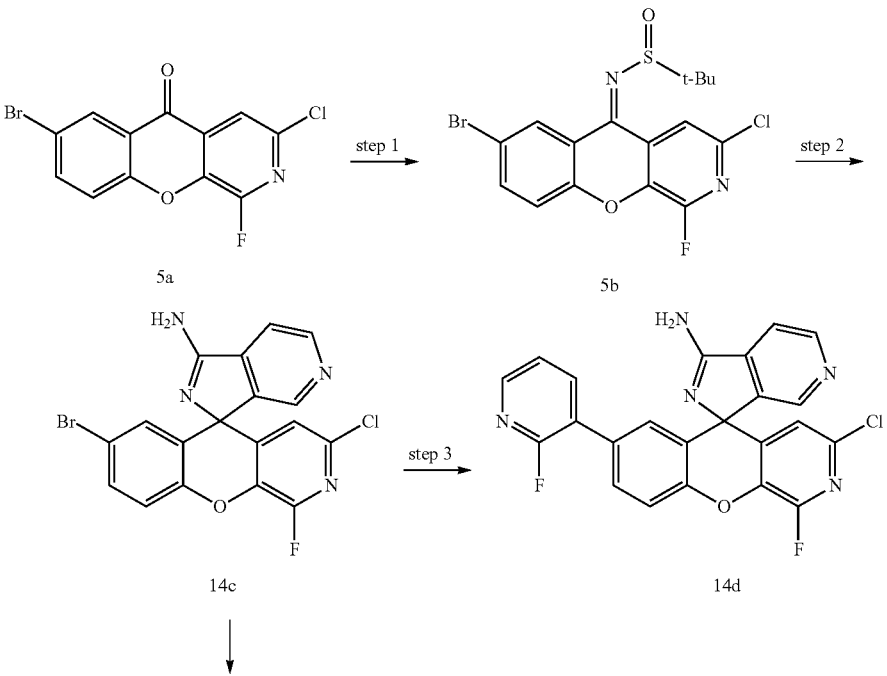

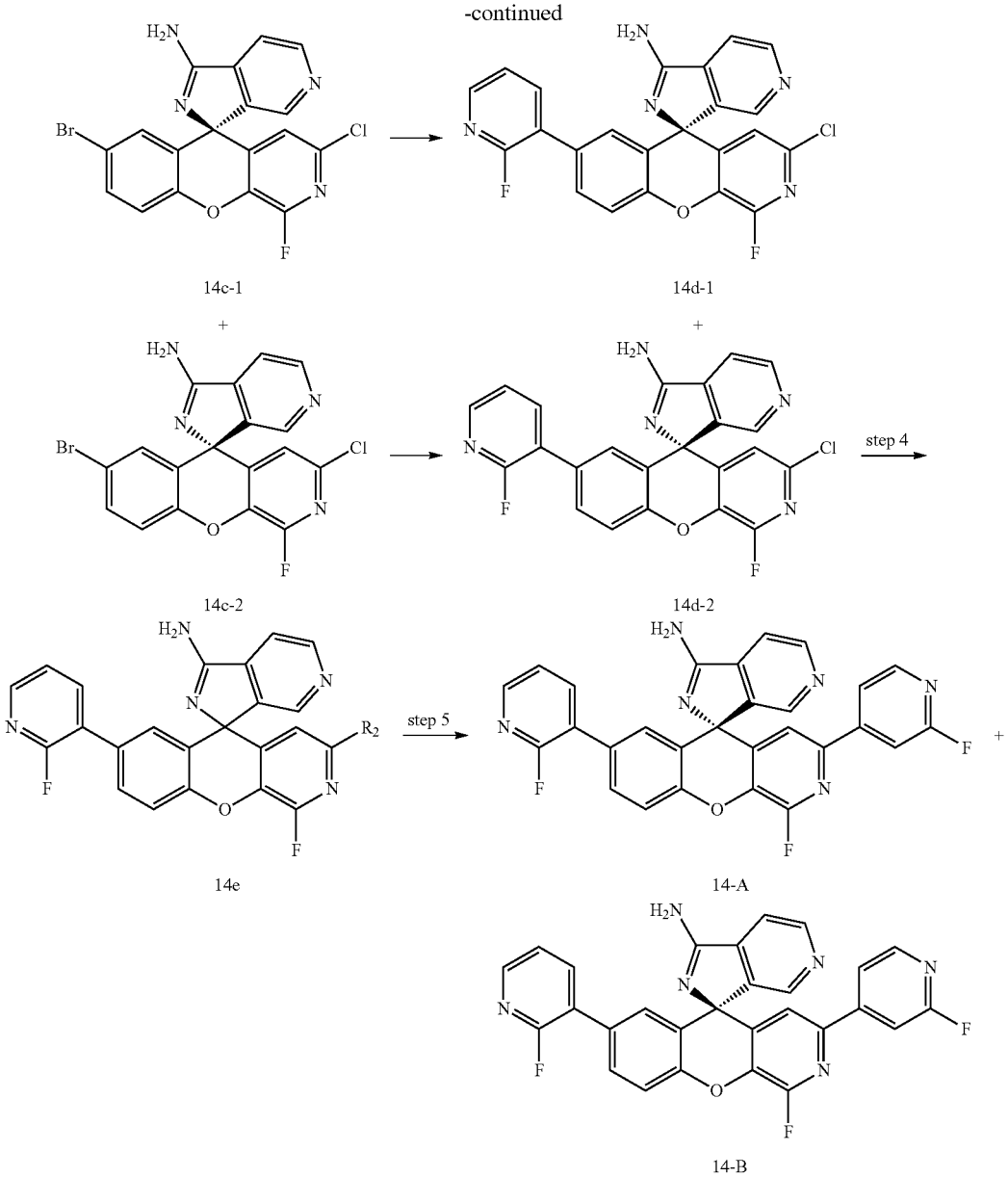

Step 2: 7-Bromo-3-chloro-1-fluorospiro[chromeno[2,3-c]pyridine-5,3'-pyrrolo[3,4-c]pyridin]-1'-amine 2,2,2-trifluoroacetate (14c)

A solution of n-BuLi (0.174 ml, 0.278 mmol) was added dropwise to a solution of 3-bromo-4-cyanopyridine (50.9 mg, 0.278 mmol, Alfa Aesar) in THF (5 ml) at −95° C. After 2 min a solution of N-(7-bromo-3-chloro-1-fluoro-5H-chromeno[2,3-c]pyridin-5-ylidene)-2-methylpropane-2-sulfinamide (100 mg, 0.232 mmol, Example 8) in THF (3 mL) was added. After 5 min aqueous, saturated $NH_4Cl$ solution was added and the reaction mixture was allowed to warm to RT. EtOAc was added to the mixture and the organic phase was separated and dried over $MgSO_4$ and the solvent was removed under reduced pressure. The residue was purified by flash chromatography (20-100% EtOAc/hexanes) to give the title compound as a light-yellow powder (37 mg, 0.086 mmol). MS m/z=432.5 [M+H]$^+$. Calculated for $C_{18}H_9BrClFN_4O$: 431.65

$^1$H NMR (300 MHz, CHLOROFORM-d) δ ppm 6.65 (s, 1H) 6.85 (d, J=2.34 Hz, 1H) 7.34 (d, J=8.92 Hz, 1H) 7.53 (dd, J=8.84, 2.41 Hz, 1H) 7.92 (dd, J=5.12, 1.17 Hz, 1H) 8.43 (d, J=1.02 Hz, 1H) 8.75 (d, J=5.12 Hz, 1H).

Chiral separation:

7-Bromo-3-chloro-1-fluorospiro[chromeno[2,3-c]pyridine-5,3'-pyrrolo[3,4-c]pyridin]-1'-amine (483 mg) was subjected to chromatography using supercritical $CO_2$ (additives 35% MeOH with 20 mM $NH_3$) on a ChiralPak ADH (21×250 mm, 5 μm) eluting at a flow rate 65 ml/min (100 bar pressure, 40° C. column temperature). The first peak (retention time=1.8 min) provided (R)-7-Bromo-3-chloro-1-fluorospiro[chromeno[2,3-c]pyridine-5,3'-pyrrolo[3,4-c]pyridin]-1'-amine (Example 14c-1, >99% ee), and the second peak (retention time=3.5 min) provided (S)-7-Bromo-3-chloro-1-fluorospiro[chromeno[2,3-c]pyridine-5,3'-pyrrolo[3,4-c]pyridin]-1'-amine (Example 14c-2, >99% ee).

¹H-NMR (14c-1, 400 MHz, CHLOROFORM-d) δ ppm 6.65 (s, 1H) 6.85 (d, J=2.35 Hz, 1H) 7.34 (d, J=8.80 Hz, 1H) 7.53 (dd, J=8.80, 2.35 Hz, 1H) 7.92 (dd, J=5.18, 1.08 Hz, 1H) 8.43 (d, J=0.78 Hz, 1H) 8.75 (d, J=5.09 Hz, 1H).

¹H-NMR (14c-2, 400 MHz, CHLOROFORM-d) δ ppm 6.65 (s, 1H) 6.85 (d, J=2.35 Hz, 1H) 7.35 (d, J=8.80 Hz, 1H) 7.53 (dd, J=8.80, 2.35 Hz, 1H) 7.92 (d, J=5.28 Hz, 1H) 8.43 (s, 1H) 8.76 (d, J=5.09 Hz, 1H).

Mass for both peaks m/z=432.5 [M+H]⁺. Calculated for $C_{18}H_9BrClFN_4O$: 431.65.

Step 3: 3-Chloro-1-fluoro-7-(2-fluoropyridin-3-yl) spiro[chromeno[2,3-c]pyridine-5,3'-pyrrolo[3,4-c] pyridin]-1'-amine 2,2,2-trifluoroacetate (14d)

The title compound was synthesized by procedures and steps analogous to those described in Example 5 above, but using 7-bromo-3-chloro-1-fluorospiro[chromeno[2,3-c]pyridine-5,3'-pyrrolo[3,4-c]pyridin]-1'-amine 2,2,2-trifluoroacetate (14c) in step 3. MS m/z=448.0 [M+H]⁺. Calculated for $C_{23}H_{12}ClF_2N_5OC_2HF_3O_2$: 561.85 (TFA salt)

¹H-NMR (400 MHz, MeOH) δ ppm 7.15 (s, 1H) 7.22 (t, J=1.76 Hz, 1H) 7.31-7.40 (m, 1H) 7.64 (d, J=8.80 Hz, 1H) 7.74-7.83 (m, 1H) 7.92 (ddd, J=9.93, 7.68, 1.96 Hz, 1H) 8.12-8.18 (m, 1H) 8.20-8.23 (m, 1H) 8.77 (s, 2H) 9.02 (d, J=5.09 Hz, 2H).

(R)-3-Chloro-1-fluoro-7-(2-fluoropyridin-3-yl)spiro [chromeno[2,3-c]pyridine-5,3'-pyrrolo[3,4-c]pyridin]-1'-amine 2,2,2-trifluoroacetate (14d-1)

The title compound was synthesized by procedures and steps analogous to those described in Example 5 above, but using (R)-7-bromo-3-chloro-1-fluorospiro[chromeno[2,3-c]pyridine-5,3'-pyrrolo[3,4-c]pyridin]-1'-amine (14c-1) in step 3. MS m/z=447.5 [M+H]⁺. Calculated for $C_{23}H_{12}ClF_2N_5OC_2HF_3O_2$: 561.85 (TFA salt) ¹H NMR (400 MHz, MeOH) δ ppm 7.15 (s, 1H) 7.22 (t, J=1.66 Hz, 1H) 7.35 (ddd, J=7.24, 5.09, 1.76 Hz, 1H) 7.64 (d, J=8.61 Hz, 1H) 7.79 (d, J=8.80 Hz, 1H) 7.91 (ddd, J=9.93, 7.68, 1.76 Hz, 1H) 8.15 (d, J=4.70 Hz, 1H) 8.22 (dd, J=5.28, 0.98 Hz, 1H) 8.77 (s, 1H) 9.02 (d, J=5.28 Hz, 1H).

(S)-3-Chloro-1-fluoro-7-(2-fluoropyridin-3-yl)spiro [chromeno[2,3-c]pyridine-5,3'-pyrrolo[3,4-c]pyridin]-1'-amine 2,2,2-trifluoroacetate (14d-2)

The title compound was synthesized by procedures and steps analogous to those described in Example 5 above, but using (S)-7-bromo-3-chloro-1-fluorospiro[chromeno[2,3-c]pyridine-5,3'-pyrrolo[3,4-c]pyridin]-1'-amine (14c-2) in step 3. MS m/z=447.5 [M+H]⁺. Calculated for $C_{23}H_{12}ClF_2N_5O.C_2HF_3O_2$: 561.85 (TFA salt) ¹H NMR (400 MHz, MeOH) δ ppm 7.15 (s, 1H) 7.22 (s, 1H) 7.35 (ddd, J=7.14, 5.18, 1.76 Hz, 1H) 7.64 (d, J=8.80 Hz, 1H) 7.78 (d, J=8.61 Hz, 1H) 7.91 (ddd, J=9.88, 7.73, 1.76 Hz, 1H) 8.15 (d, J=4.70 Hz, 1H) 8.22 (d, J=5.09 Hz, 1H) 8.77 (s, 1H) 9.02 (d, J=5.28 Hz, 1H).

Steps 4 & 5: Synthesis and chiral separation of 1-Fluoro-7-(2-fluoropyridin-3-yl)-3-(2-fluoropyridin-4-yl)spiro[chromeno[2,3-c]pyridine-5,3'-pyrrolo [3,4-c]pyridin]-1'-amine The titled compound was synthesized by procedures and steps analogous to those described in Example 5 above, but using 3-chloro-1-fluoro-7-(2-fluoropyridin-3-yl)spiro [chromeno[2,3-c]pyridine-5,3'-pyrrolo[3,4-c]pyridin]-1'-amine 2,2,2-trifluoroacetate (14d) and in step 4. 1-Fluoro-7-(2-fluoropyridin-3-yl)-3-(2-fluoropyridin-4-yl)spiro [chromeno[2,3-c]pyridine-5,3'-pyrrolo[3,4-c]pyridin]-1'-amine 2,2,2-trifluoroacetate (14e, 77 mg) was subjected to chromatography using supercritical CO₂ (additives 26% MeOH with 20 mM NH₃) on a Chrialcel ADH column (21× 250 mm, 5 µm) eluting at a flow rate 65 ml/min (100 bar pressure, 40° C. column temperature). The first peak (retention time=5.3 min) provided (S)-3-(5,6-dihydro-2H-pyran-3-yl)-1-fluoro-7-(2-fluoropyridin-3-yl)spiro[chromeno[2,3-c] pyridine-5,1'-isoindol]-3'-amine (Example 14-A; >99% ee), and the second peak (retention time=7.0 min) provided (R)-3-(5,6-dihydro-2H-pyran-3-yl)-1-fluoro-7-(2-fluoropyridin-3-yl)spiro[chromeno[2,3-c]pyridine-5,1'-isoindol]-3'-amine (Example 14-B; TFA salt; >99% ee).

¹H-NMR (14-A, 400 MHz, CHLOROFORM-d) δ ppm 6.89-7.07 (m, 2H) 7.21 (t, J=5.97 Hz, 1H) 7.30 (s, 1H) 7.45-7.61 (m, 4H) 7.71 (t, J=8.12 Hz, 1H) 8.14 (d, J=4.50 Hz, 1H) 8.22 (d, J=5.28 Hz, 1H) 8.53 (s, 1H) 8.80 (d, J=5.09 Hz, 1H).

¹H NMR (14-B, 400 MHz, MeOH) δ ppm 6.99 (s, 1H) 7.30 (s, 1H) 7.34 (t, J=6.06 Hz, 1H) 7.52 (s, 1H) 7.55-7.61 (m, 1H) 7.63-7.69 (m, 1H) 7.72 (d, J=5.48 Hz, 1H) 7.85-7.92 (m, 1H) 7.94 (d, J=5.09 Hz, 1H) 8.12 (d, J=4.69 Hz, 1H) 8.20 (d, J=5.28 Hz, 1H) 8.48 (br. s., 1H) 8.74 (br. s., 1H).

Mass for both peaks m/z=509.0 [M+H]⁺. Calculated for $C_{28}H_{15}F_3N_6O$: 508.45.

Example 14-E

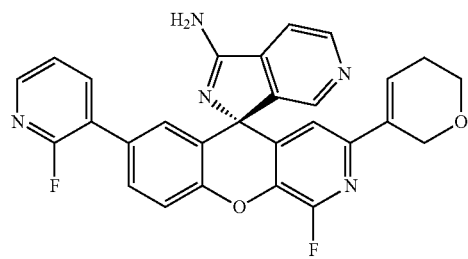 [SMILES: NC1=N[C@]2(c3cc(-c4cccnc4F)ccc3Oc3c2cc(C2=CCCOC2)nc3F)c2cnccc21]

Synthesis of (S)-3-(5,6-dihydro-2H-pyran-3-yl)-1-fluoro-7-(2-fluoropyridin-3-yl)spiro[chromeno[2,3-c]pyridine-5,3'-pyrrolo[3,4-c]pyridin]-1'-amine The title compound was synthesized by procedures and steps analogous to those described in Example 14 above, but using (S)-3-Chloro-1-fluoro-7-(2-fluoropyridin-3-yl)spiro [chromeno[2,3-c]pyridine-5,3'-pyrrolo[3,4-c]pyridin]-1'-amine 2,2,2-trifluoroacetate (14d-2) and 2-(5,6-dihydro-2H-pyran-3-yl)-4,4,5,5-tetramethyl-1,3,2-dioxaborolane in step 5. MS m/z=496.0 [M+H]⁺. Calculated for: $C_{28}H_{19}F_2N_5O_2.C_2HF_3O_2$: 609.50 (TFA salt)

¹H NMR (300 MHz, MeOH) ppm 2.22-2.32 (m, 2H) 3.75 (t, J=5.55 Hz, 2H) 4.42 (d, J=1.90 Hz, 2H) 6.62 (ddd, J=3.98, 2.27, 2.08 Hz, 1H) 6.95 (s, 1H) 7.20 (t, J=1.83 Hz, 1H) 7.32-7.38 (m, 1H) 7.63 (d, J=8.62 Hz, 1H) 7.74-7.80 (m, 1H)

7.92 (ddd, J=9.90, 7.64, 1.90 Hz, 1H) 8.15 (d, J=4.82 Hz, 1H) 8.22 (dd, J=5.19, 1.10 Hz, 1H) 8.74 (s, 1H) 9.01 (d, J=5.26 Hz, 1H)

Example 15

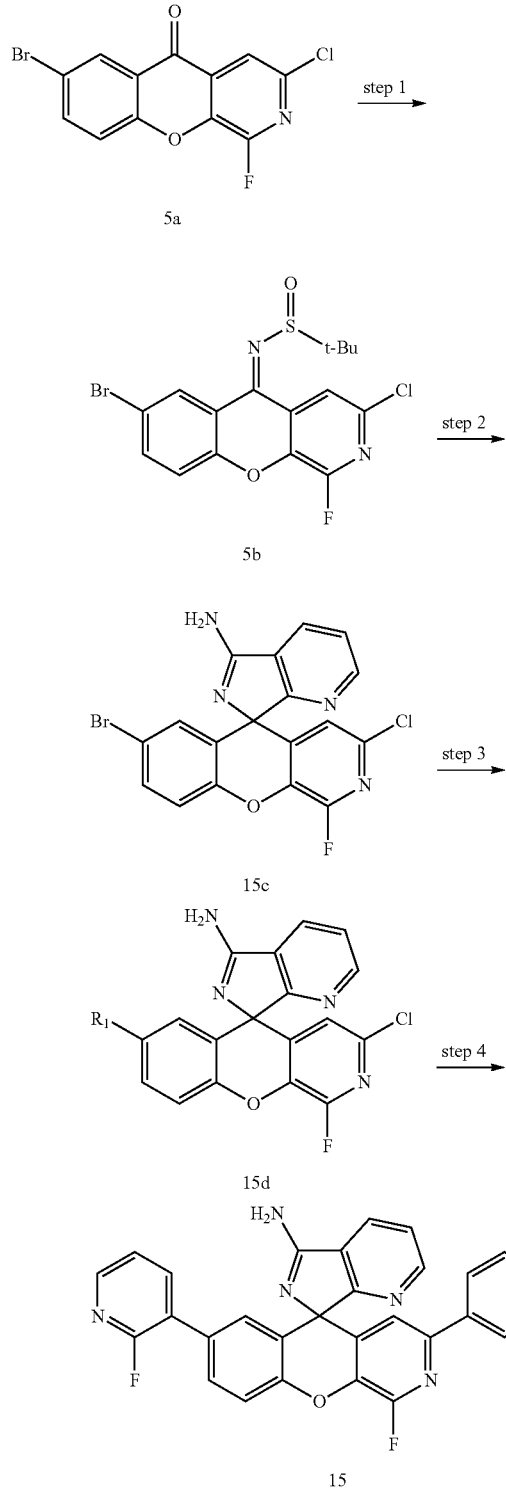

Synthesis of 1-Fluoro-7-(2-fluoropyridin-3-yl)-3-(2-fluoropyridin-4-yl)spiro[chromeno[2,3-c]pyridine-5,7'-pyrrolo[3,4-b]pyridin]-5'-amine (racemic mixture)

Step 2: 7-Bromo-3-chloro-1-fluorospiro[chromeno[2,3-c]pyridine-5,7'-pyrrolo[3,4-b]pyridin]-5'-amine (15c)

A solution of n-butyllithium (102 µL, 0.164 mmol, Aldrich) was added dropwise to a solution of 2-bromonicotinonitrile (30 mg, 0.164 mmol, Aldrich) in THF (2 mL) at −95° C. under N$_2$ atmosphere. After 1 min a solution of N-(7-bromo-3-chloro-1-fluoro-5H-chromeno[2,3-c]pyridin-5-ylidene)-2-methylpropane-2-sulfinamide (55 mg, 0.127 mmol, example 1b) in THF (1 mL) was added. After 2 min aqueous, saturated NH$_4$Cl solution was added and the reaction mixture was allowed to warm to RT. EtOAc was added and the organic phase was separated. The organic phase was dried over MgSO$_4$ and the solvent was removed under reduced pressure. The remaining residue was purified by reversed-phase preparative HPLC using a Phenomenex Gemini column, 10 micron, C18, 110 Å, 100×50 mm, 0.1% TFA in CH$_3$CN/H$_2$O, gradient 10% to 100% over 20 min to obtain the title compound as a light-yellow solid. MS m/z=432.8 [M+H]$^+$. Calculated for C$_{18}$H$_9$BrClFN$_4$O: 431.65

Step 3: 3-Chloro-1-fluoro-7-(2-fluoropyridin-3-yl)-spiro[chromeno[2,3-c]pyridine-5,7'-pyrrolo[3,4-b]pyridin]-5'-amine 2,2,2-trifluoroacetate (15d; racemic)

The titled compound was synthesized by procedures and steps analogous to those described in Example 5 above, but using 7-bromo-3-chloro-1-fluorospiro[chromeno[2,3-c]pyridine-5,7'-pyrrolo[3,4-b]pyridin]-5'-amine in step 3.

MS m/z=448.0 [M+H]$^+$. Calculated for C$_{23}$H$_{12}$ClF$_2$N$_5$O·C$_2$HF$_3$O$_2$: 561.85 (TFA salt)

Step 4: 1-Fluoro-7-(2-fluoropyridin-3-yl)-3-(2-fluoropyridin-4-yl)spiro[chromeno[2,3-c]pyridine-5,7'-pyrrolo[3,4-b]pyridin]-5'-amine (racemic)

The titled compound was synthesized by procedures and steps analogous to those described in Example 5 above, but using 3-chloro-1-fluoro-7-(2-fluoropyridin-3-yl)spiro[chromeno[2,3-c]pyridine-5,7'-pyrrolo[3,4-b]pyridin]-5'-amine 2,2,2-trifluoroacetate in step 4. MS m/z=509.0 [M+H]$^+$. Calculated for C$_{28}$H$_{15}$F$_3$N$_6$O: 508.45. $^1$H-NMR (300 MHz, MeOH) δ ppm 7.03 (t, J=1.83 Hz, 1H) 7.27-7.40 (m, 2H) 7.45-7.59 (m, 3H) 7.59-7.68 (m, 1H) 7.68-7.77 (m, 1H) 7.90 (ddd, J=9.87, 7.67, 1.90 Hz, 1H) 8.12 (d, J=4.97 Hz, 1H) 8.20 (d, J=5.41 Hz, 1H) 8.33 (dd, J=7.82, 1.39 Hz, 1H) 8.46 (dd, J=4.97, 1.46 Hz, 1H).

Example 16

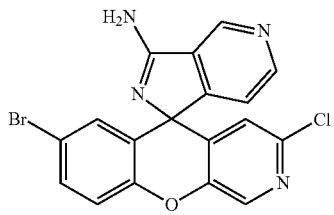 [SMILES: NC1=NC2(c3cc(Br)ccc3Oc3cnc(Cl)cc32)c2ccncc21]

Synthesis of 7-Bromo-3-chlorospiro[chromeno[2,3-c]pyridine-5,1'-pyrrolo[3,4-c]pyridin]-3'-amine 2,2,2-trifluoroacetate A solution of n-butyllithium (1.6M in hexane, 250 μL, 0.400 mmol, Aldrich) was added to a solution of 2,2,6,6-tetramethylpiperidine (67.5 μL, 0.400 mmol, Aldrich) in THF (1 mL) at −35° C. under $N_2$ gas. The solution was stirred for 15 min at −35° C. and then cooled to −95° C. After 5 min at −95° C. a solution of nicotinonitrile (41.6 mg, 0.4 mmol, Aldrich) in THF (1 mL) was added dropwise. After 2 min a solution of N-(7-bromo-3-chloro-5H-chromeno[2,3-c]pyridin-5-ylidene)-2-methylpropane-2-sulfinamide (165 mg, 0.400 mmol, Example 8b) in THF (2 mL) was added. After 5 min aqueous, saturated $NH_4Cl$ solution was added and the reaction mixture was allowed to warm to RT. EtOAc was added, the organic phase was separated and dried over $MgSO_4$. The solvent was removed under reduced pressure and the residue was dissolved in MeOH (3 mL) and a solution of hydrogen chloride in 1,4-dioxane (4 M, 200 μL, 0.800 mmol) was added dropwise. After 10 min the solvent was removed under reduced pressure. DCM and aqueous, saturated bicarbonate solution were added. The organic phase was separated. The aqueous phase was extracted with EtOAc. The organic phases were combined and dried over $MgSO_4$. The solvent was removed under reduced pressure. The residue was purified by reversed-phase preparative HPLC using a Phenomenex Gemini column, 10 micron, C18, 110 Å, 100× 50 mm, 0.1% TFA in $CH_3CN/H_2O$, gradient 10% to 100% over 20 min to yield the titled compound as a light-yellow solid.

MS m/z=413.0 $[M+H]^+$, 415.0 $[M+2H]^+$. Calculated for $C_{18}H_{10}BrClN_4OC_2HF_3O_2$: 527.68 (TFA salt).

$^1$H-NMR (300 MHz, MeOH) δ ppm 7.16-7.27 (m, 2H) 7.41 (d, J=8.92 Hz, 1H) 7.44 (dd, J=5.26, 1.02 Hz, 1H) 7.68 (dd, J=8.77, 2.34 Hz, 1H) 8.57 (s, 1H) 8.91 (d, J=5.26 Hz, 1H) 9.47 (d, J=0.88 Hz, 1H)

Example 17

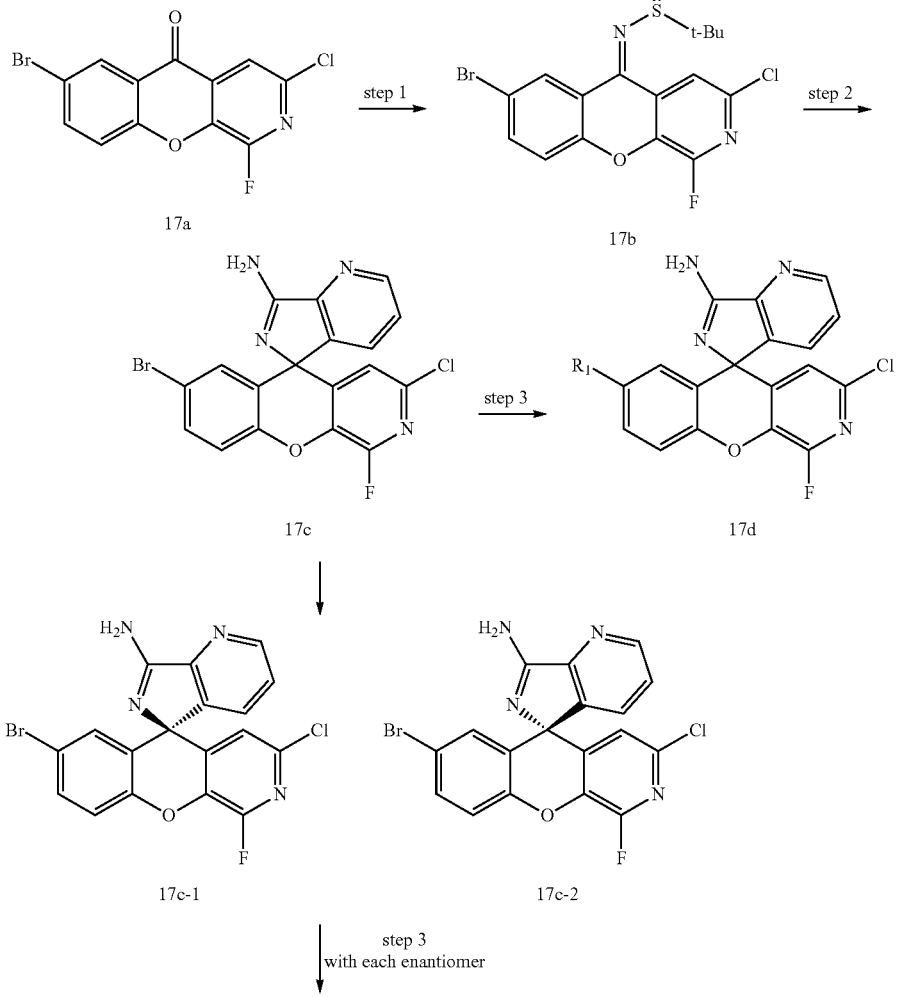

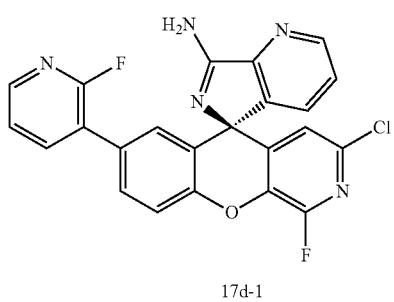

17d-1

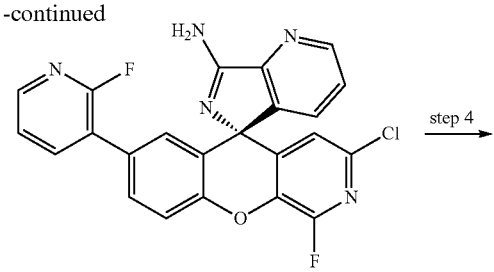

17d-2

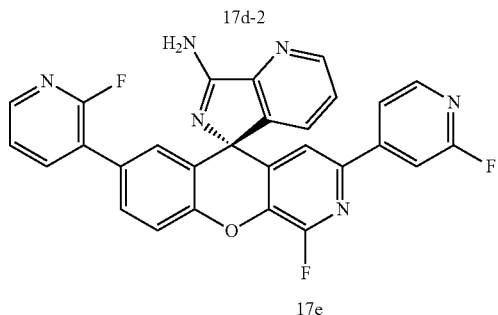

17e

Synthesis of 3-Chloro-1-fluoro-7-(2-fluoropyridin-3-yl)spiro[chromeno[2,3-c]pyridine-5,5'-pyrrolo[3,4-b]pyridin]-7'-amine 2,2,2-trifluoroacetate (17d)

Step 2: 7-Bromo-3-chloro-1-fluorospiro[chromeno[2,3-c]pyridine-5,5'-pyrrolo[3,4-b]pyridin]-7'-amine (17c)

A solution of n-BuLi (1.6 M in hexane; 0.174 ml, 0.278 mmol, Aldrich) was added dropwise to a solution of 3-bromopicolinonitrile (50.9 mg, 0.278 mmol, Alfa Aesar) in THF (5 ml) at −95° C. After 2 min a solution of N-(7-bromo-3-chloro-1-fluoro-5H-chromeno[2,3-c]pyridin-5-ylidene)-2-methylpropane-2-sulfinamide (100 mg, 0.232 mmol, example x) in THF (3 mL) was added. After 5 min aqueous, saturated NH$_4$Cl solution was added and the reaction mixture was allowed to warm to rt. EtOAc was added, the organic phase was separated and dried over MgSO$_4$. The solvent was removed under reduced pressure and the residue was purified by flash chromatography on silica gel (20-100% EtOAc/hexanes). The title compound was obtained as a yellow solid (38 mg, 0.088 mmol). MS m/z=432.8 [M+H]$^+$. Calculated for C$_{18}$H$_9$BrClFN$_4$O: 431.65.

$^1$H-NMR (300 MHz, MeOH) ppm 6.66 (s, 1H) 6.86 (d, J=2.34 Hz, 1H) 7.33 (d, J=8.92 Hz, 1H) 7.42 (dd, J=7.82, 4.75 Hz, 1H) 7.52 (dd, J=8.77, 2.48 Hz, 1H) 7.63 (dd, J=7.75, 1.32 Hz, 1H) 8.74 (dd, J=4.82, 1.32 Hz, 1H).

Chiral separation of 7-Bromo-3-chloro-1-fluorospiro[chromeno[2,3-c]pyridine-5,5'-pyrrolo[3,4-b]pyridin]-7'-amine (17c-1 & 17c-2)

7-Bromo-3-chloro-1-fluorospiro[chromeno[2,3-c]pyridine-5,5'-pyrrolo[3,4-b]pyridin]-7'-amine subjected to chromatography using supercritical CO$_2$ (additives 50% MeOH with 20 mM NH$_3$) on a Chiralpak ADH column (21×250 mm, 5 μm) eluting at a flow rate 63 ml/min (100 bar pressure, 40° C. column temperature). The first peak (retention time=2.34 min) provided (R)-7-Bromo-3-chloro-1-fluorospiro[chromeno[2,3-c]pyridine-5,5'-pyrrolo[3,4-b]pyridin]-7'-amine (Example 17c-1; 99% ee), and the second peak (retention time=3.98 min) provided (S)-7-Bromo-3-chloro-1-fluorospiro[chromeno[2,3-c]pyridine-5,5'-pyrrolo[3,4-b]pyridin]-7'-amine (Example 17c-2; 99% ee).

$^1$H NMR (17c-1, 400 MHz, MeOH) δ ppm 6.66 (s, 1H) 6.86 (d, J=2.35 Hz, 1H) 7.33 (d, J=9.00 Hz, 1H) 7.42 (dd, J=7.73, 4.99 Hz, 1H) 7.52 (dd, J=8.80, 2.15 Hz, 1H) 7.63 (d, J=6.85 Hz, 1H) 8.74 (d, J=3.91 Hz, 1H)

$^1$H NMR (17c-2, 400 MHz, MeOH) δ ppm 6.66 (s, 1H) 6.86 (d, J=2.35 Hz, 1H) 7.33 (d, J=8.80 Hz, 1H) 7.42 (dd, J=7.82, 4.89 Hz, 1H) 7.52 (dd, J=8.80, 2.35 Hz, 1H) 7.63 (dd, J=7.82, 1.17 Hz, 1H) 8.74 (dd, J=4.89, 1.17 Hz, 1H).

Mass for both peaks m/z=432.8 [M+H]=. Calculated for C$_{18}$H$_9$BrClFN$_4$O: 431.65.

Step 3: 3-Chloro-1-fluoro-7-(2-fluoropyridin-3-yl)spiro[chromeno[2,3-c]pyridine-5,5'-pyrrolo[3,4-b]pyridin]-7'-amine 2,2,2-trifluoroacetate (17d)

The titled compound was synthesized by procedures and steps analogous to those described in Example 5 above, but using 7-bromo-3-chloro-1-fluorospiro[chromeno[2,3-c]pyridine-5,5'-pyrrolo[3,4-b]pyridin]-7'-amine (17c) in step 3. MS m/z=448.0 [M+H]$^+$. Calculated for C$_{23}$H$_{12}$ClF$_2$N$_5$OC$_2$HF$_3$O$_2$: 561.85 (TFA salt). $^1$H NMR (300 MHz, MeOH) δ ppm 7.11 (s, 1H) 7.18 (t, J=1.68 Hz, 1H) 7.35 (ddd, J=7.31, 5.12, 1.75 Hz, 1H) 7.63 (d, J=8.62 Hz, 1H) 7.71-7.83 (m, 2H) 7.84-7.99 (m, 2H) 8.15 (ddd, J=3.22, 1.53, 1.39 Hz, 1H) 8.99 (dd, J=4.68, 1.32 Hz, 1H)

Step 3: (R)-3-Chloro-1-fluoro-7-(2-fluoropyridin-3-yl)-spiro[chromeno[2,3-c]pyridine-5,5'-pyrrolo[3,4-b]pyridin]-7'-amine 2,2,2-trifluoroacetate (17d-1)

The titled compound was synthesized by procedures and steps analogous to those described in Example 5 above, but using (R)-7-bromo-3-chloro-1-fluorospiro[chromeno[2,3-c]pyridine-5,5'-pyrrolo[3,4-b]pyridin]-7'-amine (17c-1) in step 3. MS m/z=447.5 [M+H]$^+$. Calculated for C$_{23}$H$_{12}$ClF$_2$N$_5$OC$_2$HF$_3$O$_2$: 561.85 (TFA salt). $^1$H NMR (400 MHz, MeOH) ppm 6.67 (s, 1H) 6.86 (d, J=2.35 Hz, 1H) 7.33

(d, J=8.80 Hz, 1H) 7.42 (dd, J=7.82, 4.89 Hz, 1H) 7.52 (dd, J=8.80, 2.54 Hz, 1H) 7.64 (dd, J=7.73, 1.27 Hz, 1H) 8.74 (dd, J=4.79, 1.27 Hz, 1H)

Step 3: (S)-3-Chloro-1-fluoro-7-(2-fluoropyridin-3-yl)spiro[chromeno[2,3-c]pyridine-5,5'-pyrrolo[3,4-b]pyridin]-7'-amine 2,2,2-trifluoroacetate (17d-2)

The titled compound was synthesized by procedures and steps analogous to those described in Example 5 above, but using (S)-7-bromo-3-chloro-1-fluorospiro[chromeno[2,3-c]pyridine-5,5'-pyrrolo[3,4-b]pyridin]-7'-amine (17c-2) in step 3. MS m/z=448.0 [M+H]$^+$. Calculated for $C_{23}H_{12}ClF_2N_5OC_2HF_3O_2$: 561.85 (TFA salt).
$^1$H NMR (400 MHz, MeOH) ppm 7.12 (s, 1H) 7.19 (s, 1H) 7.35 (t, J=5.48 Hz, 1H) 7.63 (d, J=8.80 Hz, 1H) 7.73-7.82 (m, 2H) 7.87-7.97 (m, 2H) 8.15 (d, J=4.89 Hz, 1H) 8.99 (d, J=3.52 Hz, 1H)

Step 4: (S)-1-fluoro-7-(2-fluoropyridin-3-yl)-3-(2-fluoropyridin-4-yl)spiro[chromeno[2,3-c]pyridine-5,5'-pyrrolo[3,4-b]pyridin]-7'-amine (17e)

The titled compound was synthesized by procedures and steps analogous to those described in Example 5 above, but using (S)-3-Chloro-1-fluoro-7-(2-fluoropyridin-3-yl)spiro [chromeno[2,3-c]pyridine-5,5'-pyrrolo[3,4-b]pyridin]-7'-amine 2,2,2-trifluoroacetate (17d-2) in step 4. MS m/z=508.9 [M+H]$^+$. Calculated for $C_{28}H_{15}ClF_3N_6OC_2HF_3O_2$: 622.48 (TFA salt).
$^1$H NMR (300 MHz, MeOH) ppm 7.18 (t, J=1.75 Hz, 1H) 7.36 (ddd, J=7.27, 5.08, 1.83 Hz, 1H) 7.63-7.71 (m, 3H) 7.73-7.82 (m, 2H) 7.85 (d, J=5.41 Hz, 1H) 7.89-7.97 (m, 2H) 8.16 (d, J=4.82 Hz, 1H) 8.23 (d, J=5.41 Hz, 1H) 9.00 (dd, J=4.75, 1.39 Hz, 1H)

Example 17-F

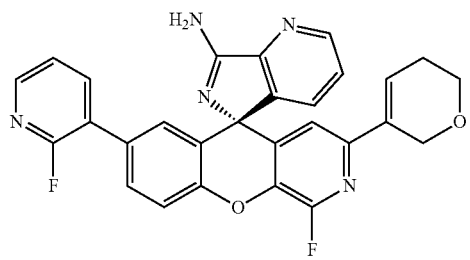 [SMILES: NC1=N[C@]2(c3cc(-c4cccnc4F)ccc3Oc3c2cc(C2=CCCOC2)nc3F)c2cccnc21]

Synthesis of (S)-3-(5,6-dihydro-2H-pyran-3-yl)-1-fluoro-7-(2-fluoropyridin-3-yl)spiro[chromeno[2,3-c]pyridine-5,5'-pyrrolo[3,4-b]pyridin]-7'-amine The title compound was synthesized by procedures and steps analogous to those described in Example 5 above, but using (S)-3-Chloro-1-fluoro-7-(2-fluoropyridin-3-yl)spiro [chromeno[2,3-c]pyridine-5,5'-pyrrolo[3,4-b]pyridin]-7'-amine 2,2,2-trifluoroacetate and 2-(5,6-dihydro-2H-pyran-3-yl)-4,4,5,5-tetramethyl-1,3,2-dioxaborolane in step 4. MS m/z=496.0 [M+H]$^+$. Calculated for: $C_{28}H_0F_2N_5O_2.C_2HF_3O_2$: 609.50 (TFA salt)
$^1$H NMR (300 MHz, MeOH) ppm 2.26 (br. s., 2H) 3.75 (t, J=5.55 Hz, 2H) 4.37-4.44 (m, 2H) 6.62 (br. s., 1H) 6.93 (s, 1H) 7.16 (d, J=1.61 Hz, 1H) 7.35 (ddd, J=7.23, 5.04, 1.75 Hz, 1H) 7.62 (d, J=8.62 Hz, 1H) 7.71-7.80 (m, 2H) 7.87-7.96 (m, 2H) 8.12-8.17 (m, 1H) 8.98 (dd, J=4.68, 1.32 Hz, 1H)

Example 17-G

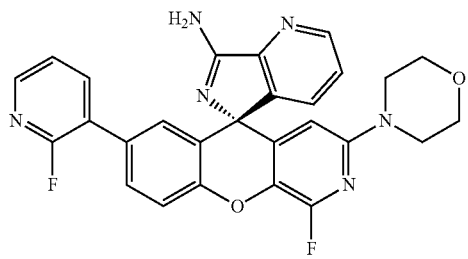 [SMILES: NC1=N[C@]2(c3cc(-c4cccnc4F)ccc3Oc3c2cc(N2CCOCC2)nc3F)c2cccnc21]

Synthesis of (S)-1-fluoro-7-(2-fluoropyridin-3-yl)-3-morpholinospiro[chromeno[2,3-c]pyridine-5,5'-pyrrolo[3,4-b]pyridin]-7'-amine The title compound was synthesized by procedures and steps analogous to those described in Example 8 above, but using (S)-3-Chloro-1-fluoro-7-(2-fluoropyridin-3-yl)spiro [chromeno[2,3-c]pyridine-5,5'-pyrrolo[3,4-b]pyridin]-7'-amine 2,2,2-trifluoroacetate. MS m/z=499.0 [M+H]$^+$. Calculated for $C_{27}H_{20}F_2N_6O_2.C_2HF_3O_2$: 612.51 (TFA salt) $^1$H NMR (400 MHz, CHLOROFORM-d) ppm 3.30-3.40 (m, 4H) 3.71-3.82 (m, 4H) 7.10 (s, 1H) 7.29-7.35 (m, 1H) 7.50 (d, J=8.61 Hz, 1H) 7.56-7.66 (m, 3H) 7.67-7.71 (m, 1H) 7.77-7.86 (m, 1H) 8.21 (d, J=3.91 Hz, 1H) 8.86 (dd, J=4.69, 1.17 Hz, 1H) 11.95 (br. s., 1H)

Example 18

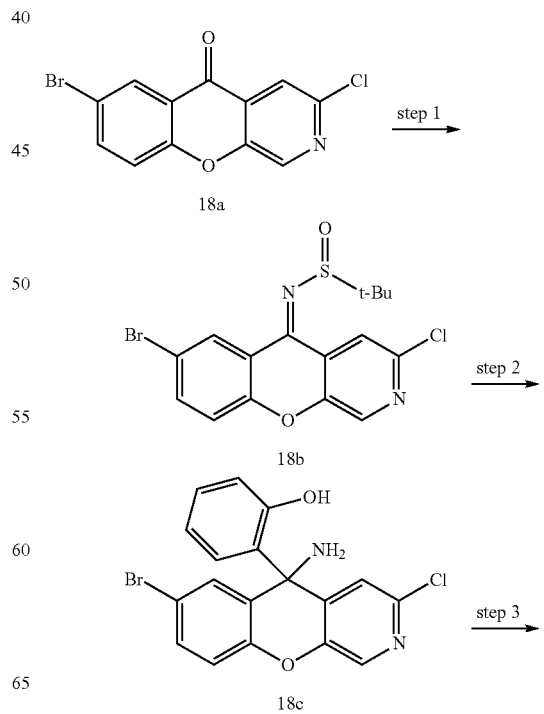

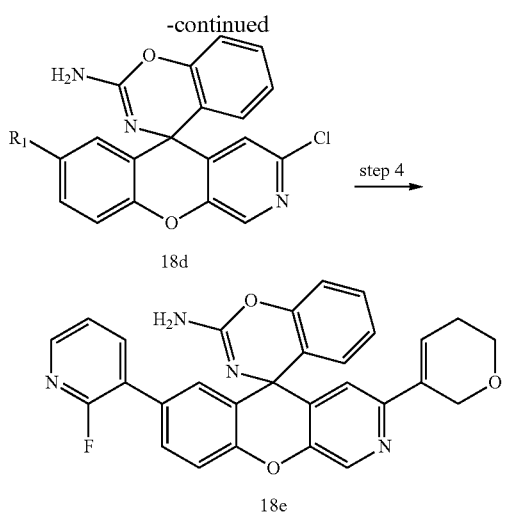

Synthesis of 3'-(5,6-dihydro-2H-pyran-3-yl)-7'-(2-fluoropyridin-3-yl)spiro[benzo[e][1,3]oxazine-4,5'-chromeno[2,3-c]pyridin]-2-amine (racemic mixture)

Step 1: N-(7-bromo-3-chloro-5H-chromeno[2,3-c]pyridin-5-ylidene)-2-methylpropane-2-sulfinamide (18b)

A mixture of 7-bromo-3-chloro-5H-chromeno[2,3-c]pyridin-5-one (20 g, 64.4 mmol), 2-methyl-2-propanesulfinamide (23.42 g, 193 mmol) and titanium (IV) ethoxide (45.3 mL, 219 mmol) in dry THF 250 mL was heated at 75° C. overnight. The mixture was cooled to RT, then brine was added while stirring. The resulting suspension was filtered through celite, and the solid was washed with EtOAc. The filtrate was washed with brine, dried over sodium sulfate and concentrated. The crude material was purified by column chromatography with gradient of 0-30% EtOAc/Hexane to give the desired product as an orange solid. MS m/z=415.0 [M+H]$^+$.

Step 2: 2-(5-amino-7-bromo-3-chloro-5H-chromeno[2,3-c]pyridin-5-yl)phenol (18c)

Butyllithium solution, 2.5m in hexanes (1.257 mL, 3.14 mmol) was added dropwise to a solution of 1-bromo-2-(ethoxymethoxy)benzene (0.726 g, 3.14 mmol) in THF 20 mL at −78° C. The reaction was stirred for 25 min. Then N-(7-bromo-3-chloro-5H-chromeno[2,3-c]pyridin-5-ylidene)-2-methylpropane-2-sulfinamide (1.0 g, 2.417 mmol) in THF was added. The reaction was warmed up to RT and stirred for an hour. The reaction was quenched with saturated ammonium chloride solution and extracted with EtOAc. The organic phase was separated and washed with brine, dried over sodium sulfate, filtered and concentrated. The crude material was purified by column chromatography with gradient of 15-50% EtOAc/Hexane. The resulting material was dissolved in dry MeOH 10 mL and cooled in an ice bath. Hydrochloric acid, 4.0M solution in 1,4-dioxane (20 mL, 80 mmol) was added and mixture was stirred at RT for 4 h. The reaction was quenched with 10% sodium carbonate solution and extracted with DCM three times. The combined organic layers were washed with brine, dried on sodium sulfate, filtered and concentrated to give the desired product which was used without further purificationMS m/z=402.8 [M+H]$^+$.

Step 3: 7'-bromo-3'-chlorospiro[benzo[e][1,3]oxazine-4,5'-chromeno[2,3-c]pyridin]-2-amine (racemic, 18d)

To a solution of 2-(5-amino-7-bromo-3-chloro-5H-chromeno[2,3-c]pyridin-5-yl)phenol (0.406 g, 1.006 mmol) in MeOH 5 mL was added potassium acetate (0.126 mL, 2.012 mmol) followed by the dropwise addition of cyanogen bromide, 3.0M solution in DCM (0.402 mL, 1.207 mmol). The resulting mixture was stirred at RT overnight. The reaction mixture was concentrated, washed with sat. NaHCO$_3$, extracted with DCM, dried over Na$_2$SO$_4$ and concentrated. The resulting product was dissolved in 1,2-dichloroethane followed by the addition of 4.0 M HCl in dioxane (15 mL) and stirred at RT for 1.5 h. The reaction mixture was concentrated, diluted with dichloromethane and washed with saturated NaHCO$_3$ solution, brine, dried over Na$_2$SO$_4$, filtered, concentrated. The crude material was purified by chromatography on silica gel using gradient of 0-100% EtOAc/hexanes to give the desired product. MS m/z=429.8 [M+H]$^+$.

Step 4: 3'-(5,6-dihydro-2H-pyran-3-yl)-7'-(2-fluoropyridin-3-yl)spiro[benzo[e][1,3]oxazine-4,5'-chromeno[2,3-c]pyridin]-2-amine (racemic, 18e)

A microwave tube was charged with 7'-bromo-3'-chlorospiro[benzo[e][1,3]oxazine-4,5'-chromeno[2,3-c]pyridin]-2-amine (0.135 g, 0.315 mmol), potassium phosphate tribasic (0.078 mL, 0.945 mmol), 2-fluoro-3-pyridineboronic acid (0.049 g, 0.346 mmol) in dioxane water (3 mL, 1:1). The reaction mixture was heated in microwave at 100° C. for 40 min. The mixture was diluted with water and extracted with EtOAc. The organic layer was washed with saturated sodium bicarbonate solution twice, then dried on sodium sulfate, filtered and concentrated in vacuo. The crude material was purified by column chromatography with gradient of 20-100% EtOAc/Hexane to give 3'-chloro-7'-(2-fluoropyridin-3-yl)spiro[benzo[e][1,3]oxazine-4,5'-chromeno[2,3-c]pyridin]-2-amine. This material (0.049 g, 0.110 mmol) was combined with potassium phosphate tribasic (0.027 mL, 0.330 mmol), 5,6-dihydro-2H-pyran-3-ylboronic acid (0.028 g, 0.220 mmol) and bis(di-tert-butyl(4-dimethylaminophenyl)phosphine)dichloropalladium(II) (3.90 mg, 5.51 µmol) in dioxane/water (1 mL, 3:1). The mixture was heated to 100° C. for 1 h. The reaction was completed and it was poured into water and extracted with EtOAc three times. The combined organic layers were washed with brine, dried on sodium sulfate, filtered and concentrated. The crude material was purified by column chromatography with gradient of 70-100% EtOAc/Hexane to give the desired product. MS m/z=493.1 [M+H]$^+$.

Example 19

Example 19 in table 1 herein was prepared using a method similar to that described in Example 18, Step 4 but using 2-fluoropyridine-4-boronic acid. Mass for Example 19 is presented in table 1.

Example 20

Example 20 in table 1 herein was prepared using a method similar to that described in Example 18, but using pyrimidin- 5-ylboronic acid and 2-fluoropyridine-4-boronic acid as described in Step 4. Mass for Example 20 is presented in table 1.

Example 21

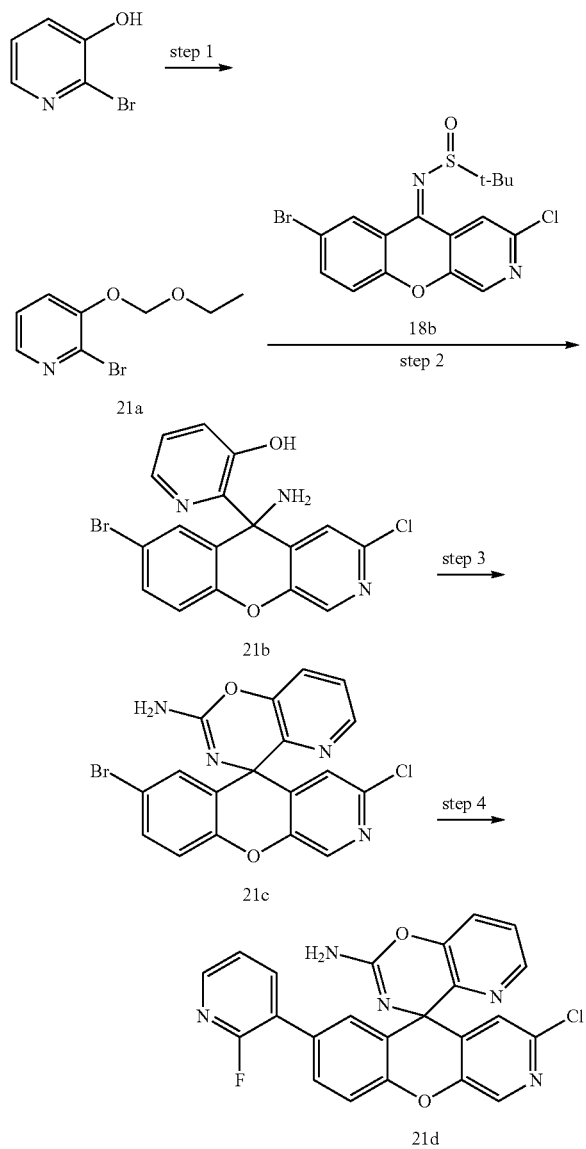

Synthesis of 3-chloro-7-(2-fluoropyridin-3-yl)spiro [chromeno[2,3-c]pyridine-5,4'-pyrido[2,3-e][3]oxazin]-2'-amine (racemic mixture)

Step 1: 2-bromo-3-(ethoxymethoxy)pyridine (21a)

To a RBF was added 2-bromo-3-pyridinol (6.0 g, 34.5 mmol) and potassium carbonate (11.91 g, 86 mmol) in Acetone (50 mL). The suspension was stirred at ambient temperature for 30 min and then treated with the drop-wise addition of chloromethyl ethyl ether (3.34 mL, 36.7 mmol) via addition funnel. The mixture was stirred at ambient temperature overnight. The mixture was filtered and the filtrate partitioned between EtOAc and water. The combined organic layers were washed with water, saturated solution of sodium bicarbonate and brine, then dried over $Mg_2SO_4$ to afford 7.12 g of desired product as a clear oil which was used without further purification.

Step 2: 2-(5-amino-7-bromo-3-chloro-5H-chromeno [2,3-c]pyridin-5-yl)pyridin-3-ol (21b)

Butyllithium solution, 2.5m in hexanes (1.70 mL, 4.24 mmol) was added dropwise to a solution of 2-bromo-3-(ethoxymethoxy)pyridine (0.98 g, 4.24 mmol) in THF 25 mL at −78° C. The reaction was stirred for 25 min. Then N-(7-bromo-3-chloro-5H-chromeno[2,3-c]pyridin-5-ylidene)-2-methylpropane-2-sulfinamide (1.35 g, 3.26 mmol, prepared as in Example 18b) in THF was added. The reaction was warmed up to RT and stirred for 1 h. The reaction was quenched with aq. ammonium chloride and extracted with EtOAc. The organic phase was separated and washed with brine, dried over sodium sulfate, filtered and concentrated. The crude material was purified by column chromatography with 25-60% EtOAc/Hexane to give 0.94 g of desired product. The resulting material was dissolved in dry MeOH 10 mL and cooled in an ice bath. Hydrochloric acid, 4.0M solution in 1,4-dioxane (20 mL, 80 mmol) was added and mixture was stirred at RT for 4 h. The reaction was quenched with 10% sodium carbonate solution and extracted with DCM three times. The combined organic layers were washed with brine, dried on sodium sulfate, filtered and concentrated to give the desired product which was used without further purification.

Step 3: 7-bromo-3-chlorospiro[chromeno[2,3-c]pyridine-5,4'-pyrido[2,3-e][1,3]oxazin]-2'-amine (racemic, 21c)

To a solution of 2-(5-amino-7-bromo-3-chloro-5H-chromeno[2,3-c]pyridin-5-yl)pyridin-3-ol (0.40 g, 1.00 mmol) in MeOH 5 mL was added potassium acetate (0.13 mL, 1.99 mmol) followed by the dropwise addition of cyanogen bromide, 3.0M solution in DCM (0.40 mL, 1.20 mmol). The resulting mixture was stirred at RT overnight. The reaction mixture was concentrated, washed with saturated $NaHCO_3$, extracted with DCM, dried over sodium sulfate and concentrated. The resulting product was dissolved in 1,2-dichloroethane followed by the addition of 4.0 M HCl in dioxane (15 mL) and stirred at RT for 1.5 h. The reaction mixture was concentrated, diluted with DCM and washed with sat $NaHCO_3$, brine, dried over sodium sulfate, filtered, concentrated, and purified by column chromatography on silica gel using 0-100% EtOAc/hexanes to give 0.18 g of desired product.

Step 4: 3-chloro-7-(2-fluoropyridin-3-yl)spiro [chromeno[2,3-c]pyridine-5,4'-pyrido[2,3-e][1,3] oxazin]-2'-amine (racemic, 21d)

The titled compound was prepared by using 7-bromo-3-chlorospiro[chromeno[2,3-c]pyridine-5,4'-pyrido[2,3-e][1,3]oxazin]-2'-amine and 2-fluoropyridine-3-boronic acid and following the procedures as described in Example 18, Step 4. MS m/z=446.0 [M+H]$^+$.

Example 22

The titled compound was prepared by following the procedures described in Example 18, Step 4 but using 3-chloro-7-(2-fluoropyridin-3-yl)spiro[chromeno[2,3-c]pyridine-5,4'-pyrido[2,3-e][1,3]oxazin]-2'-amine and 2-fluoropyridine-4-boronic acid. Mass for Example 22 is presented in table 1.

Example 23

The titled compound was prepared by following the procedures described in Example 18, Step 4 but using pyridin-3-ylboronic acid and 2-fluoropyridine-4-boronic acid. Mass for Example 23 is presented in table 1.

Example 24

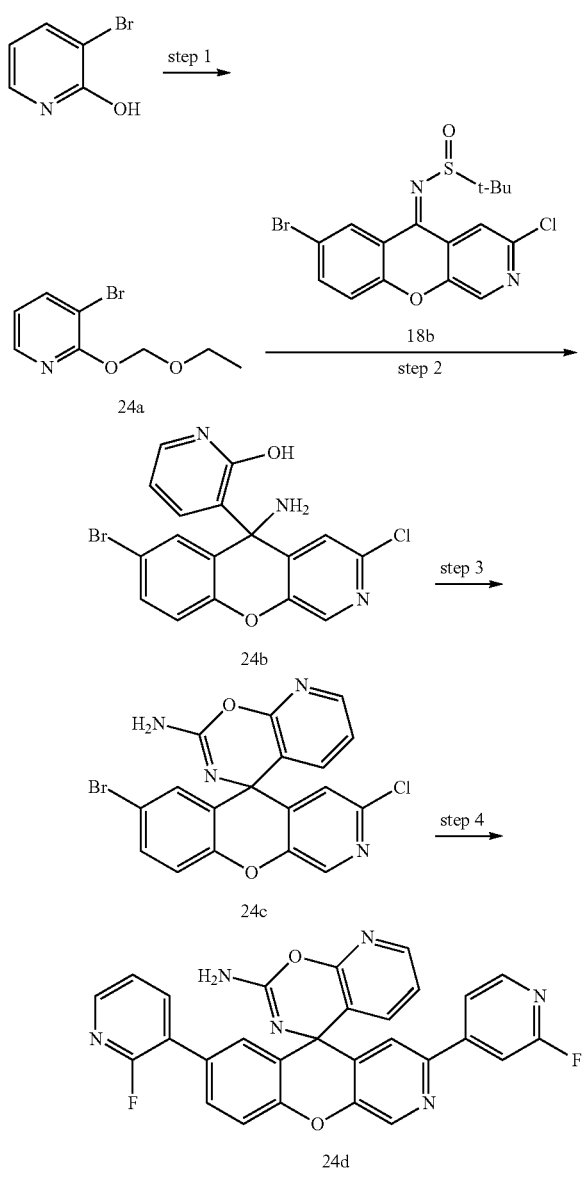

Synthesis of 7-(2-fluoropyridin-3-yl)-3-(2-fluoropyridin-4-yl)spiro[chromeno[2,3-c]pyridine-5,4'-pyrido[3,2-e][1,3]oxazin]-2'-amine (racemic mixture)

Step 1: 3-bromo-2-(ethoxymethoxy)pyridine (24a)

To a round-bottomed flask was added 3-bromo-2-hydroxypyridine (5 g, 28.7 mmol) and potassium carbonate (9.93 g, 71.8 mmol) in Acetone (300 mL). The suspension was stirred at ambient temperature for 30 min and then treated with the drop-wise addition of chloromethyl ethyl ether (2.78 mL, 30.6 mmol) via addition funnel. The mixture was stirred at ambient temperature overnight. The reaction mixture was filtered and the filtrate partitioned between EtOAc and water. The combined organic layers were washed with water, saturated solution of sodium bicarbonate and brine, dried over $Mg_2SO_4$, filtered and concentrated. The crude material was to afford 2.46 g of desired product as a clear oil which was used without further purification.

Step 2: 3-(5-amino-7-bromo-3-chloro-5H-chromeno[2,3-c]pyridin-5-yl)pyridin-2-ol (24b)

3-(5-amino-7-bromo-3-chloro-5H-chromeno[2,3-c]pyridin-5-yl)pyridin-2-ol was prepared by following the similar procedures as described in Example 21, Step 2 but using 3-bromo-2-(ethoxymethoxy)pyridine.

Step 3: 7-bromo-3-chlorospiro[chromeno[2,3-c]pyridine-5,4'-pyrido[3,2-e][1,3]oxazin]-2'-amine (recemic, 24c)

7-bromo-3-chlorospiro[chromeno[2,3-c]pyridine-5,4'-pyrido[3,2-e][1,3]oxazin]-2'-amine was prepared by following the similar procedures as described in Example 21, Step 3 but using 3-(5-amino-7-bromo-3-chloro-5H-chromeno[2,3-c]pyridin-5-yl)pyridin-2-ol.

Step 4: 7-(2-fluoropyridin-3-yl)-3-(2-fluoropyridin-4-yl)spiro[chromeno[2,3-c]pyridine-5,4'-pyrido[3,2-e][1,3]oxazin]-2'-amine (racemic, 24d)

The titled compound was prepared by following the procedures as described in Example 18, Step 4 but using 7-bromo-3-chlorospiro[chromeno[2,3-c]pyridine-5,4'-pyrido[3,2-e][1,3]oxazin]-2'-amine, 2-fluoropyridine-3-boronic acid and 2-fluoropyridine-4-boronic acid. MS m/z=506.9 [M+H]$^+$.

The following compounds in Table I are additional representative examples of compounds of Formulas I, II and III, and sub-formulas thereof, provided by the present invention. The methods used to prepare each exemplary compound correspond to those described in the Examples herein above. Table I further provides the mass and biological data (average nM $IC_{50}$'s for the enzyme and cell assays) for each compound, where available.

TABLE I

| Example No | Compound Structure | Compound Name | Calc MW | Observed MW | BAC E1 FERT assay (uM) | HEK cell assay (uM) |
|---|---|---|---|---|---|---|
| 5d | 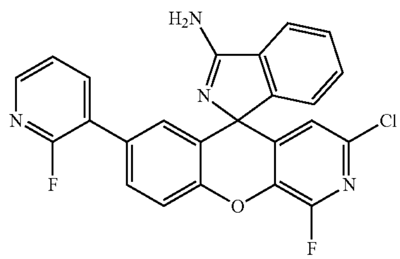 [SMILES: NC1=NC2(c3cc(-c4cccnc4F)ccc3Oc3c2cc(Cl)nc3F)c2ccccc21] | 3-chloro-1-fluoro-7-(2-fluoropyridin-3-yl)spiro[chromeno[2,3-c]pyridine-5,1'-isoindol]-3'-amine | 560.9 | 446.9 | 0.006 | 0.224 |
| 5e | 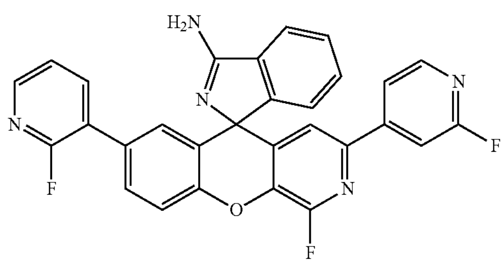 [SMILES: NC1=NC2(c3cc(-c4cccnc4F)ccc3Oc3c2cc(-c2ccnc(F)c2)nc3F)c2ccccc21] | 1-fluoro-7-(2-fluoropyridin-3-yl)-3-(2-fluoropyridin-4-yl)spiro[chromeno[2,3-c]pyridine-5,1'-isoindol]-3'-amine | 621.5 | 508.1 | 0.001 | 0.008 |
| 5-B | 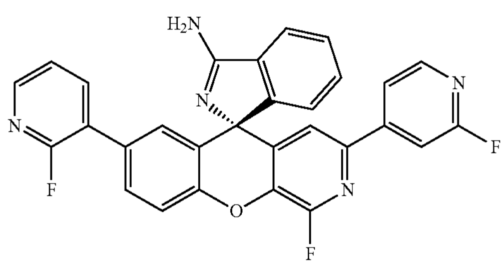 | (S)-1-fluoro-7-(2-fluoropyridin-3-yl)-3-(2-fluoropyridin-4-yl)spiro[chromeno[2,3-c]pyridine-5,1'-isoindol]-3'-amine | 507.5 | 508.1 | 0.0006 | 0.011 |
| 5-A | 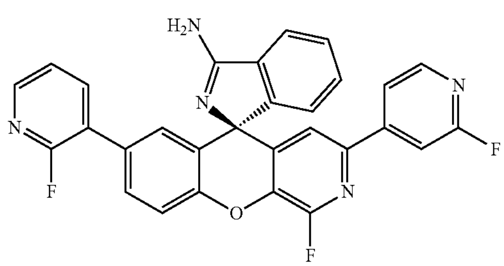 [SMILES: NC1=N[C@@]2(c3cc(-c4cccnc4F)ccc3Oc3c2cc(-c2ccnc(F)c2)nc3F)c2ccccc21] | (R)-1-fluoro-7-(2-fluoropyridin-3-yl)-3-(2-fluoropyridin-4-yl)spiro[chromeno[2,3-c]pyridine-5,1'-isoindol]-3'-amine | 507.5 | 508.1 | 0.0182 | 1.86 |
| 6 | 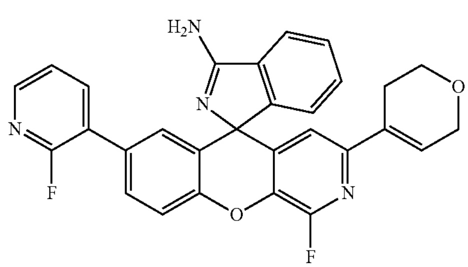 [SMILES: NC1=NC2(c3cc(-c4cccnc4F)ccc3Oc3c2cc(C2=CCOCC2)nc3F)c2ccccc21] | 3-(3,6-dihydro-2H-pyran-4-yl)-1-fluoro-7-(2-fluoropyridin-3-yl)spiro[chromeno[2,3-c]pyridine-5,1'-isoindol]-3'-amine | 608.5 | 495.2 | 0.001 | 0.003 |

TABLE I-continued

| Example No | Compound Name | Calc MW | Observed MW | BAC E1 FERT assay (uM) | HEK cell assay (uM) |
|---|---|---|---|---|---|
| 7 | 3-(5,6-dihydro-2H-pyran-3-yl)-1-fluoro-7-(2-fluoropyridin-3-yl)spiro[chromeno[2,3-c]pyridine-5,1'-isoindol]-3'-amine | 608.5 | 495.0 | 0.001 | 0.013 |
| 7-A | (R)-3-(5,6-dihydro-2H-pyran-3-yl)-1-fluoro-7-(2-fluoropyridin-3-yl)spiro[chromeno[2,3-c]pyridine-5,1'-isoindol]-3'-amine | 494.5 | 495.0 | 0.078 | 0.336 |
| 7-B | (S)-3-(5,6-dihydro-2H-pyran-3-yl)-1-fluoro-7-(2-fluoropyridin-3-yl)spiro[chromeno[2,3-c]pyridine-5,1'-isoindol]-3'-amine | 494.5 | 495.0 | 0.0005 | 0.005 |
| 8 | 1-fluoro-7-(2-fluoropyridin-3-yl)-3-morpholinospiro[chromeno[2,3-c]pyridine-5,1'-isoindol]-3'-amine | 611.5 | 497.9 | 0.0042 | 0.014 |
| 9 | 3-(3,3-difluoropyrrolidin-1-yl)-1-fluoro-7-(2-fluoropyridin-3-yl)spiro[chromeno[2,3-c]pyridine-5,1'-isoindol]-3'-amine | 631.5 | 518.0 | 0.0053 | 0.027 |
| 10c | 7-bromo-3-chlorospiro[chromeno[2,3-c]pyridine-5,1'-isoindol]-3'-amine | 526.7 | 411.8 413.9 | 6.94 | 0.0645 |

TABLE I-continued

| Example No | Compound Structure | Compound Name | Calc MW | Observed MW | BAC E1 FERT assay (uM) | HEK cell assay (uM) |
|---|---|---|---|---|---|---|
| 10d | 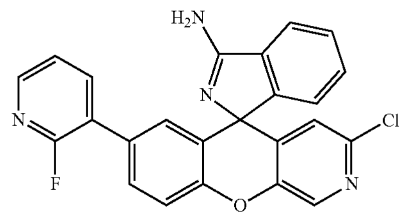 [SMILES: NC1=NC2(c3cc(-c4cccnc4F)ccc3Oc3cnc(Cl)cc32)c2ccccc21] | 3-chloro-7-(2-fluoropyridin-3-yl)spiro[chromeno[2,3-c]pyridine-5,1'-isoindol]-3'-amine | 542.9 | 429.0 | 0.036 | 0.14 |
| 10 | 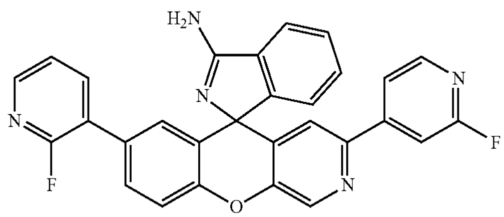 [SMILES: NC1=NC2(c3cc(-c4cccnc4F)ccc3Oc3cnc(-c4ccnc(F)c4)cc32)c2ccccc21] | 7-(2-fluoropyridin-3-yl)-3-(2-fluoropyridin-4-yl)spiro[chromeno[2,3-c]pyridine-5,1'-isoindol]-3'-amine | 603.5 | 490.0 | 0.001 | 0.012 |
| 11 | 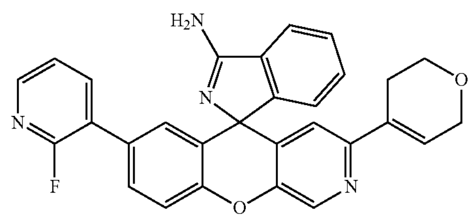 [SMILES: NC1=NC2(c3cc(-c4cccnc4F)ccc3Oc3cnc(C4=CCOCC4)cc32)c2ccccc21] | 3-(3,6-dihydro-2H-pyran-4-yl)-7-(2-fluoropyridin-3-yl)spiro[chromeno[2,3-c]pyridine-5,1'-isoindol]-3'-amine | 590.4 | 477.0 | 0.003 | 0.012 |
| 12 | 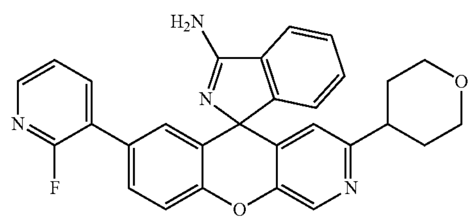 [SMILES: NC1=NC2(c3cc(-c4cccnc4F)ccc3Oc3cnc(C4CCOCC4)cc32)c2ccccc21] | 7-(2-fluoropyridin-3-yl)-3-(tetrahydro-2H-pyran-4-yl)spiro[chromeno[2,3-c]pyridine-5,1'-isoindol]-3'-amine | 592.6 | 479.1 | 0.004 | 0.013 |
| 13 | 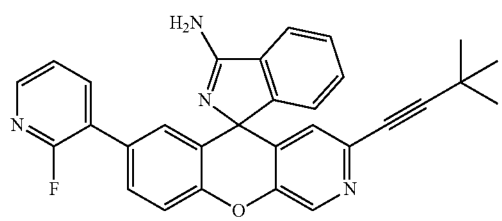 [SMILES: CC(C)(C)C#Cc1cc2c(cn1)Oc1ccc(-c3cccnc3F)cc1C21N=C(N)c2ccccc21] | 3-(3,3-dimethylbut-1-ynyl)-7-(2-fluoropyridin-3-yl)spiro[chromeno[2,3-c]pyridine-5,1'-isoindol]-3'-amine | 588.6 | 475.1 | 0.006 | 0.070 |
| 10-C | 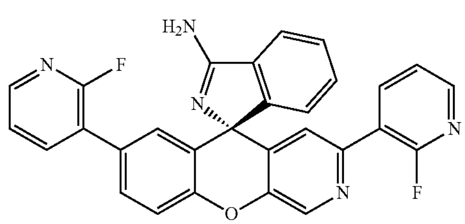 [SMILES: NC1=N[C@]2(c3cc(-c4cccnc4F)ccc3Oc3cnc(-c4cccnc4F)cc32)c2ccccc21] | (S)-3,7-bis(2-fluoropyridin-3-yl)spiro[chromeno[2,3-c]pyridine-5,1'-isoindol]-3'-amine | 489.5 | 490.9 | 0.90 | >10 |

TABLE I-continued

| Example No | Compound Name | Calc MW | Observed MW | BAC E1 FERT assay (uM) | HEK cell assay (uM) |
|---|---|---|---|---|---|
| 14c | 7-bromo-3-chloro-1-fluorospiro[chromeno[2,3-c]pyridine-5,3'-pyrrolo[3,4-c]pyridin]-1'-amine | 431.7 | 432.5 | 4.58 | >10 |
| 14c-1 | (R)-7-bromo-3-chloro-1-fluorospiro[chromeno[2,3-c]pyridine-5,3'-pyrrolo[3,4-c]pyridin]-1'-amine | 431.7 | 432.5 | >10 | >10 |
| 14c-2 | (S)-7-bromo-3-chloro-1-fluorospiro[chromeno[2,3-c]pyridine-5,3'-pyrrolo[3,4-c]pyridin]-1'-amine | 431.7 | 432.5 | 3.44 | >10 |
| 10-D | (R)-3,7-bis(2-fluoropyridin-3-yl)spiro[chromeno[2,3-c]pyridine-5,1'-isoindol]-3'-amine | 489.5 | 490.9 | >10 | >10 |
| 14d | 3-chloro-1-fluoro-7-(2-fluoropyridin-3-yl)spiro[chromeno[2,3-c]pyridine-5,3'-pyrrolo[3,4-c]pyridin]-1'-amine | 561.8 | 448.0 | 0.0037 | 0.771 |
| 14d-1 | (R)-3-chloro-1-fluoro-7-(2-fluoropyridin-3-yl)spiro[chromeno[2,3-c]pyridine-5,3'-pyrrolo[3,4-c]pyridin]-1'-amine | 561.8 | 447.5 | 6.57 | >10 |

TABLE I-continued

| Example No | Compound Structure | Compound Name | Calc MW | Observed MW | BACE1 FERT assay (uM) | HEK cell assay (uM) |
|---|---|---|---|---|---|---|
| 14d-2 | 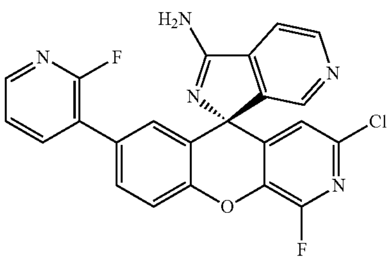 [SMILES: NC1=N[C@]2(c3cc(-c4cccnc4F)ccc3Oc3c2cc(Cl)nc3F)c2cnccc21] | (S)-3-chloro-1-fluoro-7-(2-fluoropyridin-3-yl)spiro[chromeno[2,3-c]pyridine-5,3'-pyrrolo[3,4-c]pyridin]-1'-amine | 561.8 | 447.5 | 0.0025 | 0.0355 |
| 14-A | 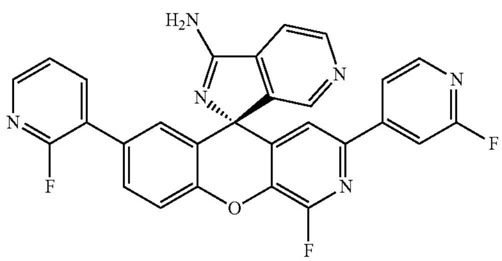 | (S)-1-fluoro-7-(2-fluoropyridin-3-yl)-3-(2-fluoropyridin-4-yl)spiro[chromeno[2,3-c]pyridine-5,3'-pyrrolo[3,4-c]pyridin]-1'-amine | 508.5 | 509.0 | 0.0004 | 0.008 |
| 14-B | 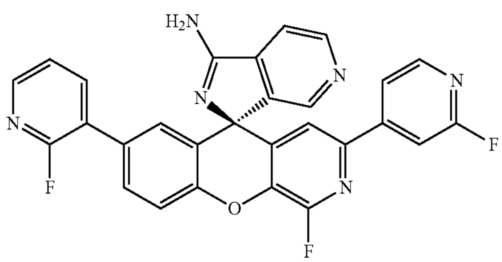 [SMILES: NC1=N[C@@]2(c3cc(-c4cccnc4F)ccc3Oc3c2cc(-c2ccnc(F)c2)nc3F)c2cnccc21] | (R)-1-fluoro-7-(2-fluoropyridin-3-yl)-3-(2-fluoropyridin-4-yl)spiro[chromeno[2,3-c]pyridine-5,3'-pyrrolo[3,4-c]pyridin]-1'-amine | 508.5 | 509.0 | 0.107 | 2.46 |
| 14-E | 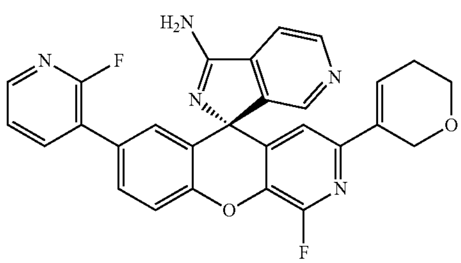 [SMILES: NC1=N[C@]2(c3cc(-c4cccnc4F)ccc3Oc3c2cc(C2=CCCOC2)nc3F)c2cnccc21] | (S)-3-(5,6-dihydro-2H-pyran-3-yl)-1-fluoro-7-(2-fluoropyridin-3-yl)spiro[chromeno[2,3-c]pyridine-5,3'-pyrrolo[3,4-c]pyridin]-1'-amine | 609.5 | 496.0 | 0.0005 | 0.002 |
| 15 | 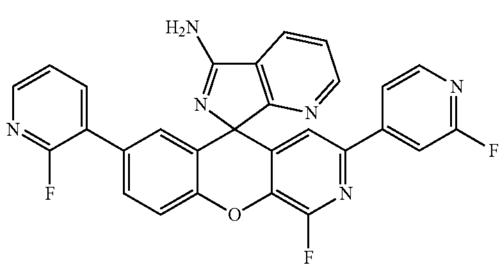 [SMILES: NC1=NC2(c3cc(-c4cccnc4F)ccc3Oc3c2cc(-c2ccnc(F)c2)nc3F)c2ncccc21] | 1-fluoro-7-(2-fluoropyridin-3-yl)-3-(2-fluoropyridin-4-yl)spiro[chromeno[2,3-c]pyridine-5,7'-pyrrolo[3,4-b]pyridin]-5'-amine | 508.5 | 509.0 | 0.001 | 0.011 |

TABLE I-continued

| Example No | Compound Structure | Compound Name | Calc MW | Observed MW | BAC E1 FERT assay (uM) | HEK cell assay (uM) |
|---|---|---|---|---|---|---|
| 16 | 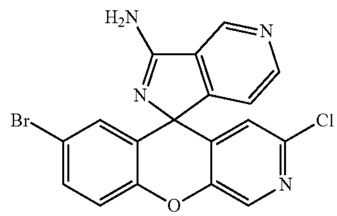 | 7-bromo-3-chlorospiro[chromeno[2,3-c]pyridine-5,1'-pyrrolo[3,4-c]pyridin]-3'-amine | 527.7 | 413.0 415.0 | 9.09 | >10 |
| 17c | 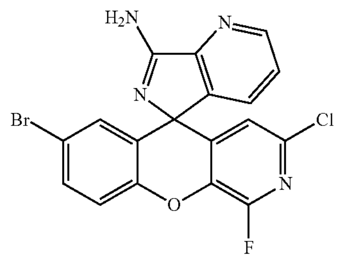 [SMILES: NC1=NC2(c3cc(Br)ccc3Oc3c2cc(Cl)nc3F)c2cccnc21] | 7-bromo-3-chloro-1-fluorospiro[chromeno[2,3-c]pyridine-5,5'-pyrrolo[3,4-b]pyridin]-7'-amine | 431.7 | 432.8 | >10 | >10 |
| 17c-2 | 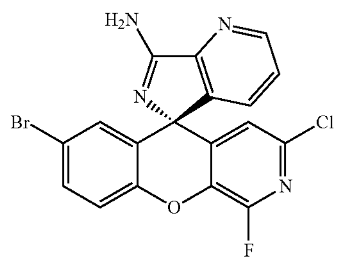 [SMILES: NC1=N[C@]2(c3cc(Br)ccc3Oc3c2cc(Cl)nc3F)c2cccnc21] | (S)-7-bromo-3-chloro-1-fluorospiro[chromeno[2,3-c]pyridine-5,5'-pyrrolo[3,4-b]pyridin]-7'-amine | 431.7 | 432.8 | 3.44 | >10 |
| 17c-1 | 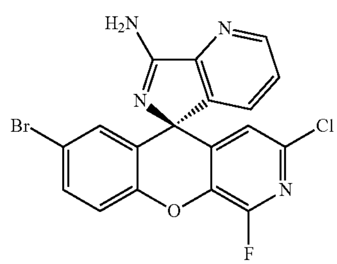 [SMILES: NC1=N[C@@]2(c3cc(Br)ccc3Oc3c2cc(Cl)nc3F)c2cccnc21] | (R)-7-bromo-3-chloro-1-fluorospiro[chromeno[2,3-c]pyridine-5,5'-pyrrolo[3,4-b]pyridin]-7'-amine | 431.7 | 432.8 | >10 | >10 |
| 17d | 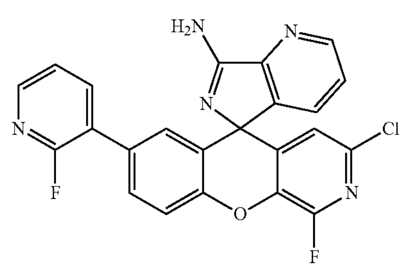 [SMILES: NC1=NC2(c3cc(-c4cccnc4F)ccc3Oc3c2cc(Cl)nc3F)c2cccnc21] | 3-chloro-1-fluoro-7-(2-fluoropyridin-3-yl)spiro[chromeno[2,3-c]pyridine-5,5'-pyrrolo[3,4-b]pyridin]-7'-amine 2,2,2-trifluoroacetate | 561.9 | 448.0 | 0.088 | 4.37 |
| 17d-1 | 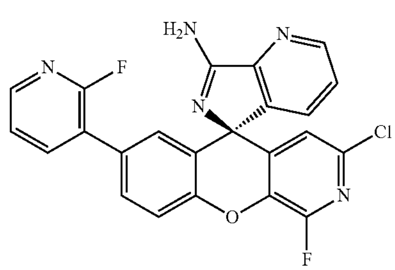 [SMILES: NC1=N[C@@]2(c3cc(-c4cccnc4F)ccc3Oc3c2cc(Cl)nc3F)c2cccnc21] | (R)-3-chloro-1-fluoro-7-(2-fluoropyridin-3-yl)spiro[chromeno[2,3-c]pyridine-5,5'-pyrrolo[3,4-b]pyridin]-7'-amine | 561.9 | 447.5 | >10 | >10 |

TABLE I-continued

| Example No | Compound Structure | Compound Name | Calc MW | Observed MW | BAC E1 FERT assay (uM) | HEK cell assay (uM) |
|---|---|---|---|---|---|---|
| 17d-2 | 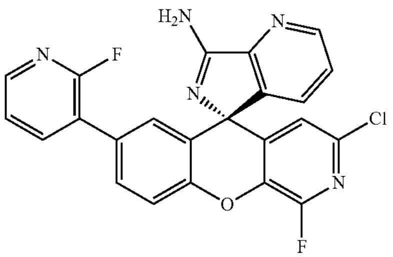 [SMILES: NC1=N[C@]2(c3cc(-c4cccnc4F)ccc3Oc3c2cc(Cl)nc3F)c2cccnc21] | (S)-3-chloro-1-fluoro-7-(2-fluoropyridin-3-yl)spiro[chromeno[2,3-c]pyridine-5,5'-pyrrolo[3,4-b]pyridin]-7'-amine | 561.9 | 448.0 | 0.016 | 1.57 |
| 17e | 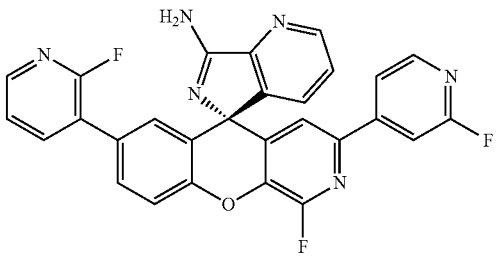 [SMILES: NC1=N[C@]2(c3cc(-c4cccnc4F)ccc3Oc3c2cc(-c2ccnc(F)c2)nc3F)c2cccnc21] | (S)-1-fluoro-7-(2-fluoropyridin-3-yl)-3-(2-fluoropyridin-4-yl)spiro[chromeno[2,3-c]pyridine-5,5'-pyrrolo[3,4-b]pyridin]-7'-amine | 622.5 | 508.9 | 0.0007 | 0.007 |
| 17-F | 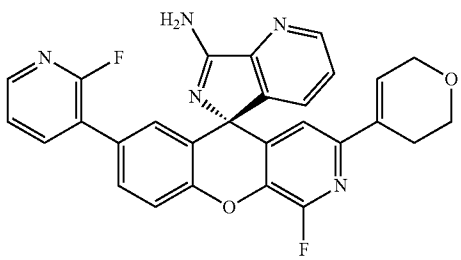 [SMILES: NC1=N[C@]2(c3cc(-c4cccnc4F)ccc3Oc3c2cc(C2=CCOCC2)nc3F)c2cccnc21] | (S)-3-(5,6-dihydro-2H-pyran-3-yl)-1-fluoro-7-(2-fluoropyridin-3-yl)spiro[chromeno[2,3-c]pyridine-5,5'-pyrrolo[3,4-b]pyridin]-7'-amine | 609.5 | 496.0 | 0.0007 | 0.003 |
| 17-G | 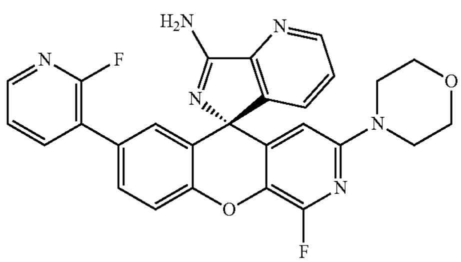 [SMILES: NC1=N[C@]2(c3cc(-c4cccnc4F)ccc3Oc3c2cc(N2CCOCC2)nc3F)c2cccnc21] | (S)-1-fluoro-7-(2-fluoropyridin-3-yl)-3-morpholinospiro[chromeno[2,3-c]pyridine-5,5'-pyrrolo[3,4-b]pyridin]-7'-amine | 612.5 | 499.0 | 0.001 | 0.002 |
| 18 | 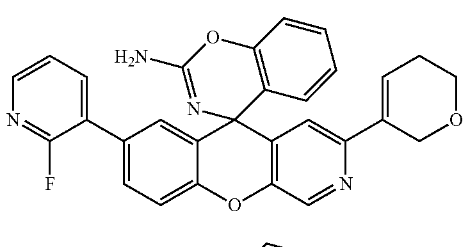 | 3'-(5,6-dihydro-2H-pyran-3-yl)-7'-(2-fluoropyridin-3-yl)spiro[benzo[e][1,3]oxazine-4,5'-chromeno[2,3-c]pyridin]-2-amine | 492.5 | 493.1 | 0.002 | 0.122 |
| 19 | 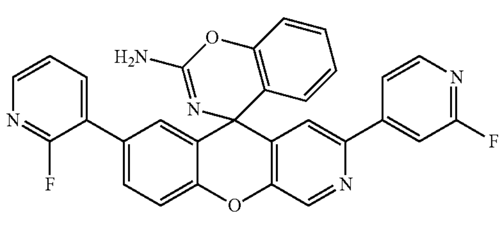 | 7'-(2-fluoropyridin-3-yl)-3'-(2-fluoropyridin-4-yl)spiro[benzo[e][1,3]oxazine-4,5'-chromeno[2,3-c]pyridin]-2-amine | 505.5 | 506.0 | 0.002 | |

TABLE I-continued

| Example No | Compound Structure | Compound Name | Calc MW | Observed MW | BAC E1 FERT assay (uM) | HEK cell assay (uM) |
|---|---|---|---|---|---|---|
| 20 | 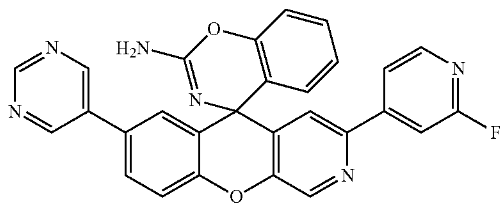 [SMILES: NC1=NC2(c3ccccc3O1)c1cc(-c3cncnc3)ccc1Oc1cnc(-c3ccnc(F)c3)cc12] | 3'-(2-fluoropyridin-4-yl)-7'-(pyrimidin-5-yl)spiro[benzo[c][1,3]oxazine-4,5-chromeno[2,3-c]pyridin]-2-amine | 489 | | 0.0027 | 0.106 |
| 21 | 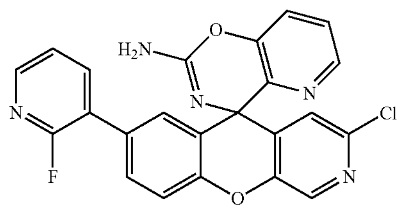 [SMILES: NC1=NC2(c3cc(-c4cccnc4F)ccc3Oc3cnc(Cl)cc32)c2ncccc2O1] | 3-chloro-7-(2-fluoropyridin-3-yl)spiro[chromeno[2,3-c]pyridine-5,4'-pyrido[2,3-e][1,3]oxazin]-2'-amine | 446 | | 0.37 | >10 |
| 22 | 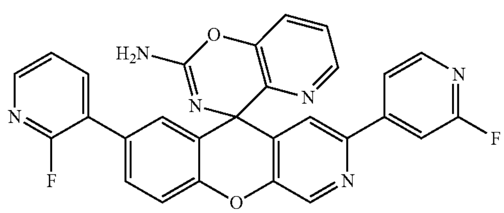 [SMILES: NC1=NC2(c3cc(-c4cccnc4F)ccc3Oc3cnc(-c4ccnc(F)c4)cc32)c2ncccc2O1] | 7-(2-fluoropyridin-3-yl)-3-(2-fluoropyridin-4-yl)spiro[chromeno[2,3-c]pyridine-5,4'-pyrido[2,3-e][1,3]oxazin]-2'-amine | 507 | | 0.0099 | 0.805 |
| 23 | 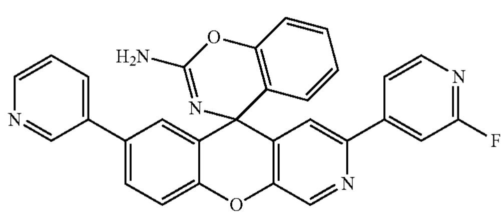 [SMILES: NC1=NC2(c3ccccc3O1)c1cc(-c3cccnc3)ccc1Oc1cnc(-c3ccnc(F)c3)cc12] | 3'-(2-fluoropyridin-4-yl)-7'-(pyridin-3-yl)spiro[benzo[e][1,3]oxazine-4,5'-chromeno[2,3-c]pyridin]-2-amine | 487.5 | | 0.0029 | 0.098 |
| 24 | 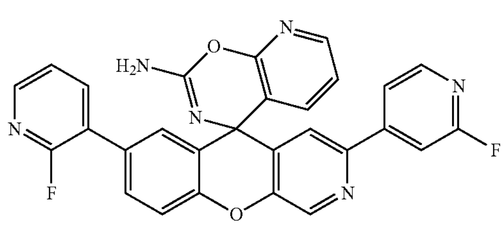 [SMILES: NC1=NC2(c3cc(-c4cccnc4F)ccc3Oc3cnc(-c4ccnc(F)c4)cc32)c2cccnc2O1] | 7-(2-fluoropyridin-3-yl)-3-(2-fluoropyridin-4-yl)spiro[chromeno[2,3-c]pyridine-5,4-pyrido[3,2-e][1,3]oxazin]-2'-amine | 506.9 | | 0.0018 | 0.32 |

The following compounds in Table 2 are additional representative examples of Formula I provided by the present invention.

TABLE 2

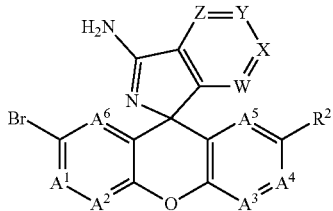

| Ex. No. | R² | A³ | A⁴ | R⁷ | X | Y |
|---|---|---|---|---|---|---|
| 25 | 3,6-dihydro-2H-pyran-4-yl | CH | N | 2-Fluoropyridin-3-yl | CH₂ | —N— |
| 26 | Pyridin-3-yl | CH | N | 2-Fluoropyridin-3-yl | CH₂ | —N— |
| 27 | 3,6-dihydro-2H-pyran-4-yl | CH | CH | 2-Fluoropyridin-3-yl | CH₂ | —O— |
| 28 | 2-F-pyrimidin-3-yl | CH | CH | 2-Fluoropyridin-3-yl | CH₂ | —N— |
| 29 | 3,6-dihydro-2H-pyran-4-yl | CH | N | 2-Fluoropyridin-3-yl | —N— | CH₂ |
| 30 | 2-F-pyrrolidin-1-yl | CH | N | 2-Fluoropyridin-3-yl | —N— | CH₂ |
| 31 | 3,6-dihydro-2H-pyran-4-yl | CH | N | 2-Fluoropyridin-3-yl | —N— | CH₂ |
| 32 | 3,6-dihydro-2H-pyran-4-yl | CF | N | 2-Fluoropyridin-3-yl | —N— | CH₂ |
| 33 | Pyridin-3-yl | CF | N | 2-Fluoropyridin-3-yl | —N— | CH₂ |
| 34 | 2-fluoropyridin-4-yl | CF | N | 2-Fluoropyridin-3-yl | —N— | CH₂ |
| 35 | tetrahydro-2H-pyran-4-yl | CF | N | 2-Fluoropyridin-3-yl | —N— | CH₂ |
| 36 | tetrahydro-2H-pyran-2-yl | CF | N | 2-Fluoropyridin-3-yl | —N— | CH₂ |
| 37 | tetrahydro-2H-pyran-3-yl | CF | N | 2-Fluoropyridin-3-yl | —N— | CH₂ |
| 38 | 3,6-dihydro-2H-pyran-4-yl | CF | N | 2-Fluoropyridin-3-yl | CH₂ | —N— |
| 39 | 2-F-pyrrolidin-1-yl | CF | N | 2-Fluoropyridin-3-yl | CH₂ | —N— |
| 40 | 2-F-pyrrolidin-1-yl | CF | N | pyridin-3-yl | CH₂ | —N— |
| 41 | tetrahydro-2H-pyran-4-yl | CF | N | 2-Fluoropyridin-3-yl | CH₂ | —N— |
| 42 | 5,6-dihydro-2H-pyran-3-yl | CF | N | 2-Fluoropyridin-3-yl | CH₂ | —N— |
| 43 | tetrahydro-2H-pyran-2-yl | CF | N | 2-Fluoropyridin-3-yl | CH₂ | —N— |
| 44 | tetrahydro-2H-pyran-3-yl | CF | N | 2-Fluoropyridin-3-yl | CH₂ | —N— |

The present invention also provides methods for making compounds of Formulas I-III, and sub-formulas therein. For example, the compounds in Table 2 and additional examples may be made by the following methods, as similarly described in the literature references mentioned below.

In one embodiment of the invention, there is provided a method of making a compound of Formula I, the method comprising the step of reacting a compound 20

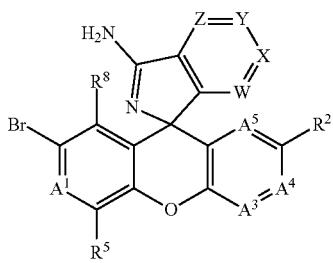

wherein $A^1, A^2, A^3, A^4, A^5, A^6, R^2, W, X, Y$ and $Z$ of Formula I are as defined herein, with a compound having the structure

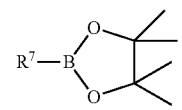

or $R^7$—$B(OH)_2$, wherein $R^7$ is as defined herein, to make a compound of Formula I.

In another embodiment of the invention, there is provided a method of making a compound of Formula I-A, the method comprising the step of reacting a compound 20

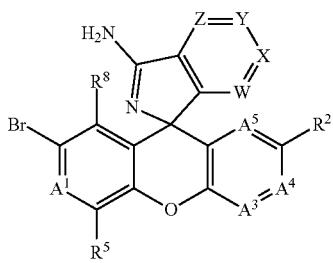

wherein $A^1, A^3, A^4, A^5, R^2, R^5, R^8, W, X, Y$ and $Z$ of Formula I-A are as defined herein, with a compound having the structure

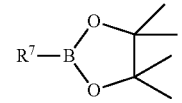

or $R^7$—$B(OH)_2$, wherein $R^7$ is as defined herein, to make a compound of Formula I-A.

In another embodiment of the invention, there is provided a method of making a compound of Formula I-B, the method comprising the step of reacting a compound 20

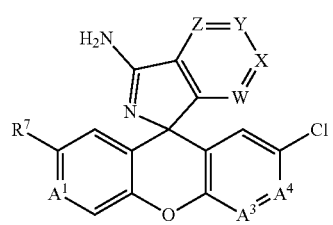

wherein $A^1$, $A^3$, $A^4$, $R^7$, W, X, Y and Z of Formula I-B are as defined herein, with a compound having the structure

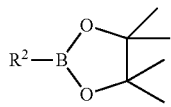

$R^2$—$B(OH)_2$ or wherein $R^2$ is as defined herein, to make a compound of Formula I-B.

In another embodiment of the invention, there is provided a method of making a compound of Formula II, the method comprising the step of reacting a compound 20

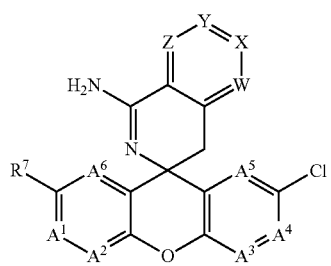

wherein $A^1$, $A^2$, $A^3$, $A^4$, $A^5$, $A^6$, $R^7$, W, X, Y and Z of Formula II are as defined herein, with a compound having the structure

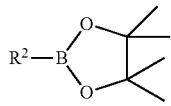

or $R^2$—$B(OH)_2$, wherein $R^2$ is as defined herein, to make a compound of Formula II.

In another embodiment of the invention, there is provided a method of making a compound of Formula III, the method comprising the step of reacting a compound 20

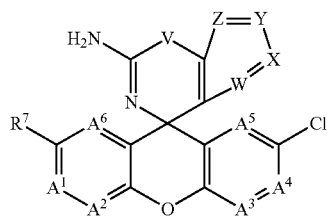

wherein $A^1$, $A^2$, $A^3$, $A^4$, $A^5$, $A^6$, $R^7$, V, W, X, Y and Z of Formula III are as defined herein, with a compound having the structure

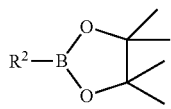

or $R^2$—$B(OH)_2$, wherein $R^2$ is as defined herein, to make a compound of Formula III.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H⁺ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H (deuterium), $^3$H (tritium), $^{13}$C, $^{14}$C, $^{15}$N, $^{16}$O, $^{17}$O, $^{31}$P, $^{35}$S, $^{18}$F, and $^{36}$O.

Compounds of the present invention that contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Deuterated ($^2$H), Tritiated ($^3$H) and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (fluorescence resonance energy transfer) Assay (Enzyme Assay data in the Example Table I)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Table I.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ40 levels were determined using a sandwich ELISA. The $IC_{50}$ of the compound was calculated from the percent of control or percent inhibition of Aβ40 as a function of the concentration of the test compound.

The sandwich ELISA to detect Aβ40 was performed in 96 well microtiter plates, which were pre-treated with goat anti-rabbit IgG (Pierce). The capture and detecting antibody pair that were used to detect Aβ40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Table I.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76,173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2

IV: 5% EtOH, 45% Propylene glycol in 5% Dextrose

The compounds of the invention may be shown to reduce the formation and/or deposition of amyloid beta peptide in the cerebrospinal fluid (CSF) as well as in the brain of a mouse or rat at both 10 mpk (mpk=mg compound per kg animal) and 30 mpk dosing concentrations after 4 hrs. For example, the compound of examples 7-B exhibited a 7% CSF abeta reduction and 10% brain abeta reduction, respectively, while example 17e exhibited a 41% CSF abeta reduction and 28% brain abeta reduction, respectively, each administered at a pharmacodynamic (PD) dose of 10 mg/kg in a rat.

Indications

The compounds of the invention have been shown to modulate, and specifically inhibit the activity of beta-secretase enzyme, thereby reducing the A-beta peptide fragments believed to be responsible for Alzheimer's Disease (AD). Bapineuzamab, a monoclonal amino-terminus specific anti-amyloid antibody is presently in Phase III clinical trials for the treatment of AD. *Alzheimer's Research & Therapy*, 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier amd more common. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, *Bloomberg News, The Boston Globe*, Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, I-A, I-A-I, I-B, II, III or III-B. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I and II may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I:

or a stereoisomer, tautomer, hydrate, solvate or pharmaceutically acceptable salt thereof, wherein
$A^1$ is CH;
$A^2$ is CH;
$A^3$ is $CR^4$ or N;
$A^4$ is $CR^3$ or N;
$A^5$ is CH;
$A^6$ is CH, provided that no more than one of $A^3$ and $A^4$, is N;
$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the $C_{1-6}$alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;
$R^3$ is H, F, Cl, Br, $CF_3$ $OCF_3CH_3$ or CN;
$R^4$ is H, F, Cl, Br, $CF_3$ $OCF_3CH_3$ or CN;
$R^7$ is a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, said ring optionally substituted, independently, with 1-3 substituents of $R^9$;
each $R^9$, independently, is halo, haloalkyl, CN, OH, $NO_2$, $NH_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl,
each of W, X, Y and Z, independently, is $CR^{10}$ or N, wherein each $R^{10}$, independently, is H, F, Cl, Br, $CF_3$, $OCF_3$, $C_{1-6}$-alkyl, CN, OH, —$OC_{1-6}$-alkyl,
provided that no more than one of W, X, Y and Z are N.

2. The compound of claim 1, or a stereoisomer, tautomer or pharmaceutically acceptable salt thereof, wherein
$A^1$ is CH;
$A^2$ is CH;
$A^3$ is CH, CF or N;
$A^4$ is CH, CF or N;
$A^5$ is CH;
$A^6$ is CH; and
each of W, X, Y and Z, independently, is $CR^{10}$ or N, wherein each $R^{10}$, independently, is H, F, Cl, Br, $CF_3$, $OCF_3$, $C_{1-6}$-alkyl or CN.

3. The compound of claim 1, or a pharmaceutically acceptable salt thereof, wherein
$R^4$ is H or F;
each of W, X, Y and Z, independently, is $CR^{10}$ or N, wherein each $R^{10}$, independently, is H, F, Cl or Br.

4. The compound of claim 1, or a pharmaceutically acceptable salt thereof, wherein
$R^4$ is H, F, methyl, CN or OH;
$R^2$ is halo, haloalkyl, haloalkoxyl, $C_{1-6}$-alkyl, $C_2$alkenyl, $C_{2-4}$alkynyl, $C_{3-8}$-cycloalkyl, $OR^{10}$, $SR^{10}$ or a ring of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, wherein the $C_{1-6}$-alkyl, $C_{2-4}$alkenyl, $C_{2-4}$alkynyl, $C_{3-8}$-cycloalkyl and ring are optionally substituted, independently, with 1-3 substituents of $R^9$;
$R^3$ is H, F or Cl;
$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and
each of W, X, Y and Z, independently, is $CR^{10}$ wherein each $R^{10}$, independently, is H, F, Cl, Br, $CH_3$, $CF_3$, OH, —$OCH_3$, —$OCF_3$, or CN.

5. The compound of claim 2, or a stereoisomer or pharmaceutically acceptable salt thereof, selected from
3-chloro-1-fluoro-7-(2-fluoropyridin-3-yl)spiro[chromeno[2,3-c]pyridine-5,1'-isoindol]-3'-amine;
1-fluoro-7-(2-fluoropyridin-3-yl)-3-(2-fluoropyridin-4-yl)spiro[chromeno[2,3-c]pyridine-5,1'-isoindol]-3'-amine;
(S)-1-fluoro-7-(2-fluoropyridin-3-yl)-3-(2-fluoropyridin-4-yl)spiro[chromeno[2,3-c]pyridine-5,1'-isoindol]-3'-amine;

(R)-1-fluoro-7-(2-fluoropyridin-3-yl)-3-(2-fluoropyridin-4-yl)spiro[chromeno[2,3-c]pyridine-5,1'-isoindol]-3'-amine;
3-(3,6-dihydro-2H-pyran-4-yl)-1-fluoro-7-(2-fluoropyridin-3-yl)spiro[chromeno[2,3-c]pyridine-5,1'-isoindol]-3'-amin;
3-(5,6-dihydro-2H-pyran-3-yl)-1-fluoro-7-(2-fluoropyridin-3-yl)spiro[chromeno[2,3-c]pyridine-5,1'-isoindol]-3'-amine;
(R)-3-(5,6-dihydro-2H-pyran-3-yl)-1-fluoro-7-(2-fluoropyridin-3-yl)spiro[chromeno[2,3-c]pyridine-5,1'-isoindol]-3'-amin;
(S)-3-(5,6-dihydro-2H-pyran-3-yl)-1-fluoro-7-(2-fluoropyridin-3-yl)spiro[chromeno[2,3-c]pyridine-5,1'-isoindol]-3'-amine;
1-fluoro-7-(2-fluoropyridin-3-yl)-3-morpholinospiro[chromeno[2,3-c]pyridine-5,1'-isoindol]-3'-amine;
3-(3,3-difluoropyrrolidin-1-yl)-1-fluoro-7-(2-fluoropyridin-3-yl)spiro[chromeno[2,3-c]pyridine-5,1'-isoindol]-3'-amine;
3-chloro-7-(2-fluoropyridin-3-yl)spiro[chromeno[2,3-c]pyridine-5,1'-isoindol]-3'-amine;
7-(2-fluoropyridin-3-yl)-3-(2-fluoropyridin-4-yl)spiro[chromeno[2,3-c]pyridine-5,1'-isoindol]-3'-amine;
3-(3,6-dihydro-2H-pyran-4-yl)-7-(2-fluoropyridin-3-yl)spiro[chromeno[2,3-c]pyridine-5,1'-isoindol]-3'-amine;
7-(2-fluoropyridin-3-yl)-3-(tetrahydro-2H-pyran-4-yl)spiro[chromeno[2,3-c]pyridine-5,1'-isoindol]-3'-amine;
3-(3,3-dimethylbut-1-ynyl)-7-(2-fluoropyridin-3-yl)spiro[chromeno[2,3-c]pyridine-5,1'-isoindol]-3'-amine;
(S)-3,7-bis(2-fluoropyridin-3-yl)spiro[chromeno[2,3-c]pyridine-5,1'-isoindol]-3'-amine;
3-chloro-1-fluoro-7-(2-fluoropyridin-3-yl)spiro[chromeno[2,3-c]pyridine-5,3'-pyrrolo[3,4-c]pyridin]-1'-amine;
(R)-3-chloro-1-fluoro-7-(2-fluoropyridin-3-yl)spiro[chromeno[2,3-c]pyridine-5,3'-pyrrolo[3,4-c]pyridin]-1'-amine;
(S)-1-fluoro-7-(2-fluoropyridin-3-yl)-3-(2-fluoropyridin-4-yl)spiro[chromeno[2,3-c]pyridine-5,3'-pyrrolo[3,4-c]pyridin]-1'-amine;
(R)-1-fluoro-7-(2-fluoropyridin-3-yl)-3-(2-fluoropyridin-4-yl)spiro[chromeno[2,3-c]pyridine-5,3'-pyrrolo[3,4-c]pyridin]-1'-amine;
1-fluoro-7-(2-fluoropyridin-3-yl)-3-(2-fluoropyridin-4-yl)spiro[chromeno[2,3-c]pyridine-5,7'-pyrrolo[3,4-b]pyridin]-5'-amine;
(S)-3-(5,6-dihydro-2H-pyran-3-yl)-1-fluoro-7-(2-fluoropyridin-3-yl)spiro[chromeno[2,3-c]pyridine-5,5'-pyrrolo[3,4-b]pyridin]-7'-amine;
(S)-3-(5,6-dihydro-2H-pyran-3-yl)-1-fluoro-7-(2-fluoropyridin-3-yl)spiro[chromeno[2,3-c]pyridine-5,3'-pyrrolo[3,4-c]pyridin]-1'-amine; and
(S)-1-fluoro-7-(2-fluoropyridin-3-yl)-3-morpholinospiro[chromeno[2,3-c]pyridine-5,5'-pyrrolo[3,4-b]pyridin]-7'-amine.

6. A pharmaceutical composition comprising a compound according to claim 1 and a pharmaceutically acceptable excipient.

7. A process for preparing a compound of claim 1, the process comprising the step of reacting a compound 20

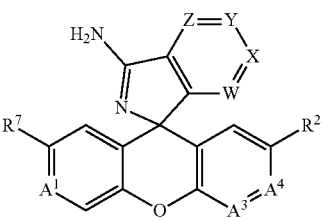

wherein $A^1$, $A^3$, $A^4$, $R^7$, W, X, Y and Z of Formula I-B are as defined in claim 1, with a compound having the structure

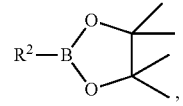

$R^2$—$B(OH)_2$ or wherein $R^2$ is as defined in claim 1 to prepare the compound of claim 1.

* * * * *